(12) United States Patent
Clevers et al.

(10) Patent No.: US 10,940,180 B2
(45) Date of Patent: Mar. 9, 2021

(54) METHOD FOR IDENTIFYING, EXPANDING, AND REMOVING ADULT STEM CELLS AND CANCER STEM CELLS

(71) Applicant: Koninklijke Nederlandse Akademie van Wetenschappen, Utrecht (NL)

(72) Inventors: Johannes C. Clevers, Huis Ter Heide (NL); Nicholas Barker, Utrecht (NL); Andrea Haegebarth, Berlin (DE); Marcus Lambertus Van de Wetering, Houten (NL)

(73) Assignee: Koninklijke Nederlandse Akademie van Wetenschappen, Utrecht (NL)

( * ) Notice: Subject to any disclaimer, the term of this patent is extended or adjusted under 35 U.S.C. 154(b) by 81 days.

(21) Appl. No.: 15/813,863

(22) Filed: Nov. 15, 2017

(65) Prior Publication Data

US 2018/0221441 A1    Aug. 9, 2018

Related U.S. Application Data

(60) Division of application No. 14/494,511, filed on Sep. 23, 2014, now Pat. No. 9,833,496, which is a continuation of application No. 12/705,336, filed on May 10, 2010, now Pat. No. 8,906,631, which is a continuation of application No. PCT/NL2008/050543, filed on Aug. 8, 2008.

(30) Foreign Application Priority Data

Aug. 10, 2007 (EP) .................... 07114192

(51) Int. Cl.
  *G01N 33/50* (2006.01)
  *A61K 38/17* (2006.01)
  *C12N 5/071* (2010.01)
  *A61K 45/06* (2006.01)

(52) U.S. Cl.
  CPC ............ *A61K 38/177* (2013.01); *A61K 45/06* (2013.01); *C12N 5/068* (2013.01); *G01N 33/5011* (2013.01)

(58) Field of Classification Search
  CPC ... A61K 38/177; A61K 45/06; G01N 33/5011
  See application file for complete search history.

(56) References Cited

U.S. PATENT DOCUMENTS

| | | |
|---|---|---|
| 7,056,685 B1 | 6/2006 | Chen et al. |
| 7,419,825 B2 | 9/2008 | Klassen et al. |
| 8,642,339 B2 | 2/2014 | Sato et al. |
| 8,906,631 B2 | 12/2014 | Clevers et al. |
| 9,752,124 B2 | 9/2017 | Clevers et al. |
| 9,765,301 B2 | 9/2017 | Huch Ortega et al. |
| 9,833,496 B2 | 12/2017 | Clevers et al. |
| 10,006,904 B2 | 6/2018 | Beekman et al. |
| 2007/0280927 A1 | 12/2007 | Hopf et al. |
| 2012/0196312 A1 | 8/2012 | Sato et al. |
| 2013/0189327 A1 | 7/2013 | Ortega et al. |
| 2014/0044713 A1 | 2/2014 | De Lau et al. |
| 2014/0243227 A1 | 8/2014 | Clevers et al. |
| 2014/0256037 A1 | 9/2014 | Sato et al. |
| 2015/0011420 A1 | 1/2015 | Beekman et al. |
| 2018/0066233 A1 | 3/2018 | Huch Ortega et al. |
| 2018/0072995 A1 | 3/2018 | Sato et al. |
| 2019/0100728 A1 | 4/2019 | Sato et al. |
| 2019/0383799 A1 | 12/2019 | Beekman et al. |

FOREIGN PATENT DOCUMENTS

| | | |
|---|---|---|
| CA | 2 511 907 A1 | 7/2004 |
| CN | 1925869 A | 3/2007 |
| CN | 1940062 A | 4/2007 |
| EP | 1 602 930 A2 | 12/2005 |
| EP | 1 602 930 A3 | 10/2006 |
| WO | WO 2004/061423 A2 | 7/2004 |
| WO | WO 2005/074980 A1 | 8/2005 |
| WO | WO 2009/022907 A2 | 2/2009 |

OTHER PUBLICATIONS

Guzman ML, Swiderski CF, Howard DS, Grimes BA, Rossi RM, Szilvassy SJ, Jordan CT (2002) Proc Natl Acad Sci USA 99:16220-16225.*
Dalerba (2007, 104:10158-10163).*
U.S. Appl. No. 12/705,336, filed May 10, 2010, Granted, U.S. Pat. No. 8,906,631.
U.S. Appl. No. 14/494,511, filed Sep. 23, 2014, Granted, U.S. Pat. No. 9,833,496.
U.S. Appl. No. 13/147,163, filed Sep. 14, 2011, Granted, U.S. Pat. No. 8,642,339.
U.S. Appl. No. 14/079,545, filed Nov. 13, 2013, Published, 2014-0256037.
U.S. Appl. No. 13/194,866, filed Jul. 29, 2011, Granted, U.S. Pat. No. 9,752,124.
U.S. Appl. No. 15/654,243, filed Jul. 19, 2017, Published, 2018-0072995.

(Continued)

*Primary Examiner* — Valarie E Bertoglio
(74) *Attorney, Agent, or Firm* — Wolf, Greenfield & Sacks, P.C.

(57) ABSTRACT

The invention relates to the fields of biochemistry, pharmacy and oncology. The invention particularly relates to the use of novel stem cell markers for the isolation of stem cells. The invention further relates to the obtained stem cells and their use in for example research or treatment, for example, for the preparation of a medicament for the treatment of damaged or diseased tissue.
In one of the embodiments, the invention provides a method for obtaining (or isolating) stem cells comprising optionally preparing a cell suspension from a tissue or organ sample, contacting said cell suspension with an Lgr 6 or 5 binding compound, identify the cells bound to said binding compound, and optionally isolating the stem cells from said binding compound.
The invention further relates to means suitable for cancer treatment and even more specific for the treatment of cancer by eradicating cancer stem cells.

6 Claims, 28 Drawing Sheets

Figure 1:
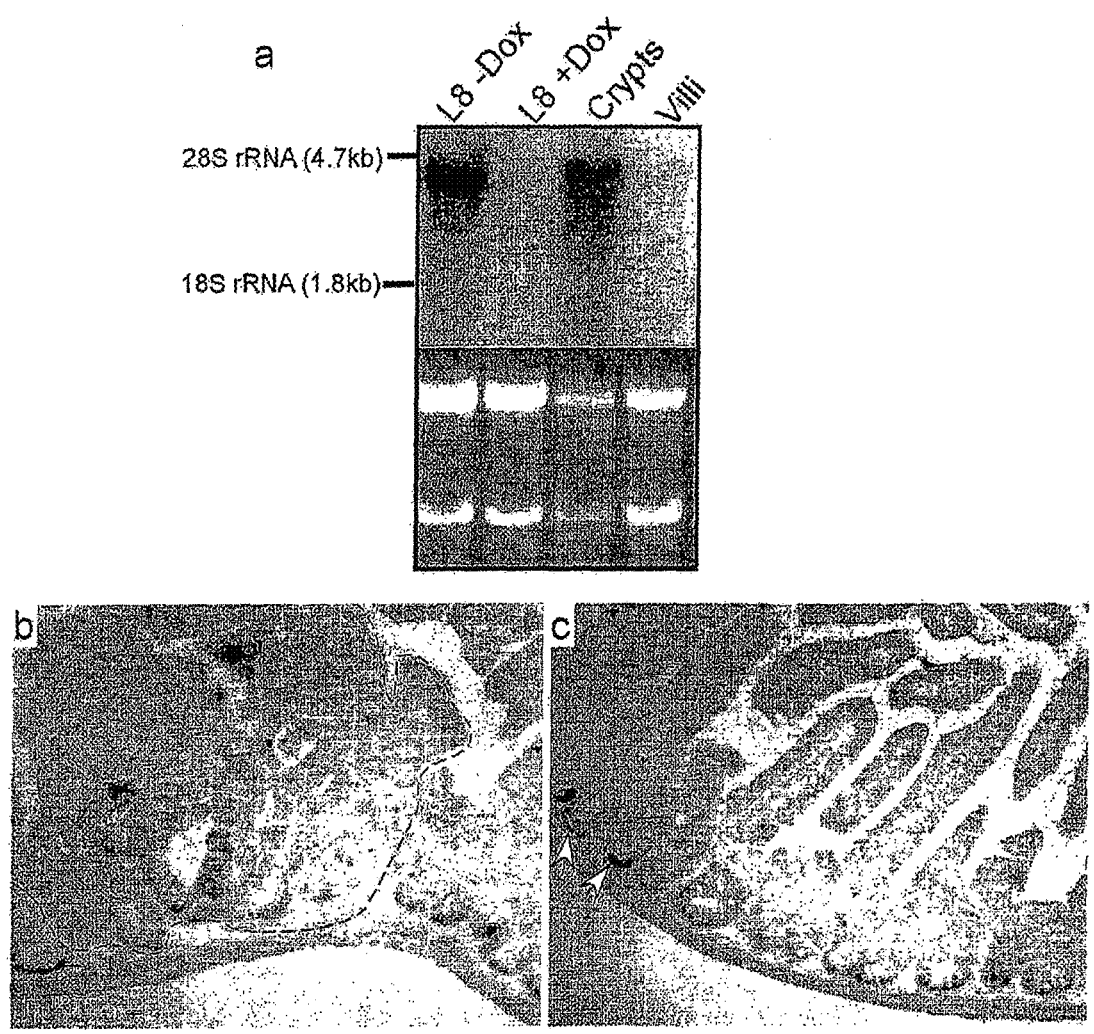

Specification includes a Sequence Listing.

(56) References Cited

OTHER PUBLICATIONS

U.S. Appl. No. 13/812,614, filed Apr. 8, 2013, Granted, U.S. Pat. No. 9,765,301.
U.S. Appl. No. 15/665,363, filed Jul. 31, 2017, Published, 2018-0066233.
U.S. Appl. No. 14/124,884, filed May 9, 2014, Published, 2014-0243227.
U.S. Appl. No. 14/367,061, filed Jun. 19, 2014, Allowed, 2015-0011420.
PCT/NL2008/050543, May 7, 2009, International Search Report and Written Opinion.
PCT/NL2008/050543, Feb. 16, 2010, International Preliminary Report on Patentability.
EP08793835.3, Oct. 9, 2010, European Communication.
International Search Report and Written Opinion for PCT/NL2008/050543 dated May 7, 2009.
International Preliminary Report on Patentability for PCT/NL2008/050543 dated Feb. 16, 2010.
European Communication for EP08793835.3 dated Oct. 9, 2010.
[No Author Listed] Dynabeads® M-450 Tosylactivated, Advertisement Sheet dated Aug. 10, 2009.
Akolkar et al., Different VL and VH germ-line genes are used to produce similar combining sites with specificity for alpha(1----6)dextrans. J Immunol. Jun. 15, 1987;138(12):4472-9. Erratum in: J Immunol. Dec. 1, 1987;139(11):3911.
Al-Hajj et al., Prospective identification of tumorigenic breast cancer cells. Proc Natl Acad Sci U S A. Apr. 1, 2003;100(7):3983-8. Epub Mar. 10, 2003. Erratum in: Proc Natl Acad Sci U S A. May 27, 2003;100(11):6890.
Bach et al., Stem cells: the intestinal stem cell as a paradigm. Carcinogenesis. Mar. 2000;21(3):469-76.
Barker et al., Identification of stem cells in small intestine and colon by marker gene Lgr5. Nature. Oct. 25, 2007;449(7165):1003-7. Epub Oct. 14, 2007.
Barker et al., The intestinal stem cell. Genes Dev. Jul. 15, 2008;22(14):1856-64. doi: 10.1101/gad.1674008.
Bastide et al., Sox9 regulates cell proliferation and is required for Paneth cell differentiation in the intestinal epithelium. J Cell Biol. Aug. 13, 2007;178(4):635-48.
Batlle et al., Beta-catenin and TCF mediate cell positioning in the intestinal epithelium by controlling the expression of EphB/ephrinB. Cell. Oct. 18, 2002;111(2):251-63.
Becker et al., M1930 Lgr5 Is a Novel and Promising Marker for Dysplastic Progression and Adenocarcinoma of the Esophagus. Gastroenterology. Apr. 2008; 134(4):A-433.
Bjerknes et al., Clonal analysis of mouse intestinal epithelial progenitors. Gastroenterology. Jan. 1999;116(1):7-14.
Bjerknes et al., Multipotential stem cells in adult mouse gastric epithelium. Am J Physiol Gastrointest Liver Physiol. Sep. 2002;283(3):G767-77.
Bjerknes et al., Re-examination of P-PTEN staining patterns in the intestinal crypt. Nat Genet. Oct. 2005;37(10):1016-7; author reply 1017-8.
Bjerknes et al., The stem-cell zone of the small intestinal epithelium. I. Evidence from Paneth cells in the adult mouse. Am J Anat. Jan. 1981;160(1):51-63.
Bjerknes et al., The stem-cell zone of the small intestinal epithelium. II. Evidence from Paneth cells in the newborn mouse. Am J Anat. Jan. 1981;160(1):65-75.
Bjerknes et al., The stem-cell zone of the small intestinal epithelium. III. Evidence from columnar, enteroendocrine, and mucous cells in the adult mouse. Am J Anat. Jan. 1981;160(1):77-91.
Blache et al., SOX9 is an intestine crypt transcription factor, is regulated by the Wnt pathway, and represses the CDX2 and MUC2 genes. J Cell Biol. Jul. 5, 2004;166(1):37-47.
Blanpain et al., Epidermal homeostasis: a balancing act of stem cells in the skin. Nat Rev Mol Cell Biol. Mar. 2009;10(3):207-17. doi: 10.1038/nrm2636. Epub Feb. 11, 2009.
Blanpain et al., Epidermal stem cells of the skin. Annu Rev Cell Dev Biol. 2006;22:339-73.
Blanpain et al., Self-renewal, multipotency, and the existence of two cell populations within an epithelial stem cell niche. Cell. Sep. 3, 2004;118(5):635-48.
Bonnet et al., Human acute myeloid leukemia is organized as a hierarchy that originates from a primitive hematopoietic cell. Nat Med. Jul. 1997;3(7):730-7.
Booth et al., Gut instincts: thoughts on intestinal epithelial stem cells. J Clin Invest. Jun. 2000;105(11):1493-9.
Brigelius-Flohé, Glutathione peroxidases and redox-regulated transcription factors. Biol Chem. Oct.-Nov. 2006;387(10-11):1329-35.
Broedel et al. The case for serum-free media. BioProcess Intl. Feb. 2003; pp. 56-58.
Cheng et al., Origin, differentiation and renewal of the four main epithelial cell types in the mouse small intestine. V. Unitarian Theory of the origin of the four epithelial cell types. Am J Anat. Dec. 1974;141(4):537-61.
Clarke et al., Cancer stem cells—perspectives on current status and future directions: AACR Workshop on cancer stem cells. Cancer Res. Oct. 1, 2006;66(19):9339-44. Epub Sep. 21, 2006.
Claudinot et al., Long-term renewal of hair follicles from clonogenic multipotent stem cells. Proc Natl Acad Sci U S A. Oct. 11, 2005;102(41):14677-82. Epub Oct. 3, 2005.
Clayton et al., A single type of progenitor cell maintains normal epidermis. Nature. Mar. 8, 2007;446(7132):185-9. Epub Feb. 28, 2007.
Collins et al., Prostate cancer stem cells. Eur J Cancer. Jun. 2006;42(9):1213-8. Epub May 2, 2006.
Cotsarelis et al., Label-retaining cells reside in the bulge area of pilosebaceous unit: implications for follicular stem cells, hair cycle, and skin carcinogenesis. Cell. Jun. 29, 1990;61(7):1329-37.
De Lau et al., Lgr5 homologues associate with Wnt receptors and mediate R-spondin signalling. Nature. Jul. 4, 2011;476(7360):293-7. doi: 10.1038/nature10337.
Gregorieff et al., Wnt signaling in the intestinal epithelium: from endoderm to cancer. Genes Dev. Apr. 15, 2005;19(8):877-90.
Haramis et al., De novo crypt formation and juvenile polyposis on BMP inhibition in mouse intestine. Science. Mar. 12, 2004;303(5664):1684-6.
He et al., BMP signaling inhibits intestinal stem cell self-renewal through suppression of Wnt-beta-catenin signaling. Nat Genet. Oct. 2004;36(10):1117-21. Epub Sep. 19, 2004.
Hewitt et al., The claudin gene family: expression in normal and neoplastic tissues. BMC Cancer. Jul. 12, 2006;6:186.
Hsu et al., Activation of orphan receptors by the hormone relaxin. Science. Jan. 25, 2002;295(5555):671-4.
Hsu et al., Characterization of two LGR genes homologous to gonadotropin and thyrotropin receptors with extracellular leucine-rich repeats and a G protein-coupled, seven-transmembrane region. Mol Endocrinol. Dec. 1998;12(12):1830-45.
Hsu et al., The three subfamilies of leucine-rich repeat-containing G protein-coupled receptors (LGR): identification of LGR6 and LGR7 and the signaling mechanism for LGR7. Mol Endocrinol. Aug. 2000;14(8):1257-71.
Hsu, New insights into the evolution of the relaxin-LGR signaling system. Trends Endocrinol Metab. Sep. 2003;14(7):303-9.
Ireland et al., Cellular inheritance of a Cre-activated reporter gene to determine Paneth cell longevity in the murine small intestine. Dev Dyn. Aug. 2005;233(4):1332-6.
Ito et al., Stem cells in the hair follicle bulge contribute to wound repair but not to homeostasis of the epidermis. Nat Med. Dec. 2005;11(12):1351-4. Epub Nov. 20, 2005.
Jaks et al., Lgr5 marks cycling, yet long-lived, hair follicle stem cells. Nat Genet. Nov. 2008;40(11):1291-9. doi: 10.1038/ng.239. Epub Oct. 12, 2008.
Jones et al., Comparative lesion sequencing provides insights into tumor evolution. Proc Natl Acad Sci U S A. Mar. 18, 2008;105(11):4283-8. doi: 10.1073/pnas.0712345105. Epub Mar. 12, 2008.
Jung et al., Isolation and in vitro expansion of human colonic stem cells. Nat Med. Sep. 4, 2011;17(10):1225-7. doi: 10.1038/nm.2470.

(56) References Cited

OTHER PUBLICATIONS

Kato et al., Leucine-rich repeat-containing G protein-coupled receptor-4 (LGR4, Gpr48) is essential for renal development in mice. Nephron Exp Nephrol. 2006;104(2):e63-75. Epub Jun. 19, 2006.

Khavari, Profiling epithelial stem cells. Nat Biotechnol. Apr. 2004;22(4):393-4.

Kinzler et al., Lessons from hereditary colorectal cancer. Cell. Oct. 18, 1996;87(2):159-70.

Kirschmeier, Identification of overexpression of orphan G Protein-Coupled Receptor GPR49 in human colon and ovarian primary tumors. Proc Amer Assoc Cancer Res. 2006;47: Abstract #4162.

Kobayashi et al., LGR5-positive colon cancer stem cells interconvert with drug-resistant LGR5-negative cells and are capable of tumor reconstitution. Stem Cells. 2012;30:2631-44.

Korinek et al., Depletion of epithelial stem-cell compartments in the small intestine of mice lacking Tcf-4. Nat Genet. Aug. 1998;19(4):379-83.

Korinek et al., Constitutive transcriptional activation by a beta-catenin-Tcf complex in APC-/- colon carcinoma. Science. Mar. 21, 1997;275(5307):1784-7.

Lapidot et al., A cell initiating human acute myeloid leukaemia after transplantation into SCID mice. Nature. Feb. 17, 1994;367(6464):645-8.

Li et al., Bat guano virome: predominance of dietary viruses from insects and plants plus novel mammalian viruses. J Virology. Jul. 2010;84(14):6955-65.

Lin et al., Identification of hair cycle-associated genes from time-course gene expression profile data by using replicate variance. Proc Natl Acad Sci U S A. Nov. 9, 2004;101(45):15955-60. Epub Nov. 1, 2004.

Longo et al., Characterization and drug sensitivity of four newly established colon adenocarcinoma cell lines to antifolate inhibitors of thymidylate synthase. Oncology Research. 2000;12:309-14.

Lowry et al., Defining the impact of beta-catenin/Tcf transactivation on epithelial stem cells. Genes Dev. Jul. 1, 2005;19(13):1596-611. Epub Jun. 16, 2005.

Malaterre et al., c-Myb is required for progenitor cell homeostasis in colonic crypts. Proc Natl Acad Sci U S A. Mar. 6, 2007;104(10):3829-34. Epub Feb. 26, 2007.

Marshman et al., The intestinal epithelial stem cell. Bioessays. Jan. 2002;24(1):91-8.

Mazerbourg et al., Leucine-rich repeat-containing, G protein-coupled receptor 4 null mice exhibit intrauterine growth retardation associated with embryonic and perinatal lethality. Mol Endocrinol. Sep. 2004;18(9):2241-54. Epub Jun. 10, 2004.

McClanahan et al., Identification of overexpression of orphan G protein-coupled receptor GPR49 in human colon and ovarian primary tumors. Cancer Biol Ther. Apr. 2006;5(4):419-26. Epub Apr. 19, 2006.

Mendive et al., Defective postnatal development of the male reproductive tract in LGR4 knockout mice. Dev Biol. Feb. 15, 2006;290(2):421-34. Epub Jan. 9, 2006.

Mori-Akiyama et al., SOX9 is required for the differentiation of paneth cells in the intestinal epithelium. Gastroenterology. Aug. 2007;133(2):539-46. Epub May 21, 2007.

Morin et al., Activation of beta-catenin-Tcf signaling in colon cancer by mutations in beta-catenin or APC. Science. Mar. 21, 1997;275(5307):1787-90.

Morita et al., Neonatal lethality of LGR5 null mice is associated with ankyloglossia and gastrointestinal distension. Mol Cell Biol. Nov. 2004;24(22):9736-43.

Morris et al., Capturing and profiling adult hair follicle stem cells. Nat Biotechnol. Apr. 2004;22(4):411-7. Epub Mar. 14, 2004.

Muncan et al., Rapid loss of intestinal crypts upon conditional deletion of the Wnt/Tcf-4 target gene c-Myc. Mol Cell Biol. Nov. 2006;26(22):8418-26. Epub Sep. 5, 2006.

Nakano et al., Brain tumor stem cells. Pediatr Res. Apr. 2006;59(4 Pt2):54R-8R.

Neid et al., Epidemiology, pathology, and staging of mesenchymal and endocrine tumours of the gastrointestinal tract. Chirurgische Gastroenterologie Interdisziplinar. 2007; 23(2):108-12 (Summary in English).

Ng et al., Lgr5 marks stem/progenitor cells in ovary and tubal epithelia. Nat Cell Bio. Aug. 2014;16(8):745-57. Suppl Info 10 pages.

Nishimura et al., Expression of Musashi-1 in human normal colon crypt cells: a possible stem cell marker of human colon epithelium. Dig Dis Sci. Aug. 2003;48(8):1523-9.

O'Brien et al., A human colon cancer cell capable of initiating tumour growth in immunodeficient mice. Nature. Jan. 4, 2007;445(7123):106-10. Epub Nov. 19, 2006.

Ohlstein et al., The stem cell niche: theme and variations. Curr Opin Cell Biol. Dec. 2004;16(6):693-9.

Pardal et al., Applying the principles of stem-cell biology to cancer. Nature Reviews. Dec. 2003;3:895-902.

Potten et al., Identification of a putative intestinal stem cell and early lineage marker; musashi-1. Differentiation. Jan. 2003;71(1):28-41.

Potten et al., Intestinal stem cells protect their genome by selective segregation of template DNA strands. J Cell Sci. Jun. 1, 2002;115(Pt 11):2381-8.

Potten et al., The intestinal epithelial stem cell: the mucosal governor. Int J Exp Pathol. Aug. 1997;78(4):219-43.

Potten, Kinetics and possible regulation of crypt cell populations under normal and stress conditions. Bull Cancer. Oct.-Dec. 1975;62(4):419-30.

Radtke et al., Self-renewal and cancer of the gut: two sides of a coin. Science. Mar. 25, 2005;307(5717):1904-9.

Reya et al., Stem cells, cancer, and cancer stem cells. Nature. Nov. 1, 2001;414(6859):105-11.

Reya et al., Wnt signalling in stem cells and cancer. Nature. Apr. 14, 2005;434(7035):843-50.

Ricci-Vitiani et al., Identification and expansion of human colon-cancer-initiating cells. Nature. Jan. 4, 2007;445(7123):111-5. Epub Nov. 19, 2006.

Sansom et al., Cyclin D1 is not an immediate target of beta-catenin following Apc loss in the intestine. J Biol Chem. Aug. 5, 2005;280(31):28463-7. Epub Jun. 9, 2005.

Sansom et al., Loss of Apc in vivo immediately perturbs Wnt signaling, differentiation, and migration. Genes Dev. Jun. 15, 2004;18(12):1385-90.

Sansom et al., Myc deletion rescues Apc deficiency in the small intestine. Nature. Apr. 5, 2007;446(7136):676-9. Epub Mar. 21, 2007.

Shibata et al., Rapid colorectal adenoma formation initiated by conditional targeting of the Apc gene. Science. Oct. 3, 1997;278(5335):120-3.

Siebertz et al., Expression of glypican-4 in haematopoietic-progenitor and bone-marrow-stromal cells. Biochem J. Dec. 15, 1999;344 Pt 3:937-43.

Singh et al., Identification of a cancer stem cell in human brain tumors. Cancer Res. Sep. 15, 2003;63(18):5821-8.

Sleeman et al., Dissociation of estrogen receptor expression and in vivo stem cell activity in the mammary gland. J Cell Biol. Jan. 1, 2007;176(1):19-26. Epub Dec. 26, 2006.

Soriano, Generalized lacZ expression with the ROSA26 Cre reporter strain. Nat Genet. Jan. 1999;21(1):70-1.

Stappenbeck et al., Molecular features of adult mouse small intestinal epithelial progenitors. Proc Natl Acad Sci U S A. Feb. 4, 2003;100(3) 1004-9. Epub Jan. 27, 2003.

Stingl et al., Purification and unique properties of mammary epithelial stem cells. Nature. Feb. 23, 2006;439(7079):993-7. Epub Jan. 4, 2006.

Todaro et al., Colon cancer stem cells dictate tumor growth and resist cell death by production of interleukin-4. Cell Stem Cell. Oct. 11, 2007;1(4):389-402. doi: 10.1016/j.stem.2007.08.001.

Trempus et al., Comprehensive microarray transcriptome profiling of CD34-enriched mouse keratinocyte stem cells. J Invest Dermatol. Dec. 2007;127(12):2904-7. Epub Jun. 21, 2007.

Trempus et al., Enrichment for living murine keratinocytes from the hair follicle bulge with the cell surface marker CD34. J Invest Dermatol. Apr. 2003;120(4):501-11.

(56) References Cited

OTHER PUBLICATIONS

Tumbar et al., Defining the epithelial stem cell niche in skin. Science. Jan. 16, 2004;303(5656):359-63. Epub Dec. 11, 2003.

Tusher et al., Significance analysis of microarrays applied to the ionizing radiation response. Proc Natl Acad Sci U S A. Apr. 24, 2001;98(9):5116-21. Epub Apr. 17, 2001. Erratum in: Proc Natl Acad Sci U S A Aug. 28, 2001;98(18):10515.

Van De Wetering et al., The beta-catenin/TCF-4 complex imposes a crypt progenitor phenotype on colorectal cancer cells. Cell. Oct. 18, 2002;111(2):241-50.

Van Der Flier et al., The Intestinal Wnt/TCF Signature. Gastroenterology. Feb. 2007;132(2):628-32. Epub Aug. 18, 2006.

Van Schoore et al., Expression pattern of the orphan receptor LGR4/GPR48 gene in the mouse. Histochem Cell Biol. Jul. 2005;124(1):35-50. Epub Jul. 19, 2005.

Wang et al., Expression and endocytosis of VEGF and its receptors in human colonic vascular endothelial cells. Am J Physiol Gastrointest Liver Physiol. Jun. 2002;282(6):G1088-96.

Wielenga et al., Expression of CD44 in Apc and Tcf mutant mice implies regulation by the WNT pathway. Am J Pathol. Feb. 1999;154(2):515-23.

Winton et al., Stem-cell organization in mouse small intestine. Proc Biol Sci. Jul. 23, 1990;241(1300):13-8.

Woo et al., SnapShot: hair follicle stem cells. Cell. Jul. 22, 2011;146(2):334-334.e2. doi: 10.1016/j.cell.2011.07.001.

Yamamoto et al., Overexpression of orphan G-protein-coupled receptor, Gpr49, in human hepatocellular carcinomas with beta-catenin mutations. Hepatology. Mar. 2003;37(3):528-33.

Yatabe et al., Investigating stem cells in human colon by using methylation patterns. Proc Natl Acad Sci U S A. Sep. 11, 2001;98(19):10839-44. Epub Aug. 21, 2001.

Yen et al., The gastrointestinal tract stem cell niche. Stem Cell Rev. 2006;2(3):203-12.

* cited by examiner

Fig.10

A

B

A

7 Day Virgin

B

110 Day Pregnant

| Samples | Fluorescent mean |
|---|---|
| L8 Rat 9G5 hLGR5.fcs | 2057.3 |
| Dox L8 Rat 9G5 hLGR5.fcs | 1213.85 |
| L8 Rat IgG hLGR5.fcs | 440.73 |
| Dox L8 Rat IgG hLGR5.fcs | 237.50 |

Figure 27

LGR5:

NR 2F10 LC (light chain)
GACATTCAGATGACGCAGTCTCCTTCACTACTGTCTGCATCTGTGGGAGACAG
AGTCACTCTCAACTGCAAAGCAGGT*CAGAATATCAACAATTAT*TTAGCCTGGT
ATCAGCAAAAGCTTGGGGCAGCTCCCAAAGTCCTGATATTT*TATGCAAAC*AGT
TTGCAAACGGGCATCCATCAAGGTTCAGTGGCAGTGGATCTGGTACAGATT
ACACACTCACCATCAGCAGCCTGCAGCCTGAAGATGTTGCCACATATTTCTGC
*CAGCAGTATTACATTTGGACCACG*TTTGGAGCTGGGACCAAGGTGGAACTGA
AACGGGCTGATGCTGCACCAACTGTATCTATCTTCCCACCATCCACGGAACA
GTTAGCAACTGGAGGTGCCTCAGTCGTGTGCCTCATGAACAACTTCTATCCC

LGR6:

OL 6d8 HC (heavy chain)
GATGTGCAACTGGTGGAGTCTGGGGGAGGCCTAGTGCAGCCTGGAAGGTCTC
TGAAACTATCCTGTGTAGCCTCT*GGATTCACATTCAATAACTACTGG*ATGACCT
GGATCCGCCAGGCTCCAGGGAAGGGGCTGGAGTGGGTTGCATCC*ATTACTAA
TACTGGTGGAAACACT*TACTATCCAGACTCTGTGAAGGGCCGATTCACTATCT
CCAGAGATAATGCAATAAGTACCCTGTACCTGCAAATGAACAGCCTGACGTC
TGAGGACACGGCCACGTATTACTGT*ACAAGCGAGGGAGGGAGTGGGCTTGAT
TAT*TGGGGCCAAGGAGTCATGGTCACTGTCTCTGCAGCCAAAACGACACCCC
C

OL 2F4 HC (heavy chain)
GAGGTGCAGCTTCAGGAGTCTGGACCTGGCCTTGTGAAACCCTCACAGTCAC
TCTCCCTCACCTGTTCTGTCACT*GGTTACTCCATCACTAAGAATTAC*TGGGGCT
GGATCCGGAAGTTCCCAGGAAATAAAATGGAGTGGATGGGATAC*ATAAGCCA
CAGTGGTAGTATT*AAGTACAATACATCTCAAAAGTCGAATCTCCATTACTA
GAGACACTTCGAAGAATCAGTTCTTCCTGCAGTTGAACTCTCTAACTACTGAG
GACACAGCCACATATTACTGT*GCAAGTCAAACTACCCGAGGTTTTGCTTAC*TG
GGGCCAGGGCACTCTGGTCACTGTCTCTGCAGCCAAAACGACACCCCC

METHOD FOR IDENTIFYING, EXPANDING, AND REMOVING ADULT STEM CELLS AND CANCER STEM CELLS

RELATED APPLICATIONS

This application is a divisional of U.S. patent application Ser. No. 14/494,511, filed Sep. 23, 2014, now U.S. Pat. No. 9,833,496, which is a continuation of U.S. patent application Ser. No. 14/705,336, filed May 10, 2010, now U.S. Pat. No. 8,906,631, which is a continuation of International Application No. PCT/NL2008/050543, filed Aug. 8, 2008, which was published under PCT Article 21(2) in English and which claims priority to European Application No. 07114192.3, filed Aug. 10, 2007, the entire contents of all of which are incorporated by reference herein.

The invention relates to the fields of biochemistry, pharmacy and oncology. The invention particularly relates to the use of novel stem cell markers for the isolation of stem cells. The invention further relates to the obtained stem cells and their use in for example research or treatment, for example, for the preparation of a medicament for the treatment of damaged or diseased tissue. The invention further relates to means suitable for cancer treatment and even more specific for the treatment of cancer stem cells.

Adult Stem Cells (Reviewed in 1)

Adult stem cells are found in many, if not all, organs of adult humans and mice. Although there may be great variation in the exact characteristics of adult stem cells in individual tissues, adult stem cells share the following characteristics: They retain an undifferentiated phenotype; their offspring can differentiate towards all lineages present in the pertinent tissue; they retain self-maintenance capabilities throughout life; and they are able to regenerate the pertinent tissue after injury. Stem cells reside in a specialized location, the stem cell niche. The niche typically supplies the appropriate cell-cell contacts and signals to maintain "stemness".

Some tissues display a high level of steady-state turnover. Good examples are the hematopoietic system, the skin, and the intestinal epithelium. It is assumed that stem cells in such tissues continuously contribute to the self-renewal process. Other muscles, such as the brain, the myocardium or the skeletal muscle, show very little if any proliferative activity in steady-state situations. Stem cells in such tissues are most likely dormant and only become active when differentiated cells are lost, for instance upon injury.

Bone marrow stem cells have been the subject of intensive research over the last 30 years. Work on other adult stem cells has typically been initiated more recently. Good progress has been made with a limited number of these, i.e. the epidermal stem cell, the hair follicle stem cell, neuronal stem cells, and the mammary gland stem cell. In a dramatic demonstration, a single mammary gland stem cell was shown to regenerate the entire mammary epithelium upon introduction into the mammary fat pad (2).

The study of stem cells has two prerequisites:
1) It has to be possible to recognize and isolate live primary stem cells. The availability of specific (combinations of) markers is essential. As exemplified by the seminal studies in human and mouse bone marrow, combinations of cell surface markers allow the sorting of strongly enriched populations of cells.
2) In vitro cell culture or in vivo transplantation assays subsequently allow the demonstration of long-term generation of all differentiated cell types. Typically, from these assay systems, stem cells are re-isolated and serially assayed to demonstrate long-term stemness and self-renewal.

As a non-limiting example of adult stem cells, intestinal stem cells are discussed in more detail.

Intestinal Stem Cells

The intestinal epithelium is the most rapidly self-renewing tissue in the adult. A handful of stem cells are believed to be located at the base of each intestinal crypt to ensure continuous and unlimited renewal. Compared to the other rapidly self-renewing tissues, the intestinal stem cells have remained rather elusive. No ex vivo or transplantation assays exist for these cells, and all knowledge of intestinal stem cells derives from histological analysis of crypts in situ. Intestinal stem cells divide slower than their proliferating descendants that fill the upward positions of the crypt. While the consensus is that colon stem cells are positioned at the bottom of the crypts, the localization of stem cells in the small intestine remains a controversial issue. Potten and colleagues have provided evidence supporting a localization immediately above the Paneth cell compartment at position +4, using the Long Term DNA label Retention assay (reviewed in 3,4). Lineage tracing studies have instigated Bjerknes and Cheng to propose that a different cell-type, the so called crypt base columnar cell, may represent the genuine stem cell. These crypt base columnar cells are intermingled with Paneth cells at the bottom-most positions of the crypts (5).

Only recently some candidate gene markers for intestinal stem cells have been proposed: i.e. Musashi (6,7) and phospho-PTEN (8). We and others find that the Musashi expression domain contains 30-50 cells per crypt, many more than there are stem cells (see below), while the phospho-PTEN mark may represent an artifact (9).

The number of stem cells in adult crypts has been estimated between 1 and 6 depending on the experimental approach used (10). It remains a matter of debate whether stemness is a set of properties that are self-perpetuated by asymmetric division through the years or whether the crypt bottom acts as a niche that confers these properties to progenitors residing within. The study of cell pedigrees in single crypts by analysis of methylation tags (11) indicates that stem cells divide stochastically in asymmetric (i.e. one daughter stem cell plus one differentiating progenitor) or symmetric fashion (i.e. either two stem cells daughters or two differentiating progenitors). Of note, while the existence of asymmetric and symmetric cell divisions is inferred from the above studies, no formal proof of asymmetric distribution of determinants during mitosis in the intestinal epithelium has been observed so far.

When they reach the top third of colorectal crypts (or the villus in the small intestine), committed progenitors differentiate into absorbtive cells (colonocytes/enterocytes) or secretory lineage cells (goblet cells, enteroendocrine cells, Paneth cells). From this point onwards, differentiated cells continue their migration towards the villus in coherent bands stretching along the crypt-villus axis or organised at the surface epithelium of the colorectum in clusters of hexagonal appearance. As an exception to this rule, Paneth cells migrate towards the crypt bottom in the small intestine (reviewed in 12).

Cancer Stem Cells (Reviewed in 13, 14)

The cancer stem cell hypothesis postulates that a small reservoir of self-sustaining cells is exclusively able to self-renew and maintain the tumor. These cancer stem cells can expand the cancer stem cell pool, but will also generate the heterogeneous cell types that constitute the bulk of the tumor. Cancer stem cells may be relatively refractory to therapies that have been developed to eradicate the rapidly dividing cells that constitute the bulk of a tumor. Cancer stem cells may also be the most likely cells to metastasize. Thus, the cancer stem cell hypothesis would require that we rethink the way we diagnose and treat tumors. Therapy would have to target the "minority" stem cell population that fuels tumor growth and metastasis, rather than the bulk of the tumor. The cancer stem cell hypothesis is at the centre of a rapidly evolving field and may dictate changes in how basic and clinical researchers view cancer.

In the 1990s, studies by John Dick and others on acute myelogenous leukemia (AML) supported the existence of cancer stem cells in this disease (15, 16). Efforts to define the cell of origin in hematopoietic malignancies were greatly helped by the availability of heamatopoietic lineage maps, and of cell surface markers for distinct cell types and lineages. The putative AML stem cells were demonstrated to be capable of regenerating human AML in irradiated NOD/SCID mice. The AML stem cell displayed a $CD34^+CD38^-$ phenotype, similar to that of normal human hematopoietic progenitors, suggesting a close similarity between AML stem cells and normal stem cells.

Recently, cancer stem cells have also been identified in a number of solid tumors. Clarke and colleagues transplanted fractioned cells from human breast tumors into NOD/SCID mice. As few as a hundred $CD44^+CD24^-$/low cells could establish tumors in mice, whereas tens of thousands of cells from different fractions failed to induce tumors (17). This example has been followed by multiple other studies on solid tumors. For instance, brain tumor stem cells that can produce serially transplantable brain tumors in NOD/SCID mice have been isolated from human medulloblastomas and glioblastomas using the CD133 marker found also on normal neural stem cells (reviewed in 18). Sorting for Hoechst dye-excluding side population (SP) cells and for CD44 allowed the isolation of cancer stem cells in prostate cancer (reviewed in 19).

There is some confusion in the literature as to the definition of a cancer stem cell. Here, we follow the consensus reached at a recent AACR workshop (14), which states that the cancer stem cell "is a cell within a tumor that possesses the capacity to self-renew and to cause the heterogeneous lineages of cancer cells that comprise the tumor. Cancer stem cells can thus only be defined experimentally by their ability to recapitulate the generation of a continuously growing tumor". Alternative terms in the literature include tumor-initiating cell and tumorigenic cell. Assays for cancer stem cell activity need to address the potential of self-renewal and of tumor propagation. The gold-standard assay currently is serial xeno-transplantation into immunodeficient mice.

As a non-limiting example of cancer stem cells, colon cancer stem cells are discussed in more detail.
Colon Cancer Stem Cells Can the cancer stem cell hypothesis be extrapolated to human colon cancer? Two very recent studies imply that this is the case. John Dick and colleagues explored the usefulness of CD133 as a marker for colorectal cancer cells (20). CD133 or Prominin, is a marker that is associated with stem and progenitor populations in multiple tissues and cancers. They found that CD133 was expressed on 5-20% of human colon cancer cells. Subsequent serial xenograft assays demonstrated that CD133+, but not CD133− cells could initiate tumor formation in immunodeficient mice. It was calculated that the frequency of cancer stem cells in the isolated CD133+ population was slightly less than 0.5%. Along similar lines, De Maria and colleagues found that CD133+ cells comprised less than 2.5% of human colon cancer cells and also demonstrated that these cells could be serially transplanted into immunodeficient mice (21). Moreover, the CD133+ cells could be maintained for long periods of time in culture using a serum-free medium containing EGF and FGF2.

These studies imply that colon cancer may represent another example of a solid tumor in which a small number of cancer stem cells is responsible for maintenance of the tumor. Sorting for expression of the CD133 marker enriches significantly for the cancer stem cell, but the resulting cell mixture remains far from pure. It therefore remains unclear what the exact properties are of the cancer stem cells within the sorted cell preparation, such as their cell cycle status, or their resistance to chemotherapy or radiation.

US 2004/0058392 and EP 1 400 807 describe a list of TCF target genes that were defined in the colon cancer cell line Ls174T (22). In the applications, it was speculated that these molecules expressed in colon cancer cells and in intestinal crypts would represent stem cell markers. Several of the markers encode cell-surface proteins. The inventors of US 2004/0058392 and EP 1 400 807 contemplated that these proteins can be used as markers for selection of the abundant stem cell population in the gut. However, it turned out that the overwhelming majority of these proteins are not suitable as a stem cell selection marker as they are not expressed (specifically) by stem cells. E.g. the CD44 protein is expressed by all dividing crypt cells (23) as is cMyb (24) and GPX2 (25). The c-Kit protein is expressed on non-dividing entero-endocrine cells (26). EphB2 is expressed by all dividing cells and EphB3 is expressed by the non-dividing Paneth cells (27). BMP4 is expressed by stromal cells in the villus (28). And Claudin1 is expressed almost ubiquitously (29).

The present invention provides markers that identify adult and/or tissue stem cells and cancer stem cells. The identified adult and/or tissue stem cells are useful in the repair of damaged or diseased tissue. The present invention further provides methods that allow for the isolation of adult and/or tissue stem cells and/or cancer stem cells. The invention further provides ex vivo methods for culturing or maintaining or multiplying (isolated) adult and/or tissue stem cells and/or cancer stem cells. The invention yet further provides methods that allow the identification and eradication of cancer stem cell markers. One of the objects of the present invention is to provide novel markers that are useful in a method for identifying adult stem cells and cancer stem cells. Another object of the present invention is to provide a method suitable for maintaining/culturing/multiplying/expanding adult stem cells. Yet another object of the present invention is to eradicate cancer stem cells. Adult stem cells are typically isolated from tissue and are therefore also referred to as tissue stem cells.

Figure 10:
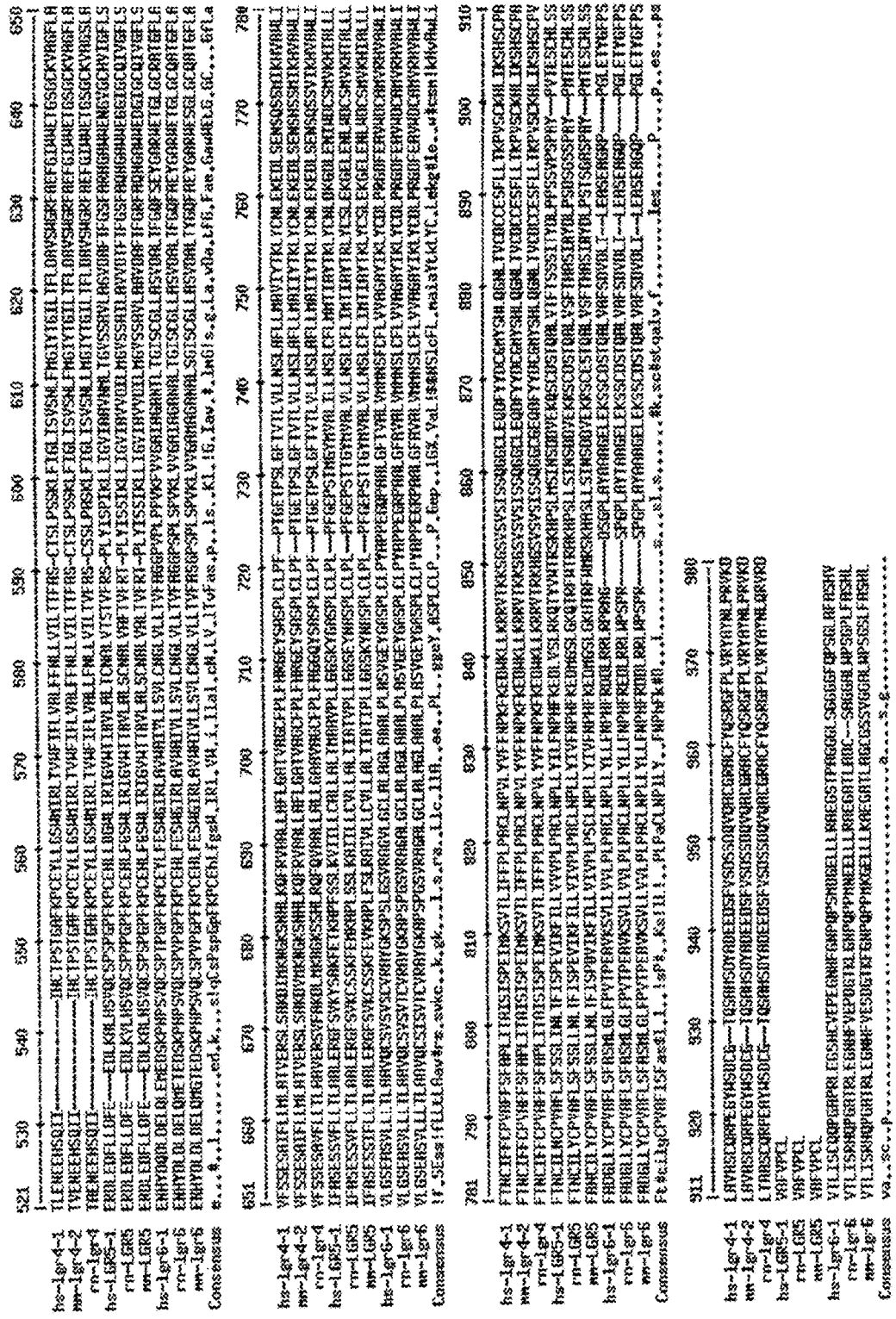

The surface receptors Lgr5 and Lgr 6 mark adult stem cells in multiple tissues as well as cancer stem cells in multiple types of cancer. The present inventors disclose that the expression patterns of the surface molecules Lgr5 (also known as Grp49) and of Lgr6 independently mark adult stem cells in multiple tissues, as well as cancer stem cells in multiple types of cancer. Glycoprotein hormone receptors, such as the receptors for LH, FSH, and TSH, belong to the large G protein-coupled receptor (GPCR) superfamily, but are unique in carrying a large leucine-rich ectodomain important for ligand binding. These leucine-rich repeat-containing, G protein-coupled receptors in the human genome are termed LGRs. Phylogenetic analysis shows that there are three LGR subgroups: the known glycoprotein hormone receptors; LGR4 to 6; and a third subgroup represented by LGR7 (30). LGR5 and -6 are the main subject of this invention. Ligands for these two receptors remain not described in the scientific literature; hence these receptors are often referred to as orphans. Sequences of the human, mouse and rat receptors are shown in FIG. 10. Human LGR4 comprises 951 amino acids, 447 of which are identical to the corresponding amino acids in LGR5 and 485 of which are identical to the corresponding amino acids in LGR6. Human LGR5 comprises 907 amino acids, 387 of which are identical to the corresponding amino acids in LGR6. LGR6 consists of 967 amino acids. A predicted structure of these receptors is given in FIG. 11. LGR4/GPR48 is the best studied gene of the three. According to the scientific literature, it is broadly expressed in multiple tissues (31, 32) and not associated specifically with stem cells. In genetic mouse models, it has been described to be important for intrauterine growth (32), for male fertility (33) and for renal development (34). LGR5/GPR49 has been knocked out. Mutant embryos die after birth due to a defect in the tongue and lower jaw (35). LGR5/GPR49 is overexpressed in hepatic and colon cancers (22, 36, 37). LGR6 has not been studied beyond its initial cloning and sequence analysis (30).

In a first embodiment, the invention provides a method for obtaining (or isolating) adult stem cells comprising
optionally preparing a cell suspension from a normal tissue or organ sample
contacting said cell suspension with an Lgr5 and/or 6 binding compound
identify the cells bound to said binding compound
optionally isolating the stem cells from said binding compound.

A method of the invention allows obtaining (or isolating) a collection of cells comprising, preferably consisting of, at least 50%, more preferred at least 60%, more preferred at least 70%, more preferred at least 80%, most preferred at least 90% stem cells, such as between 90% and 99% stem cells or between 95% and 99% stem cells, the method comprising
optionally preparing a cell suspension from a normal tissue or organ sample
contacting said cell suspension with an Lgr6 and/or 5 binding compound
identify or obtaining cells bound to said binding compound
optionally isolating the stem cells from said binding compound.

The isolated collection of stem cells comprises, and preferably consists of, more than 50%, more preferred at least 60%, more preferred at least 70%, more preferred at least 80%, most preferred at least 90% stem cells, such as between 90% and 99% stem cells or between 95% and 99% pure pluripotent stem cells, which can retain an undifferentiated phenotype. The cells retain self-maintenance capabilities throughout life; and are able to regenerate the pertinent tissue after injury. Their offspring, or non-stem cell daughter cells, can differentiate towards all lineages present in the pertinent tissue. Said collection of cells can be isolated from a cell suspension comprising stem cells and non-stem cell daughter cells such as committed or differentiated daughter progenitor cells. An adult stem cell is preferably a stem cell obtained from a post embryonic tissue. Preferably a post natal tissue. In primates such as a human they are preferably obtained from at least a year old subject, preferably a post-puberal subject. In a preferred embodiment of the invention said stem cells are adult stem cells and/or cancer stem cells.

A major advantage of a collection of stem cells comprising more than 50% pluripotent stem cells is that said population comprises less cells that can act negatively on the self maintenance capacity of the stem cells and/or the differentiation capacity of the stem cells, compared to a collection of stem cells comprising less than 50% pure pluripotent stem cells. These negatively acting cells comprise non-stem cell daughter cells or other non-stem cells that are co-isolated with the stem cells.

Further advantages of a pure, or almost pure, population of adult stem cells are that limited cell numbers can be used as therapeutic agent for the treatment of diseases in which the corresponding tissue has been affected, of which the composition is well known.

Preferably, said stem cells are tissue stem cells, such as for instance intestinal stem cells, skin stem cells or retina stem cells. The invention preferably provides a method for isolating tissue stem cells, said method comprising the above described steps. Said stem cells do not include human embryonic stem cells. When isolating adult and/or tissue stem cells it is preferred to start with a collection of cells from the specific tissue from which the tissue and/or adult stem cell is to be isolated. Typically a tissue stem cell and/or adult stem cell is committed to form cells of said tissue, however, a tissue and/or adult stem cell can exceptionally be manipulated to produce cells of another tissue.

Stem cells are primal cells found in all multi-cellular organisms. They retain the ability to renew themselves through mitotic cell division and can differentiate into a diverse range of specialized cell types. The three broad categories of mammalian stem cells are: embryonic cells (derived from blastocysts), adult stem cells (which are found in adult tissues) and cord blood stem cells (which are found in the umbilical cord). The definition of a stem cell requires that it is at least capable of self-renewal (the ability to go through numerous cycles of cell division while maintaining the undifferentiated state) and has an unlimited potency (the capacity to differentiate into any mature cell type, i.e. being either totipotent, pluripotent, multipotent or unipotent).

In a preferred embodiment, the invention provides a method for obtaining (or isolating) stem cells comprising
optionally preparing a cell suspension from a normal tissue sample
contacting said cell suspension with an Lgr 5 and/or 6 binding compound
identify or obtaining the cells bound to said binding compound
optionally isolating the stem cells from said binding compound, wherein said stem cells are adult stem cells, more preferably mammalian adult stem cells and even more preferably human adult stem cells. These adult stem cells typically act as a repair system for the body and are replenishing specialized cells. Adult stem cells are found in children as well as in adults and most adult stem cells are lineage restricted (multipotent) and are referred to by their tissue origin, for example skin stem cell or retina stem cell.

A tissue or organ sample can be obtained via any known method, such as a biopsy. Moreover, a tissue or organ sample can be obtained from any possible tissue or organ, such as, but not limited to, heart, retina, breast, ovary, lung, brain, eye, stomach, pancreas, liver, intestine comprising colon and rectal tissue, skin, hair follicle, and adrenal medulla, The phrase "a normal tissue or organ sample" is used herein to refer to a tissue or organ sample which is healthy, non-transformed, non-malignant, non-cancerous or non-tumorigenic, i.e. a healthy, non-transformed, non-malignant, non-cancerous or non-tumorigenic tissue or organ sample. Any pathologist, skilled in the art, can determine if a tissue is healthy non-transformed, non-malignant, non-cancerous, or non-tumorigenic.

In a preferred embodiment, the used tissue or organ sample is of mammalian human origin. Even more preferably, the tissue is adult tissue (i.e. tissue of a borne mammal, i.e. non-embryonic/fetal tissue).

Bone marrow and (cord) blood can be considered natural cell suspensions. From solid organs, cell suspensions can be obtained for instance by mechanical disruption of organ tissue into small fragments. These fragments can then optionally be further segregated into single cells by chemicals such as EDTA and/or by enzymatic digestion with for instance the enzyme preparations trypsin, dispase, collagenase or pancreatin. The procedure can involve tissue or cell culture before, during or after the disruption and/or enzymatic digestion procedures As it is not always necessary to isolate the stem cells from the used binding compound, said step is presented as an optional feature in the claim. When it is necessary to isolate the stem cells from the Lgr 5 and/or 6 binding compound, this can be performed by multiple methods well known to the skilled person. Suitable examples are (mechanical) agitation, enzymatic digestion, addition of excess binding compound or a derivative thereof, elution by changing pH or salt concentration.

Now that the inventors have provided evidence that Lgr5 or 6 are (unique) markers for stem cells, compounds that are capable of binding to Lgr5 and/or 6 (i.e. Lgr5 or 6 binding compounds) can be used to identify, mark and isolate stem cells.

One suitable example of an Lgr5 or 6 binding compound is an antibody or an antibody derivative or an antibody fragment capable of binding to Lgr5 or 6, i.e. an antibody or derivative or fragment thereof that has affinity for Lgr5 or 6. As Lgr5 and 6 are transmembrane surface proteins, such an antibody or a derivative or a fragment thereof preferably has affinity for the part of the protein facing externally, i.e. binds to any extracellular part. In a preferred embodiment, said antibody or an antibody derivative or an antibody fragment has a high affinity for Lgr5 and/or 6.

Hence, in a preferred embodiment, the invention provides a method for obtaining (or isolating) stem cells comprising
optionally preparing a cell suspension from a normal tissue or organ sample
contacting said cell suspension with an Lgr5 and/or 6 binding compound
identify or obtaining the cells bound to said binding compound
optionally isolating the stem cells from said binding compound, wherein said Lgr5 and/or 6 binding compound is an antibody or an antibody derivative or an antibody fragment capable of binding to Lgr5 and/or 6.

Antibodies or their derivatives and/or their fragments can be provided by methods that are well known to the person skilled in the art and include the hybridoma technology in normal or transgenic mice or in rabbits, or phage display antibody technology. In one embodiment, genetic immunization is used. This technique comprises administration of a nucleic acid sequence, or a functional equivalent thereof, encoding at least one antigen of interest, to a non-human animal. The encoded antigen(s) is/are produced by the animal, which stimulates the animal's immune system against said antigen(s). Hence, an immune response against said antigen(s) is elicited in said animal. Subsequently, T-cells, B-cells and/or antibodies specific for an antigen of interest are preferably obtained from said animal. Said T-cells, B-cells and/or antibodies are optionally further processed. In one preferred embodiment, an obtained B-cell of interest is used in hybridoma technology wherein said obtained B-cell is fused with a tumor cell in order to produce a hybrid antibody producing cell.

Examples of suitable antibody fragments are scFv, Fab, or (Fab)2 fragments. Examples of suitable derivatives are chimeric antibodies, nanobodies, bifunctional antibodies or humanized antibodies.

In yet another preferred embodiment, the used antibody is a monoclonal antibody.

In a further preferred embodiment, a Lgr5 and/or 6 binding compound comprises an antibody or an antibody derivative or an antibody fragment comprising a heavy chain CDR1, CDR2 and/or CDR3 sequence as depicted in FIG. 27, and preferably also comprising a complementary immunoglobulin light chain molecule, whereby the CDR sequences are determined according to Kabat (Kabat et al., "Sequences of Proteins of Immunological Interest," U.S. Dept. of Health and Human Services, National Institute of Health, 1987). Preferably, said antibody or antibody derivative or antibody fragment comprises the heavy chain CDR1 sequence and the heavy chain CDR2 sequence and the heavy chain CDR3 sequence of a heavy chain as depicted in FIG. 27. It was found by the inventors that an antibody or an antibody derivative or an antibody fragment, such as for example a scFv, Fab, or (Fab)2 fragment, comprising a heavy chain CDR1, CDR2 and/or CDR3 sequence as depicted in FIG. 27 constitutes a high affinity binding compound with a high specificity for their target proteins.

In a further preferred embodiment, a Lgr5 and/or 6 binding compound comprises an antibody or an antibody derivative or an antibody fragment comprising a light chain CDR1, CDR2 and/or CDR3 sequence as depicted in FIG. 27, and preferably also comprising a complementary immunoglobulin heavy chain molecule, whereby the CDR sequences are determined according to Kabat (Kabat et al., "Sequences of Proteins of Immunological Interest," U.S. Dept. of Health and Human Services, National Institute of Health, 1987). Preferably, said antibody or antibody derivative or antibody fragment comprises the light chain CDR1 sequence and the light chain CDR2 sequence and the light chain CDR3 sequence of the light chain as depicted in FIG. 27. It was found by the inventors that an antibody or an antibody derivative or an antibody fragment, such as for example a scFv, Fab, or (Fab)2 fragment, comprising a light chain CDR1, CDR2 and/or CDR3 sequence as depicted in FIG. 27 constitutes a high affinity binding compound with a high specificity for their target proteins.

In one preferred embodiment, a Lgr5 and/or 6 binding compound comprises an antibody as depicted in Table 4 or 5.

A method according to the invention, wherein an antibody as depicted in Table 4 or 5 is used is therefore also herewith provided, as well as a method according to the invention, wherein an antibody or an antibody derivative or an antibody fragment is used which comprises at least one CDR sequence as depicted in FIG. 27. Preferably, said antibody or antibody derivative or antibody fragment comprises a CDR1 sequence and a CDR2 sequence and a CDR3 sequence of a light chain and/or heavy chain depicted in FIG. 27.

In a specific embodiment, a binding compound comprising a heavy chain and/or a light chain CDR1, CDR2 and/or CDR3 sequence as depicted in FIG. 27, is a rat monoclonal antibody. In preferred embodiment, a binding compound comprising a heavy chain and/or a light chain CDR1, CDR2 and/or CDR3 sequence as depicted in FIG. 27, is a chimaeric, deimmunized, or humanized monoclonal antibody. Methods for generating a chimaeric, deimmunized, or humanized monoclonal antibody or derivative or fragment thereof comprising a heavy chain and/or a light chain CDR1, CDR2 and/or CDR3 sequence as depicted in FIG. 27, are known in the art. For example, a chimaeric antibody can be generated comprising a rodent variable region comprising the indicated CDR sequence(s) fused to a non-rodent, for example a human, constant region (Morrison et al. 1984. Proc Natl Acad Sci USA 81: 6851-6855; which is hereby incorporated by reference). Methods for deimmunization of a binding compound comprising a heavy chain and/or a light chain CDR1, CDR2 and/or CDR3 sequence as depicted in FIG. 27 are also known to a skilled person, for example from Giovannoni, 2003. Neurology 61: S13-S17; which is hereby incorporated by reference. Humanization of a non-human antibody is principally achieved through grafting of the CDR regions to a human immunoglobulin framework region as is shown, for example, in U.S. Pat. Nos. 6,548,640, 5,530,101, and 5,859,205, which are all hereby incorporated by reference.

A human antibody against Lgr5 or 6 can also be generated in an animal provided with human sequences encoding an immunoglobulin heavy and/or light chain gene such as transgenic strains of mice in which mouse antibody gene expression is suppressed and effectively replaced with human antibody gene expression. Examples are provided by the HuMAb®-Mouse technology of Medarex; the TC Mouse™ technology of Kirin, and the KM-Mouse® technology, a crossbred mouse that combines the characteristics of the HuMAb-Mouse with the TC Mouse.

The invention further provides the use of a binding compound according to the invention for identifying or isolating stem cells from a population of cells comprising stem cells and committed or differentiated daughter progenitor cells; whereby the isolated stem cells comprise at least 50% pure pluripotent stem cells.

Another example of an Lgr5 or 6 binding compound is an Lgr5 or 6 ligand. Such an Lgr5 or 6 ligand can be used unmodified, can be produced and/or used as a fusion protein (i.e. a ligand fusion protein) or can be coupled to a second moiety to, for example, allow cell separation.

In a preferred embodiment, the invention therefore provides a method for obtaining (or isolating) stem cells comprising
optionally preparing a cell suspension from a normal tissue or organ sample
contacting said cell suspension with an Lgr5 and/or 6 binding compound
identify or obtaining the cells bound to said binding compound
optionally isolating the stem cells from said binding compound, wherein said Lgr5 and/or 6 binding compound is a Lgr5 or 6 ligand, for example a ligand fusion protein.

The person skilled in the art is very well capable of producing an Lgr5 or 6 ligand fusion protein, for example via standard molecular biology techniques.

A suitable example of an Lgr5 or 6 ligand is a member of the insulin peptide family, such as Ins15 or relaxin3. Another suitable example is a cysteine-knot protein such as Noggin, Gremlin1 or -2, Dan, or Cerberus. The nucleotide and amino acid sequences of these ligands are known and the skilled person is thus for example capable to produce a ligand fusion protein.

Preferably the second moiety of a ligand fusion protein introduces a feature which allows for easy identification and tracing of the fusion protein, for example a protein (fragment) such as the antibody Fc tail or Staphylococcal protein A or Glutathion-S-transferase, a short antigenic peptide tag such as the Myc, FLAG or HA tag or an oligomeric Histidine-tag, an enzymatic tag such as Alkaline Phosphatase, a fluorescent protein tag such as Green Fluorescent Protein. Small chemical moieties can also be coupled to the ligand for stem cell identification and/or isolation. These moieties can be recognized and bound by specific antibodies, or can have specific affinity for a material to be used in cell separation, or can for instance be fluorescent. In an even more preferred embodiment, the second part of the fusion protein is linked to an Lgr5 or 6 ligand via a spacer. Even more preferable, said spacer comprises an enzyme digestible sequence. This allows for an easy separation of the second moiety and the Lgr5 or 6 ligand.

Yet another example of an Lgr5 or 6 binding compound is a small compound that has affinity for Lgr5 or 6.

In a preferred embodiment, the invention thus provide a method for obtaining (or isolating) stem cells comprising
optionally preparing a cell suspension from a normal tissue or organ sample
contacting said cell suspension with an Lgr5 and/or 6 binding compound
identify or obtaining the cells bound to said binding compound
optionally isolating the stem cells from said binding compound,
wherein said Lgr5 or 6 binding compound is a small molecule with affinity for Lgr5 or 6. A suitable example is a small chemical molecule or a small non-chemical molecule or a small protein.

In a preferred embodiment, the affinity of said small molecule for Lgr5 or 6 is a high affinity, i.e. an affinity with a Kd of at least $10^{-7}$.

As already outlined above, the invention provides a method for obtaining (or isolating) stem cells comprising
optionally preparing a cell suspension from a normal tissue or organ sample
contacting said cell suspension with an Lgr5 and/or 6 binding compound
identify or obtaining the cells bound to said binding compound
optionally isolating the stem cells from said binding compound,
wherein said cells are preferably (adult) (tissue) stem cells.

Non-limiting examples of stem cells that can be obtained via the above mentioned methods are skin, intestinal comprising colon and rectal, eye, retina, brain, breast, hair follicle, pancreas, stomach, liver, lung, heart, adrenal medulla, or ovarian stem cells. It has not been previously been possible to obtain or isolate stomach, intestinal or retina stem cells. Hence, in a preferred embodiment, the obtained or isolated stem cells are stomach, intestinal or retina stem cells.

Depending on the desired adult and/or tissue stem cell and the presence or absence of Lgr5 and/or 6, a method according to the invention can be performed with at least one, at least two, at least three or even more (different) binding compound(s). Table 1 provides an overview of the presence or absence of Lgr5 or 6 on different kind of adult and/or tissue stem cells. Based on Table 1 the person skilled in the art is very well capable of selecting one or multiple target markers and one or multiple corresponding binding compounds and to obtain or isolate stem cells from a particular normal tissue or organ.

TABLE 1

The distribution of the adult and/or tissue stem cell markers Lgr5 and 6

| stem cell | marker | |
|---|---|---|
| | Lgr5 | Lgr6 |
| brain | + | + |
| kidney | − | − |
| liver | + | − |
| lung | − | + |
| retina | + | − |
| stomach | + | − |
| intestine | + | − |
| pancreas | + | − |
| testis | − | − |
| breast | + | + |
| hair follicle | + | + |
| heart | − | + |
| ovary | + | − |
| adrenal medulla | + | − |
| skin | + | + |
| bladder | + | − |
| bone | + | − |
| connective tissue | + | + |
| ear | + | − |
| muscle | + | − |
| prostate | + | − |
| placenta | + | − |
| uterus | + | + |
| bone marrow | − | + |
| eye | − | + |

If the person skilled in the art wants, for example, to obtain breast stem cells, a binding compound of Lgr5 or 6 can be used alone or in any combination thereof, because the breast stem cells comprise both of said markers.

In a preferred embodiment, the invention provides a method for obtaining (or isolating) stem cells comprising
optionally preparing a cell suspension from a normal tissue or organ sample
contacting said cell suspension with an Lgr5 and/or 6 binding compound
identify or obtaining the cells bound to said binding compound
optionally isolating the stem cells from said binding compound,
wherein
said Lgr5 and/or 6 binding compound is an Lgr5 binding compound and wherein said stem cells are brain, liver, retina, stomach, intestine, pancreas, ovary, hair follicle, adrenal medulla, skin, bladder, bone, ear, muscle, prostate, placenta, or breast stem cells; or
said Lgr5 and/or 6 binding compound is an Lgr6 binding compound and wherein said stem cells are brain, skin, lung, breast, hair follicle, bone marrow, eye, or heart stem cells; or
said Lgr5 and/or 6 binding compound is at least one Lgr6 binding compound in combination with at least one Lgr5 binding compound and wherein said stem cells are brain, breast, skin, connective tissue, uterus, or hair follicle stem cells.

In yet another preferred embodiment, the invention provides a method for obtaining (or isolating) stem cells comprising
optionally preparing a cell suspension from a normal tissue or organ sample
contacting said cell suspension with an Lgr5 and/or 6 binding compound
identify or obtaining the cells bound to said binding compound
optionally isolating the stem cells from said binding compound,
wherein said stem cell is any of the stem cells identified in Table 1 and wherein the used Lgr5 and/or 6 binding compound corresponds to the desired stem cell as shown in Table 1, with the proviso that in case the stem cell is an intestinal or hair follicle cell, the Lgr5 or 6 binding compound is not uniquely targeting Lgr5 (i.e. is not a Lgr5 binding compound alone).

In a preferred embodiment, the invention provides a method for obtaining (or isolating) stem cells comprising
optionally preparing a cell suspension from a normal tissue or organ sample
contacting said cell suspension with an Lgr5 and/or 6 binding compound
identify or obtaining the cells bound to said binding compound
optionally isolating the stem cells from said binding compound,
wherein one binding compound is used.

In yet another preferred embodiment, the invention provides a method for obtaining (or isolating) stem cells comprising
optionally preparing a cell suspension from a normal tissue or organ sample
contacting said cell suspension with an Lgr5 and/or 6 binding compound
identify or obtaining the cells bound to said binding compound
optionally isolating the stem cells from said binding compound,
wherein at least two different binding compounds are contacted with said cell suspension. Said two different binding compounds can be directed against one and the same marker (i.e. directed to Lgr5 or to Lgr6). For example use can be made of two antibodies directed to two different epitopes which antibodies together provide (a preferably essentially complete) capture of the desired stem cells. However, said two different binding compounds can also be directed to two different stem cell markers (i.e. one binding compound for Lgr5 and one for Lgr6). Whenever use is made of two or three or even more binding compounds, said binding compounds may be from the same class of binding compounds (for example all being antibodies, small molecules or ligand fusion proteins) or may be from different classes of binding compounds (for example an antibody directed to Lgr6 and a ligand fusion protein for binding to Lgr5).

In a preferred embodiment, at least two different antibodies or antibody derivatives or antibody fragments capable of binding to Lgr5 or 6 are contacted with a cell suspension.

After allowing the binding compounds to interact with the cell suspension (for a certain amount of time or under different conditions such as pH, temperature, salt etc.), subsequent identification of obtained bound complexes is performed. This is for example accomplished by using FACS analysis. Fluorescence-activated cell-sorting (FACS) is a specialised type of flow cytometry. It provides a method for sorting a heterogeneous mixture of biological cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

In a preferred embodiment, the invention provides a method for obtaining (or isolating) stem cells comprising optionally preparing a cell suspension from a normal tissue or organ sample contacting said cell suspension with an Lgr5 and/or 6 binding compound identify or obtaining the cells bound to said binding compound optionally isolating the stem cells from said binding compound, wherein a FACS is used to identify and sort the cells that bind to an Lgr5 or 6 binding compound.

Other options for isolation of stem cells utilizes binding compounds bound to Lgr5 or 6 on stem cells in conjunction with magnetic bead sorting, immunoaffinity column cell separation or panning.

For analysis by FACS, the binding compound is provided with a fluorescence label, for analysis by magnetic bead sorting the binding compound is provide with magnetic beads (for example an antibody-coated magnetic bead), for immunoaffinity it is bound to a solid support, for panning to tissue culture dishes.

Now that we know that Lgr5 and/or 6 are markers for adult stem cells, this knowledge can also be used in respect of the culturing of adult stem cells. Ligands of Lgr5 and/or 6 as well as small molecule agonists of Lgr5 and/or 6 can be used as a stimulator for the growth of normal (i.e. healthy, non-transformed, normal) adult stem cells.

The invention therefore also provides a method for maintaining or culturing tissue or organ stem cells, comprising providing tissue or organ stem cells with an Lgr5 and/or 6 ligand or a small molecule agonist of Lgr5 and/or 6.

The term "maintaining" is used herein to describe the situation in which the number of stem cells is essentially not changed. The term "culturing" is used herein to describe the situation in which the amount of stem cells is increased, i.e. in which the cells are expanded while retaining their stem cell phenotype.

After the tissue or organ stem cells have been provided with an Lgr5 and/or 6 ligand, the cells are incubated in tissue culture at circumstances (temperature, culture medium, pH) that allow for maintenance or expansion.

The stem cells can be obtained via any suitable method but are preferably obtained by any of the methods described herein, i.e. a method for obtaining (or isolating) stem cells comprising optionally preparing a cell suspension from a normal tissue or organ sample contacting said cell suspension with an Lgr5 and/or 6 binding compound identify or obtaining the cells bound to said binding compound optionally isolating the stem cells from said binding compound.

In a preferred embodiment, the invention provides a method for maintaining or culturing tissue or organ stem cells, comprising providing tissue stem cells with an Lgr5 and/or 6 ligand or a small molecule agonist of Lgr5 and/or 6, wherein said ligand is a member of the insulin peptide family. A suitable example of an Lgr5 or 6 ligand is a member of the insulin peptide family, such as Ins15 or relaxin3. Another suitable example is a cysteine-knot protein such as Noggin, Gremlin 1 or 2, Dan, or Cerberus.

The invention further provides (isolated) stem cells, or a collection of isolated stem cells, preferably from mammalian origin or even more preferably human adult stem cells, wherein at least 50% of the cells are Lgr5 or 6 positive, pluripotent stem cells. Preferably, at least 60% of the cells are Lgr5 or 6 positive, pluripotent stem cells. More preferably, at least 70% of the cells are Lgr5 or 6 positive, pluripotent stem cells. More preferably, at least 80% of the cells are Lgr5 or 6 positive, pluripotent stem cells. More preferably, at least 90% of the cells are Lgr5 or 6 positive, pluripotent stem cells. Most preferably, at least 95% of the cells are Lgr5 or 6 positive, pluripotent stem cells. The purity of the collection can be increased as indicated herein above. In a preferred embodiment the invention provides (isolated) stem cells or a collection of isolated stem cells wherein said stem cells contain bound specific Lgr5 and/or Lgr6 binding compound. Preferably a specific Lgr5 and/or Lgr6 binding antibody as described herein above or a fragment or derivative thereof. The invention further provides a culture of stem cells comprising a binding antibody specific for Lgr5 and/or Lgr6 or a specific fragment of at least 20 amino acids of said Lgr5 and/or Lgr6 binding antibody.

In a preferred embodiment, said stem cells are, or said collection of stem cells comprises, brain, liver, retina, stomach, intestine including colon and rectal, ovary, hair follicle, adrenal medulla, skin, bladder, bone, connective tissue, ear, muscle, prostate, placenta, uterus, or breast stem cells that comprise Lgr5 in their cell membrane.

In a particularly preferred embodiment, said stem cells are, or said collection of stem cells comprises, brain, lung, skin, breast, hair follicle, connective tissue, uterus, bone marrow, eye, or heart stem cells that comprise Lgr6 in their cell membrane.

In a further preferred embodiment, said stem cells are, or said collection of stem cells comprises, brain, breast, skin, connective tissue, uterus, or hair follicle stem cells that comprise Lgr5 as well as Lgr6 in their cell membrane.

In yet another embodiment, the invention provides stem cells, or a collection of stem cells wherein at least 50%, preferably at least 60%, more preferably at least 70%, more preferably at least 80%, more preferably at least 90%, more preferably at least 95% of the cells are Lgr5 or 6 positive, pluripotent stem cells, obtainable by a method according to the invention, i.e.

(i) a method for obtaining (or isolating) stem cells comprising optionally preparing a cell suspension from a normal tissue or organ sample contacting said cell suspension with an Lgr5 and/or 6 binding compound identify or obtaining the cells bound to said binding compound optionally isolating the stem cells from said binding compound, and/or (ii) a method for maintaining or culturing tissue stem cells, comprising providing tissue stem cells with an Lgr5 and/or 6 ligand or a small molecule agonist of Lgr5 and/or 6.

The stem cells, or the collection of stem cells, isolated according to the invention can be used as a therapeutic agent for the treatment of diseases in which the corresponding tissue has been affected. However, the obtained stem cells are also very useful for other purposes.

In yet another useful embodiment, the invention provides the use of stem cells, or a collection of stem cells, as obtained by any of the herein described methods, in the preparation of a medicament for treating damaged or diseased tissue.

Preferably said stem cells are human stem cells. Even more preferably the acceptor is human as well. Table 2 provides an overview of different stem cells and the diseases in which they can therapeutically be used.

TABLE 2

Therapeutic applications for use of Lgr5+ and/or Lgr6+ stem cells

| stem cell | Therapeutic application |
| --- | --- |
| brain | Brain damage such as stroke and traumatic brain injury. Degenerative diseases such as Alzheimer's, Parkinson, Huntington's |
| kidney | Chronic or acute kidney failure |
| liver | Chronic liver failure, for instance due to damage by infectious agents, chemicals including alcohol or metabolic disorders |
| lung | COPD, fibrosis |
| retina | Blindness and vision impairments due to defects in the retina |
| stomach | Pernicious anemia |
| Intestinal, colon, rectal, and colorectal | Crohn's disease, tissue damage resulting from chemotherapy or other toxic agents, |
| pancreas | Diabetes |
| testis | Sterility |
| breast | Breast reconstruction |
| hair follicle | Baldness |
| heart | Heart disease such as congestive heart failure |
| ovary | Sterility |
| Skin | Skin grafting |
| Adrenal medulla | Addison's Disease |

Hence, the invention provides a use of stem cells, or a collection of stem cells, as obtained by any of the herein described methods, in the preparation of a medicament for treating damaged or diseased tissue,
wherein said stem cells are intestinal stem cells and wherein said tissue is damage to the intestinal epithelium, damage to the liver or damage to the pancreas or
wherein said stem cells are retina stem cells and wherein tissue damage is damaged retina; such an approach is useful in the treatment of blindness due to defects in the retina; or
wherein said stem cells are brain stem cells; or
wherein said stem cells are breast stem cells; or
wherein said stem cells are hair follicle stem cells and the damages tissue are hair follicles; such an approach is extremely useful in the treatment of baldness and involves isolating of follicle stem cells by the herein described method, multiplying the obtained stem cells and implanting the new follicles into the scalp; or
wherein said stem cells are stomach stem cells; or
wherein said stem cells are liver stem cells; or
wherein said stem cells are ovarian stem cells; or
wherein said stem cells are skin stem cells for providing skin grafts; or
wherein said stem cells are any of the cells mentioned in Table 2 and the disease to be treated is mentioned as the corresponding therapeutic application in Table 2, for example the stem cells are retina stem cells and the disease is blindness due to defects in the retina.

Gene therapy can additionally be used in a method directed at repairing damaged or diseased tissue. Use can, for example, be made of an adenoviral or retroviral gene delivery vehicle to deliver genetic information (like DNA and/or RNA) to stem cells. A skilled person can replace or repair particular genes targeted in gene therapy. For example, a normal gene may be inserted into a nonspecific location within the genome to replace a nonfunctional gene. This approach is common. In yet another example, an abnormal gene could be swapped for a normal gene through homologous recombination or an abnormal gene could be repaired through selective reverse mutation, which returns the gene to its normal function. A further example is altering the regulation (the degree to which a gene is turned on or off) of a particular gene. Preferably, the stem cells are ex vivo treated by a gene therapy approach and are subsequently transferred to the mammal (preferably a human being) in need of treatment.

Thus, the invention also provides a method for modifying a genomic sequence of a stem cell, comprising providing a collection of stem cells according to a method of the invention, contacting said collection with a nucleic acid to modify a genomic sequence, and isolating a stem cell in which a genomic sequence has been modified. The invention further provides a method for modifying a genomic sequence of a tissue cell comprising providing a collection of tissue cells in vitro with a nucleic acid sequence for modifying said genomic sequence, further comprising isolating a stem cell from said collection of tissue cells according to a method of the invention.

The invention further provides isolated, genomicly modified stem cells obtainable by a method of the invention, and wherein at least 50%, preferably at least 60%, more preferably at least 70%, more preferably at least 80%, more preferably at least 90%, more preferably at least 95% of the cells are pluripotent stem cells which can retain an undifferentiated phenotype. The invention further provides isolated, genomicly modified stem cells obtainable by a method of the invention, and wherein at least 50%, preferably at least 60%, more preferably at least 70%, more preferably at least 80%, more preferably at least 90%, more preferably at least 95% of the cells are adult and/or tissue stem cells as defined herein.

In yet another useful embodiment, the invention provides the use of stem cells as obtained by any of the herein described methods, in the preparation of a medicament for treating damaged or diseased tissue, further comprising genetically modifying said stem cells preferably ex vivo and/or preferably by a gene therapy approach. The invention further provides a composition for treating tissue or organ damage comprising isolated genomicly modified stem cells according to the invention.

In yet an alternative embodiment, the invention provides a composition for treating tissue damage comprising tissue stem cells obtainable by a method according to the invention, i.e.

(i) a method for obtaining (or isolating) stem cells comprising
optionally preparing a cell suspension from a tissue or organ sample
contacting said cell suspension with an Lgr5 and/or 6 binding compound
identify or obtaining the cells bound to said binding compound
optionally isolating the stem cells from said binding compound, and/or
(ii) a method for maintaining or culturing tissue stem cells, comprising providing tissue stem cells with an Lgr5 and/or 6 ligand or a small molecule agonist of Lgr5 and/or 6.

Stem cells of the invention are also very useful for research purposes. Examples of suitable research purposes are further identification of stem cell markers or the development of gene therapy with the stem cells of the invention as a target or any other research purpose.

The invention further provides a use of Lgr5 and/or 6 as a marker for the isolation of tissue stem cells as well as the use of an Lgr5 and/or 6 binding compound for the isolation of tissue stem cells.

The invention further provides a method for treating an individual in need thereof comprising administering to said individual a sufficient amount of stem cells obtainable/obtained by a method according to the invention.

In a further embodiment, the invention provides a recombinant animal comprising a first reporter gene under control of a Lgr5 or Lgr6 promoter such that the reporter gene product is expressed in cells expressing Lgr5 or Lgr6, a sequence encoding a regulatable protein being in an operable linkage with the first reporter gene such that the regulatable protein is co-expressed with the first reporter gene product in cells expressing Lgr5 or Lgr6, and a second reporter gene that is expressed upon activation of the regulatable protein.

A recombinant animal of the invention allows staining of tissue or organ stem cells with said first reporter, and allows staining of non-stem cells daughter cells such as committed or differentiated daughter progenitor cells with the second reporter gene product after activation of the regulatable protein.

A reporter gene is a gene that encodes a product that can readily be assayed. Reporter genes are typically used to determine whether a particular nucleic acid construct has been successfully introduced into a cell, organ or tissue and/or to specifically detect the cell in which the reporter gene has been introduced and is expressed. The expression product is typically unique in the sense that non modified cells or cells that do not express the reporter gene are not specifically detected. A reporter gene is also referred to as a marker gene. When two or more reporter genes are used, the different reporter genes are typically not the same, in the sense that their expression products can easily be distinguished from each other. Thus a first and a second reporter gene are typically not the same. A regulatable protein as used herein is a protein that, upon the presence of a signal, alters its function. Many different regulatable proteins have been identified and/or artificially generated. A well known example is the tet-repressor system where the presence or absence of tetracycline or an analogue thereof regulates the activity of the tet-operon by regulating the binding capacity of the tet-repressor protein to the tet-repressor binding sequence. In this example the tet-repressor protein is the regulatable protein and the presence or absence of tetracycline is the signal. Although the tet-repressor system is well known, there are many other regulatable proteins.

Co expression of two or more proteins in a cell is currently very common. Fusion proteins can be generated. Preferably a multi-cistron is used. This is currently typically achieved using at least one so-called internal ribosomal entry site (IRES). Alternative methods include the use of reinitiation sites and/or alternative splicing of an RNA containing two or more open reading frames.

The invention also provides a recombinant stem cell comprising a first reporter gene under control of a Lgr5 or Lgr6 promoter such that the reporter gene product is expressed in cells expressing Lgr5 or Lgr6, a sequence encoding a regulatable protein being in an operable linkage with the first reporter gene such that the regulatable protein is co-expressed with the first reporter gene product in cells expressing Lgr5 or Lgr6, and a second reporter gene that is expressed upon activation of the regulatable protein.

Said stem cell can be generated from an isolated stem cell, or preferably is isolated from a recombinant animal according to the invention.

Said regulatable protein preferably is CRE-ERT2, which can be activated by administration of an estrogen or analogue thereof such as tamoxifen or 4-hydroxytamoxifen. In this preferred embodiment, the expression of the second reporter gene is regulated by activated CRE-ERT2 through the removal of a repressor sequence that prevents expression of the second reporter gene in the inactive state. In a preferred embodiment, said first reporter gene product is a fluorescent protein such as green fluorescent protein, or more preferred enhanced green fluorescent protein. In a further preferred embodiment, said second reporter gene comprises LacZ, encoding beta-galactosidase which can be identified through provision of a suitable substrate such as X-gal. Said second reporter gene is preferably inserted into a genomic region that provides robust, prolonged expression of the transgene after activation, such as the ROSA locus if the transgenic animal is a mouse.

In a preferred embodiment the invention provides a recombinant animal comprising the nucleic acids as specified in the examples in the context of the recombinant animal for tracing stem cells described therein.

In a preferred embodiment said recombinant animal is a non-human animal. Preferably a mammal, more preferably a rodent. More preferably a rat or a mouse.

The invention further provides the use of a recombinant animal or a recombinant stem cell according to the invention for tracing stem cells and descendants of a stem cell.

The invention also provides a method for identifying descendants of a stem cell, comprising providing a recombinant animal or recombinant stem cell according to the invention, activating the regulatable protein, and identifying cells that do not express Lgr5 and/or 6 and the first reporter, and express the second reporter protein.

The present inventors disclose that the expression of Lgr5 (also known as Grp49) as well as the expression of Lgr6 not only mark adult stem cells, but also mark cancer stem cells in multiple different tumors.

In yet another embodiment, the invention provides a method for obtaining (or isolating) cancer stem cells comprising optionally preparing a cell suspension from a solid or liquid tumor sample contacting said cell suspension with an Lgr5 and/or 6 binding compound identify or obtaining the cells bound to said binding compound optionally isolating the cancer stem cells from said binding compound.

Preferably said cancer stem cells are involved in intestinal cancer, including colon, rectal and colorectal cancer, skin cancer such as basal cell carcinoma, esophageal cancer, breast cancer, prostate cancer, medulloblastoma and other brain cancers, liver cancer, stomach cancer, retina, head and neck cancer, testicular cancer, hair follicle, ovarian cancer, adrenal medulla cancer (pheochromocytoma) or lung cancer. Thus, in a preferred embodiment, said cancer stem cells are intestinal cancer stem cells, including colon-, rectal- and colorectal cancer stem cells, skin cancer stem cells such as basal cell carcinoma stem cells, esophageal cancer stem cells, breast cancer stem cells, prostate cancer stem cells, medulloblastoma stem cells and other brain cancer stem cells, liver cancer stem cells, stomach cancer stem cells, retina stem cells, head and neck cancer stem cells, testicular cancer stem cells, hair follicle cancer stem cells, ovarian cancer stem cells, pheochromocytoma stem cells, or lung cancer stem cells.

As mentioned, there is some confusion in the literature as to the definition of a cancer stem cell. Herein, we follow the consensus reached at a recent AACR workshop (14), which states that the cancer stem cell "is a cell within a tumor that possesses the capacity to self-renew and to cause the heterogeneous lineages of cancer cells that comprise the tumor.

Cancer stem cells can thus only be defined experimentally by their ability to recapitulate the generation of a continuously growing tumor". Alternative terms in the literature include tumor-initiating cell and tumorigenic cell. Assays for cancer stem cell activity preferably need to address the potential of self-renewal and of tumor propagation. The gold-standard assay currently is serial xeno-transplantation into immunodeficient mice.

A solid tumor sample is for example obtained via biopsy or surgical techniques and a liquid tumor sample is for example obtained by taking a blood, urine, cerebrospinal fluid or lymph sample from a mammal, preferably a human.

The tissue or organ that is sampled is for example the colon, a breast, prostate, brain, liver, stomach or lung.

For information in respect of Lgr5 or 6, the earlier parts of this application can be considered.

In a preferred embodiment, the invention provides a method for obtaining (or isolating) cancer stem cells, or a collection of cancer stem cells, comprising optionally preparing a cell suspension from a solid or liquid tumor sample contacting said cell suspension with an Lgr5 and/or 6 binding compound identify or obtaining the cells bound to said binding compound optionally isolating the cancer stem cells from said binding compound, wherein said cancer stem cells are mammalian, preferably human, cancer stem cells, and wherein the collection of cancer stem cells comprises at least 50% cancer stem cells that are able to recapitulate the generation of a continuously growing tumor. In a preferred embodiment said collection of cancer stem cells comprises at least 60% cancer stem cells, preferably at least 70% cancer stem cells, more preferably 80% cancer stem cells, more preferably 90% cancer stem cells, more preferably 95% cancer stem cells that are able to recapitulate the generation of a continuously growing tumor.

Bone marrow and (cord) blood can be considered natural cell suspensions. From solid tumors, cell suspensions can be obtained for instance by mechanical disruption of organ tissue into small fragments. These fragments can then optionally be further segregated into single cells by chemicals such as EDTA and/or by enzymatic digestion with for instance the enzyme preparations dispase, collagenase or pancreatin. The procedure can involve tissue or cell culture before, during or after the disruption and/or enzymatic digestion procedures.

When a cell suspension is already available this step of the method can be omitted (optional feature).

As it is not always necessary to isolate the cancer stem cells from the used binding compound, said step is presented as an optional feature in the claim. When it is necessary to isolate the cancer stem cells from the Lgr5 or 6 binding compound, this can be performed by multiple methods well known to the skilled person. Suitable examples are (mechanical) agitation, enzymatic digestion, addition of excess binding compound or a derivative thereof, elution by changing pH or salt concentration.

Now that the inventors have shown that Lgr5 or 6 are markers for cancer stem cells, compounds that are capable of binding to Lgr5 or 6 (i.e. Lgr5 or 6 binding compounds) can be used to identify, mark and isolate cancer stem cells.

One suitable example of an Lgr5 or 6 binding compound is an antibody or an antibody derivative or an antibody fragment capable of binding to Lgr5 or 6, i.e. an antibody or derivative or fragment thereof that has affinity for Lgr5 or 6. As Lgr5 and 6 are transmembrane surface proteins, such an antibody or a derivative or a fragment thereof preferably has affinity for the part of the protein facing externally, i.e. binds to any extracellular part of said protein.

In a preferred embodiment, said antibody or an antibody derivative or an antibody fragment has a high affinity for Lgr5 and/or 6, i.e. an affinity with a Kd of at least $10^{-7}$. Preferably the affinity is $\leq 10^{-9}$. However, affinities of around $10^{-8}$ can also be used.

Hence, in a preferred embodiment, the invention provides a method for obtaining (or isolating) cancer stem cells comprising optionally preparing a cell suspension from a solid or liquid tumor sample contacting said cell suspension with an Lgr5 and/or 6 binding compound identify or obtaining the cells bound to said binding compound optionally isolating the cancer stem cells from said binding compound, wherein said Lgr5 or 6 binding compound is an antibody or an antibody derivative or an antibody fragment capable of binding to Lgr5 or 6.

Antibodies or their derivatives or their fragments can be provided by methods that are well known to the person skilled in the art and include the hybridoma technique, single chain-antibody/phage display technology.

As non-limiting examples, the experimental part describes Lgr5-specific and Lgr6-specific antibodies. A method according to the invention, wherein an antibody as depicted in Table 4 or 5 is used is therefore also herewith provided, as well as a method according to the invention, wherein an antibody or an antibody derivative or an antibody fragment is used which comprises at least one CDR sequence as depicted in FIG. 27. Preferably, said antibody or antibody derivative or antibody fragment comprises a CDR1 sequence and a CDR2 sequence and a CDR3 sequence of a light chain and/or heavy chain depicted in FIG. 27.

Examples of suitable antibody fragments are scFv, Fab. Examples of suitable derivatives are chimeric antibodies, nanobodies, bifunctional antibodies or humanized antibodies. In yet another preferred embodiment, the used antibody is a monoclonal antibody.

Another example of an Lgr5 or 6 binding compound is an Lgr5 or 6 ligand which can be used unmodified, but can also be produced and/or used as a fusion protein or can be coupled to a second moiety to allow cell separation.

In a preferred embodiment, the invention therefore provides a method for obtaining (or isolating) cancer stem cells comprising optionally preparing a cell suspension from a solid or liquid tumor sample contacting said cell suspension with an Lgr5 and/or 6 binding compound identify or obtaining the cells bound to said binding compound optionally isolating the cancer stem cells from said binding compound, wherein said Lgr5 or 6 binding compound is an Lgr5 or 6 ligand.

The person skilled in the art is very well capable of producing an Lgr5 or 6 ligand fusion protein, for example via standard molecular biology techniques.

A suitable example of an Lgr5 or 6 ligand is a member of the insulin peptide family, such as Ins15 or relaxin3. Another suitable example is a cysteine-knot protein such as Noggin, Gremlin, Dan, or Cerberus. Based on the known and published nucleotide and amino acid sequences of these ligands, the preparation of a fusion protein is well within the abilities of the person skilled in the art.

Preferably the second moiety introduces a feature which allows for easy identification and tracing of the fusion protein, for example a protein (fragment) such as the antibody Fc tail or Staphylococcal protein A or Glutathion-S-transferase, a short antigenic peptide tag such as the Myc, FLAG or HA tag or an oligomeric Histidine-tag, an enzymatic tag such as Alkaline Phosphatase, a fluorescent protein tag (such as Green Fluorescent Protein). Small chemical moieties can also be coupled to the ligand for cancer stem cell identification and/or isolation. These moieties can be recognized and bound by specific antibodies, or can have specific affinity for a material to be used in cell separation, or can for instance be fluorescent, radioactive or magnetic properties. In an even more preferred embodiment, the second part of the fusion protein is linked to said Lgr5 or 6 ligand via a spacer. Even more preferable, said spacer comprises an enzyme digestible sequence. This allows for an easy separation of the second moiety and the Lgr5 or 6 ligand.

Yet another example of an Lgr5 or 6 binding compound is a small compound that has affinity for Lgr5 or 6.

In a preferred embodiment, the invention thus provide a method for obtaining (or isolating) cancer stem cells comprising optionally preparing a cell suspension from a solid or liquid tumor sample contacting said cell suspension with an Lgr5 and/or 6 binding compound identify or obtaining the cells bound to said binding compound optionally isolating the cancer stem cells from said binding compound, wherein said Lgr5 and/or 6 binding compound a small molecule with affinity for Lgr5 and/or 6. Such a small molecule is for example a synthetic peptide or a small chemical compound.

In a preferred embodiment, the affinity of said small molecule for Lgr5 or 6 is a high, i.e. an affinity with a Kd of at least $10^{-7}$.

Such a small molecule is optionally coupled to a second moiety that introduces a feature which allows for easy identification and tracing of the fusion protein, for example a protein (fragment) such as the antibody Fc tail or Staphylococcal protein A or Glutathion-S-transferase, a short antigenic peptide tag such as the Myc, FLAG or HA tag or an oligomeric Histidine-tag, an enzymatic tag such as Alkaline Phosphatase, a fluorescent protein tag such as Green Fluorescent Protein).

Depending on the desired cancer stem cell and the now known presence or absence of Lgr5 or 6, a method according to the invention can use at least one, at least two, at least three or even more (different) binding compound(s). Table 3 provides an overview of the presence of absence of Lgr5 or 6 on the different kind of tumors. Based on this Table the person skilled in the art is very well capable of selecting one or multiple target markers and one or multiple corresponding binding compounds and thus capable of obtaining or isolating cancer stem cells.

TABLE 3

The distribution of the stem cell markers Lgr5 and 6 in tumors. Data is derived from comparison of Lgr5 or Lgr6 expression in normal versus tumor tissues by microarray analysis (Genelogic) or by quantitative PCR.

| Cancer stem cell | Marker | |
|---|---|---|
| | Lgr5 | Lgr6 |
| brain | + | + |
| kidney | − | − |
| liver | + | − |
| lung | − | + |
| retina | + | − |
| stomach | + | − |
| Colon/rectal | + | + |
| head and neck | + | + |
| testis | + | + |
| breast | + | + |
| hair follicle | + | + |
| prostate | + | + |
| ovary | + | + |
| skin | + | + |
| leukemia | + | − |
| chondrosarcoma | + | + |
| muscle/soft tissue | + | − |
| uterus | + | + |
| retinoblastoma | − | + |

If the person skilled in the art wants to obtain breast cancer stem cells, a binding compound of Lgr5 or 6 can be used alone or in any combination thereof, because the breast cancer stem cells comprise both of said markers.

In a preferred embodiment, the invention provides a method for obtaining (or isolating) cancer stem cells comprising optionally preparing a cell suspension from a solid or liquid tumor sample contacting said cell suspension with an Lgr5 and/or 6 binding compound identify or obtaining the cells bound to said binding compound optionally isolating the cancer stem cells from said binding compound, wherein
    said Lgr5 or 6 binding compound is an Lgr5 binding compound and wherein said cancer stem cells are brain, liver, retina, stomach, colon, head and/or neck, testis, prostate, ovary, skin, hair follicle, leukemia, chondrosarcoma, muscle/soft tissue, uterus, or breast stem cells; or
    said Lgr5 or 6 binding compound is an Lgr6 binding compound and wherein said cancer stem cells are brain, lung, head and/or neck, testis, breast, hair follicle, skin, prostate, chondrosarcoma, uterus, retinoblastoma, or ovary stem cells; or
    said Lgr5 or 6 binding compound is at least one Lgr6 binding compound in combination with at least one Lgr5 binding compound and wherein said cancer stem cells are brain, skin, head and/or neck, testis, breast, prostate, ovary, chondrosarcoma, uterus, or hair follicle stem cells.

In a preferred embodiment, the invention provides a method for obtaining (or isolating) cancer stem cells comprising optionally preparing a cell suspension from a solid or liquid tumor sample contacting said cell suspension with an Lgr5 and/or 6 binding compound identify or obtaining the cells bound to said binding compound
optionally isolating the cancer stem cells from said binding compound,
wherein one binding compound is used.

In yet another preferred embodiment, the invention provides a method for obtaining (or isolating) cancer stem cells comprising
optionally preparing a cell suspension from a solid or liquid tumor sample
contacting said cell suspension with an Lgr5 and/or 6 binding compound
identify or obtaining the cells bound to said binding compound
optionally isolating the cancer stem cells from said binding compound,
wherein at least two different binding compounds are contacted with said cell suspension. Said two different binding compounds can be directed against one and the same marker (for example directed to Lgr5). For example, use can be made of two antibodies directed to two different epitopes which antibodies together provide (a preferably essentially complete) capture of the desired stem cells. However, said two different binding compounds can also be directed to two different stem cell markers (for example to Lgr6 and Lgr5). Whenever use is made of two or three or even more binding compounds, said binding compounds may be from the same class of binding compounds (for example all being antibodies, small molecules or ligand (fusion proteins)) or may be from different classes of binding compounds (for example an antibody directed to Lgr6 and a ligand fusion protein for binding to Lgr5).

In a preferred embodiment, at least two different antibodies or antibody derivatives or antibody fragments capable of binding to Lgr5 and/or 6 are contacted with a cell suspension.

After allowing the binding compounds to interact with the cell suspension (for a certain amount of time or under different conditions such as pH, temperature, salt etc.), subsequent identification of obtained bound complexes is performed. This is for example accomplished by using FACS analysis. Fluorescence-activated cell-sorting (FACS) is a specialised type of flow cytometry. It provides a method for sorting a heterogenous mixture of biological cells into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

In a preferred embodiment, the invention provides a method for obtaining (or isolating) cancer stem cells, or a collection of cancer stem cells, comprising
optionally preparing a cell suspension from a solid or liquid tumor sample
contacting said cell suspension with an Lgr5 and/or 6 binding compound
identify or obtaining the cells bound to said binding compound
optionally isolating the cancer stem cells from said binding compound,
wherein a FACS is used to identify and sort the cells that bind to an Lgr5 and/or 6 binding compound, and wherein said collection comprises at least 50% of cancer stem cells that are able to recapitulate the generation of a continuously growing tumor. Preferably, said collection comprises at least 60%, more preferably at least 70%, more preferably at least 80%, more preferably at least 90%, more preferably at least 95% of cancer stem cells that are able to recapitulate the generation of a continuously growing tumor.

Other options for identification of bound complexes are magnetic bead sorting, (immuno)affinity column cell separation, or (immuno)affinity panning.

For analysis by FACS, the binding compound is preferably provided with a fluorescence label, for analysis by magnetic bead sorting the binding compound is preferably provided with magnetic beads (for example an antibody-coated magnetic bead).

In yet another embodiment, the invention provides (a collection of) cancer stem cells comprising Lgr5 and/or 6 embedded in their cell membrane, wherein said collection comprises at least 50% of cancer stem cells that are able to recapitulate the generation of a continuously growing tumor. In a preferred embodiment said collection comprises at least 60% pure cancer stem cells, preferably at least 70% pure cancer stem cells, more preferably at least 80% pure cancer stem cells, more preferably at least 90% pure cancer stem cells, more preferably at least 95% pure cancer stem cells. More preferably said collection consists of (cancer) stem cells with the indicated purity. Such a collection of cancer stem cells is for example obtained by a method as described herein, i.e. a method for obtaining (or isolating) cancer stem cells comprising
optionally preparing a cell suspension from a solid or liquid tumor sample
contacting said cell suspension with an Lgr5 and/or 6 binding compound
identify or obtaining the cells bound to said binding compound
optionally isolating the cancer stem cells from said binding compound.

Examples of cancer stem cells that can be obtained via the above mentioned methods are colon, rectal, intestine, skin, retina, brain, breast, testis, hair follicle, stomach, head and/or neck, liver, lung, prostate, esophagus, adrenal medulla, heart, or ovarian cancer stem cells.

If necessary, said cancer stem cells are maintained or multiplied (expanded) by culturing said cells in the presence of an Lgr5 and/or 6 ligand under appropriate environmental conditions (for example pH and temperature). A suitable example of an Lgr5 or 6 ligand is a member of the insulin peptide family, such as Ins15 or relaxin3. Another suitable example is a cysteine-knot protein such as Noggin, Gremlin, Dan, or Cerberus.

Hence, in yet another embodiment, the invention provides a method for maintaining or culturing cancer stem cells, comprising providing cancer stem cells with an Lgr5 and/or 6 ligand or a small binding molecule of Lgr5 or 6.

The invention further provides a collection of (isolated) cancer stem cells of the invention further comprising an Lgr5 and/or Lgr6 binding compound associated with Lgr5 and/or Lgr6 expressed by said cancer stem cells. The invention further provides a culture of (isolated) cancer stem cells comprising an Lgr5 and/or Lgr6 binding compound. Preferably said Lgr5 and/or Lgr6 binding compound is a specific Lgr5 and/or Lgr6 binding antibody or a fragment or derivative thereof.

In a preferred embodiment, the invention provides a recombinant tumor stem cell, isolated according to a method of the invention, comprising a reporter gene under control of a Lgr5 or Lgr6 promoter such that the reporter gene product is expressed in cells expressing Lgr5 or Lgr6. A reporter gene construct, in which the reporter gene is operably linked to a Lgr5 or Lgr6 promoter, can be inserted into the genome of an isolated tumor stem cell. Alternatively, said reporter gene construct can be provided, for example, through infection of a tumor stem cell with an adenoviral vector comprising the reporter gene construct. Methods for inserting a reporter gene construct into the genome of a cell are known to a skilled person and include random insertion, for example by insertion of a retrovirus comprising the reporter gene construct, or through homologous recombination.

In a further preferred embodiment, the invention provides a recombinant stem cell comprising a first reporter gene under control of a Lgr5 or Lgr6 promoter such that the reporter gene product is expressed in cells expressing Lgr5 or Lgr6, a sequence encoding a regulatable protein being in an operable linkage with the first reporter gene such that the regulatable protein is co-expressed with the first reporter gene product in cells expressing Lgr5 or Lgr6, and a second reporter gene that is expressed upon activation of the regulatable protein.

Said first reporter gene product preferably is a fluorescent protein such as green fluorescent protein, or more preferred enhanced green fluorescent protein. Said regulatable protein preferably is CRE-ERT2. The second reporter gene preferably comprises LacZ.

Isolated (and optionally cultured) cancer stem cells are for example useful for the further analysis of such cells on for example biochemical, molecular biology or marker level.

Moreover, isolated cancer stem cells are also very useful in the identification of compounds that can be used in cancer treatment, especially cancer stem cell therapy. Based on the knowledge that Lgr5 and/or 6 are embedded in the cell membrane of cancer stem cells, compounds capable of inhibiting, blocking or binding to Lgr5 and/or 6 can be designed and prepared. Such compounds can subsequently be tested for their ability to kill or functionally block or inhibit cancer stem cells comprising Lgr5 and/or 6 in their cell membrane.

Recombinant tumor stem cells according to the invention are particularly preferred for the identification of compounds, because their presence can readily be monitored after addition of a compound. Said recombinant tumor stem cells are suited for use in assays such a high throughput assays, where multiple compounds are tested in a cost-efficient manner.

In another embodiment, the invention thus provides a method for testing the effect of a possible anti cancer stem cell compound comprising contacting (treating) a set of cancer stem cells according to the invention in vitro with said possible anti cancer stem cell compound and testing whether said treated cancer stem cells are capable of generating a continuously growing tumor and wherein said possible cancer stem cell compound is preferably designed as an Lgr5 or 6 inhibitor or as an Lgr5 or 6 binding compound.

In yet another embodiment, the invention provides a method for testing the effect of a possible anti cancer stem cell compound comprising contacting a collection of cancer stem cells according to the invention in vitro with said possible anti cancer stem cell compound and testing whether said treated cancer stem cells are capable of generating a continuously growing tumor, further comprising contacting said possible anti cancer stem cell compound with a tissue of organ stem cell and selecting a compound that specifically effects tumour stem cells.

The cancer stem cells used in this method comprise Lgr5 and/or 6 in their cell membrane or are obtainable by a method for obtaining (or isolating) cancer stem cells comprising optionally preparing a cell suspension from a solid or liquid tumor sample contacting said cell suspension with an Lgr5 and/or 6 binding compound identify or obtaining the cells bound to said binding compound optionally isolating the cancer stem cells from said binding compound.

The to be tested compounds can for example be obtained from a (small) compound library or can be specifically designed based on the (structural) knowledge of Lgr5 or 6 or on the (structural) knowledge of a (natural) ligand of Lgr5 or 6.

The anti cancer stem cell compounds will be discussed in more detail below.

In yet a further embodiment, the invention provides an Lgr5 or 6 inhibitor or an Lgr5 or 6 binding compound. Preferably such an inhibitor or binding compound is obtainable by a method for testing the effect of a possible anti cancer stem cell compound comprising contacting (treating) a set of cancer stem cells according to the invention in vitro with said possible anti cancer stem cell compound and testing whether said treated cancer stem cells are capable of generating a continuously growing tumor and wherein said possible cancer stem cell compound is preferably, but nor necessarily, designed as an Lgr5 or 6 inhibitor or as an Lgr5 or 6 binding compound.

A first example of an Lgr5 or 6 inhibitor is an inhibitor of Lgr5 or 6 protein. Preferably said Lgr5 or 6 protein inhibitor is an antibody or antibody derivative or antibody fragment capable of binding to Lgr5 or 6 and more preferably capable of binding to the part of Lgr5 or 6 that is exposed on the outside of the cancer stem cell. In yet another preferred embodiment, said antibody or antibody derivative or antibody fragment binds to said Lgr5 or 6 protein and functionally blocks said Lgr5 or 6 protein by preventing the binding of a natural ligand of Lgr5 or 6. In one embodiment, said antibody or antibody derivative or antibody fragment comprises at least one CDR sequence as depicted in FIG. 27. Preferably, said antibody or antibody derivative or antibody fragment comprises a CDR1 sequence and a CDR2 sequence and a CDR3 sequence of a light chain and/or a heavy chain depicted in FIG. 27. In a further embodiment, said antibody is an antibody as depicted in Table 4 or 5.

Examples of suitable antibody fragments are scFv and Fab. Examples of suitable derivatives are chimeric antibodies, nanobodies, bifunctional antibodies or humanized antibodies.

In yet another preferred embodiment, the used antibody is a monoclonal antibody.

Another example of an Lgr5 or 6 protein inhibitor is a small molecule that interferes with the biological activity of Lgr5 or 6. Such a small molecule can be a chemical compound as well as a small protein and is typically designed on the basis of structure-function analysis of Lgr5 or 6. Analysis can comprise crystal structure analysis of Lgr5 or 6. Small molecules libraries can be screened or compounds can be designed and subsequently screened. A small molecule inhibitor can also be designed based on the structure of a (natural) ligand of Lgr5 or 6.

Yet another example of an Lgr5 or 6 inhibitor is an inhibitor of the mRNA transcripts of Lgr 5 or 6. One example of an inhibitor of Lgr5 or 6 transcript are antisense molecules. Antisense drugs are complementary strands of small segments of mRNA. Such an antisense molecule binds to the mRNA of Lgr5 or 6 and inhibits (at least in part) Lgr5 or 6 protein production. Another example of an inhibitor of Lgr5 or 6 transcript relate to RNA interference (RNAi) molecules such as siRNA molecules.

Besides the option that an antibody or antibody derivative or antibody fragment binds to Lgr5 or 6 and functionally blocks Lgr5 or 6 (as described above), said antibody or antibody derivative or antibody fragment can also bind to Lgr5 or 6 without functionally blocking the Lgr5 or 6 activity. Such an antibody or antibody derivative or antibody fragment is preferably coupled to another compound (i.e. another moiety) that is capable of functionally inhibiting a cancer stem cell. An example of such another compound is a toxin. Hence, the invention also provides a cancer stem cell inhibitor, wherein said inhibitor comprises a first part that is capable of binding to Lgr5 or 6 and a second part that provides for cancer stem cell dysfunction. Preferably, said first part is an antibody or antibody derivative or antibody fragment binds to Lgr5 or 6 (preferably without influencing the function of Lgr5 or 6) and said second part is a toxin. In this embodiment Lg5 or 6 is used as a target to deliver a cytotoxic compound to a cancer stem cell.

Thus, the invention also provides a binding compound according to the invention that is linked to a toxic agent or linked to an enzyme capable of converting a prodrug to a toxic agent. For example, the antibody or derivative or fragment thereof is linked to a toxic agent to form an immunoconjugate. Said toxic agent includes a radioisotope and a toxic drug which is ineffective when administered systemically alone. By combining the targeting-specificity of a binding compound of the invention to Lgr 5 and/or 6-expressing tumor stem cells with the killing power of a toxic effector molecule, immunoconjugates permit sensitive discrimination between target and normal tissue, resulting in fewer toxic side effects than most conventional chemotherapeutic drugs. Examples of prodrugs that can be targeted to Lgr 5 or 6-expressing tumor stem cells comprise benzoic acid mustard whereby the antibody is conjugated to carboxypeptidase G2; nitrogen mustardcephalosporin-p-phenylenediamine whereby the antibody is conjugated to beta-lactamase; and cyanophenylmethylbeta-D-glucopyranosiduronic acid, whereby the antibody is conjugated to beta-glucosidase.

The invention further provides a use of a binding compound according to the invention as a medicament for treatment of cancer. In a preferred embodiment said binding compound comprises an antibody specific for Lgr5 and/or Lgr6 or an Lgr5 or 6 binding fragment or derivative thereof. In a preferred embodiment said antibody is a human, humanized or deimmunised anti Lgr5 and/or Lgr6 antibody as described herein. In a preferred embodiment said binding compound is specific for human Lgr5 and/or human Lgr6. Preferably said antibody is a monoclonal antibody. In one embodiment, said binding compound is an antibody or antibody derivative or antibody fragment which comprises at least one CDR sequence as depicted in FIG. 27. Preferably, said antibody or antibody derivative or antibody fragment comprises a CDR1 sequence and a CDR2 sequence and a CDR3 sequence of a light chain and/or a heavy chain depicted in FIG. 27. In a further embodiment, said binding compound is an antibody as depicted in Table 4 or 5. In a preferred embodiment, a binding compound according to the invention is linked to a toxic agent or linked to an enzyme capable of converting a prodrug to a toxic agent.

In yet another embodiment, the invention provides a cancer stem cell inhibitor comprising an Lgr5 or 6 ligand preferably coupled to another compound (i.e. another moiety) that is capable of functionally inhibiting a cancer stem cell. An example of such another compound is a toxin.

Examples of an Lgr5 or 6 ligand are ligands that are a member of the insulin peptide family. Suitable examples are Ins15 and relaxin3. Another suitable example is a cysteine-knot protein such as Noggin, Gremlin, Dan, or Cerberus. Moreover, a natural ligand can be modified such that it permanently blocks Lgr5 or 6 activity.

All the above mentioned Lgr5 or 6 protein inhibitors, inhibitors of the mRNA transcripts of Lgr5 or 6, as well as the described cancer stem cell inhibitors are very useful for therapeutic cancer therapy approaches.

In yet another embodiment, the invention provides the use of at least one Lgr5 or 6 inhibitor or at least one Lgr5 or 6 binding compound as described herein (e.g. an Lgr5 or 6 protein inhibitor or an inhibitor of the mRNA transcripts of Lgr5 or 6 or a cancer stem cell inhibitor) for the manufacture of a medicament for the treatment of cancer.

Preferably, said inhibitors are obtainable according to a method of the invention, i.e. a method for testing the effect of a possible anti cancer stem cell compound comprising contacting (treating) a set of cancer stem cells according to the invention in vitro with said possible anti cancer stem cell compound and testing whether said treated cancer stem cells are capable of generating a continuously growing tumor and wherein said possible cancer stem cell compound is preferably designed as an Lgr5 or 6 inhibitor or as an Lgr5 or 6 binding compound. In a preferred embodiment, use is made of an Lgr5 or 6 inhibitor or an Lgr5 or 6 binding compound.

The invention further provides a method for reducing or inhibiting tumor maintenance potential of a tumor, comprising providing said tumor with a compound that is designed as an Lgr5 and/or 6 inhibitor, or preferably that is capable of binding to Lgr5 and/or 6.

An anti cancer stem cell therapy is very useful to eradicate the part of the tumor that maintains the tumor and is involved in invasive growth and metastasis. Although such an approach is considered to be a very effective cancer therapy, improved or increased results can be obtained by combining the anti cancer stem cell therapy with conventional cancer therapy.

In a preferred embodiment, the invention provides the use of at least one Lgr5 or 6 inhibitor or at least one Lgr5 or 6 binding compound as described herein (e.g. an Lgr5 or 6 protein inhibitor or an inhibitor of the mRNA transcripts of Lgr5 or 6 or a cancer stem cell inhibitor) for the manufacture of a medicament for the treatment of cancer, further comprising general anti-cancer therapy. Examples of said general (or conventional) anti-cancer therapy are radiation, chemotherapy, antibody-based therapy or small molecule based treatments. Combined treatment leads to an approach of killing the minority cancer stem cell population as well as the bulk of the tumor.

In another preferred embodiment, the invention provides the use of at least one Lgr5 or 6 inhibitor or at least one Lgr5 or 6 binding compound as described herein (e.g. an Lgr5 or 6 protein inhibitor or an inhibitor of the mRNA transcripts of Lgr5 or 6 or a cancer stem cell inhibitor) for the manufacture of a medicament for the treatment of cancer, wherein cancer stem cells are involved in intestinal cancer, colon cancer, rectal cancer, colorectal cancer, skin cancer, esophageal cancer, breast cancer, prostate cancer, medulloblastoma or other brain cancers, liver cancer, stomach cancer, hair follicle cancer, retinal cancer, pheochromcytoma, head and neck cancer, testicular cancer, ovarian cancer, basel cell carcinoma of the skin or lung cancer. In this respect, "involved" means sustaining and/or maintaining and/or expanding.

Preferably, the treatment with at least one Lgr5 and/or 6 inhibitor or at least one Lgr5 and/or 6 binding compound is initiated before, after or during said conventional cancer therapy.

Although treatment with at least one Lgr5 and/or 6 inhibitor or at least one Lgr5 and/or 6 binding compound is considered to be effective, treatment with multiple inhibitors and/or binding compounds can provide improved results. This is especially true if the to be treated cancer stem cell comprises two, three or even more different Lgr proteins embedded in its cell membrane.

In a preferred embodiment, the invention provides the use of at least one Lgr5 and/or 6 inhibitor or at least one Lgr5 and/or 6 binding compound as described herein (e.g. an Lgr5 or 6 protein inhibitor or an inhibitor of the mRNA transcripts of Lgr5 or 6 or a cancer stem cell inhibitor) for the manufacture of a medicament for the treatment of cancer, wherein at least two Lg5 and/or 6 inhibitors or at least two Lgr5 and/or 6 binding compounds or a combination of at least one Lgr5 and/or 6 inhibitor and at least one Lgr5 and/or 6 binding compound are/is used.

The invention thus provides use of at least two Lgr5 and/or 6 inhibitors or at least two Lgr5 and/or 6 binding compounds or a combination of at least one Lgr5 and/or 6 inhibitor and at least one Lgr5 and/or 6 binding compound for the manufacture of a medicament for the treatment of cancer stem cells. An inhibitor and/or binding compound can, but need not be, directed to one and the same Lgr protein, e.g. a binding compound and an inhibitor against Lgr5. The mixture of at least two Lgr5 or 6 inhibitors or at least two Lgr5 or 6 binding compounds or a combination of at least one Lgr5 or 6 inhibitor and at least one Lgr5 or 6 binding compound is for example directed against Lgr5 and 6. The latter is especially useful in a method for obtaining brain, head and neck, testis, breast, prostate, skin, ovary or hair follicle cancer stem cells.

Another already described useful compound is a stem cell inhibitor comprising an Lgr5 and/or 6 ligand preferably coupled to another compound (i.e. another moiety) that is capable of functionally inhibiting a cancer stem cell. An example of such another compound is a toxin. Examples of an Lgr5 or 6 ligand are ligands that are a member of the insulin peptide family. Suitable examples are Ins15 and relaxin3. Another suitable example is a cysteine-knot protein such as Noggin, Gremlin, Dan, or Cerberus. Such a compound can also be used in a cancer stem cell therapy.

Therefore, the invention provides use of a compound that is capable of binding to a ligand of Lgr5 and/or 6 for the manufacture of a medicament for the treatment of cancer stem cells. Preferably, said ligand is coupled to another compound (i.e. another moiety) that is capable of functionally inhibiting a cancer stem cell, such as a toxin or an enzyme capable of converting a prodrug to a toxic agent. Even more preferably, such a treatment is combined with general cancer therapy, such as radiation, chemotherapy, antibody-based therapy or small molecule based treatments.

In yet another embodiment, the invention provides use of a compound that is capable of binding to a ligand of Lgr5 and/or 6 for the manufacture of a medicament for the treatment of cancer stem cells. Preferably the binding of said compound to an Lgr5 and/or 6 ligand is such that said ligand is no longer capable of binding to Lgr5 and/or 6. An example is an antibody or antibody derivative or antibody fragment that captures a (natural) ligand of Lgr5 and/or 6 and thus prevents the activation of Lgr5 and/or 6.

The invention further provides a composition comprising at least one Lgr5 and/or 6 inhibitor or at least one Lgr5 and/or 6 binding compound or at least one Lgr5 and/or 6 ligand or at least one compound capable of binding to an Lgr5 and/or 6 ligand, preferably all as described herein before. Preferably said composition is a pharmaceutical composition. Such a pharmaceutical composition can further comprise any pharmaceutically acceptable excipient, stabilizer, activator, carrier, permeator, propellant, desinfectant, diluent and/or preservative. A pharmaceutical composition may be in any desired form, e.g. a tablet, infusion fluid, capsule, syrup, etc.

In a further preferred embodiment a (pharmaceutical) composition comprises at least two Lgr5 and/or 6 inhibitors or at least two Lgr5 and/or 6 binding compounds or a combination of at least one Lgr5 and/or 6 inhibitor and at least one Lgr5 and/or 6 binding compound.

Now that the inventors have disclosed that Lgr5 and/or 6 are cancer stem cell markers this further opens possibilities in the field of diagnostics. One can for example use an Lgr5 and/or 6 binding compound to determine the cancer stem cell content of a tumor or to determine the presence or absence of a cancer stem cell in a body fluid such as blood. Preferably, the binding compound has a high affinity for Lgr5 or 6 (i.e. the Kd is at least $10^{-7}$). Suitable binding compounds are an Lgr5 and/or 6 ligand, an antibody or an antibody derivative or an antibody fragment capable of binding to Lgr5 and/or 6, e.g. an antibody or derivative or fragment thereof that has affinity for Lgr5 and/or 6.

The invention thus also provides a method for determining cancer stem cell content of a tumor, comprising contacting said tumor with an Lgr5 and/or 6 binding compound, removing unbound binding compound and determining whether any bound binding compound is present in said tumor.

In a preferred embodiment, said method is an in vitro method. Even more preferably, said binding compound is labeled such that it can be identified. Suitable labels are for example a protein (fragment) such as the antibody Fc tail or Staphylococcal protein A or Glutathion-S-transferase, a short antigenic peptide tag such as the Myc, FLAG or HA tag or an oligomeric Histidine-tag, an enzymatic tag such as Alkaline Phosphatase, a fluorescent protein tag (such as Green Fluorescent Protein). However, it is also possible to use a second compound that has affinity for the binding compound and labeling said second compound with a suitable label (i.e. an indirect analysis).

For in vivo application, the invention further provide use of an Lgr5 and/or 6 binding compound in the preparation of a diagnostic for the diagnosis of cancer stem cell presence and/or content in a tumor.

Said sample is for example obtained from a body fluid or a sample obtained from a solid tumor.

In a preferred embodiment, the invention provides a method for determining cancer stem cell content of a tumor, comprising contacting said tumor with an Lgr5 and/or 6 binding compound and determining whether any bound binding compound is present in said tumor. The invention also provides use of an Lgr5 and/or 6 binding compound in the preparation of a diagnostic for the diagnosis of cancer stem cell presence and/or content in a sample, wherein said binding compound is conjugated to a substance that allows radioactive imaging, positron emission tomography (PET) scanning, magnetic resonance imaging (MRI) scanning, or X-ray/computed tomography (CT) scanning.

The invention further provides a method for determining whether a body fluid comprises a cancer stem cell, comprising optionally obtaining a sample from said body fluid
contacting said body fluid with an Lgr5 and/or 6 binding compound
removing unbound binding compound
detecting any bound complex comprising an Lgr5 and/or 6 binding compound, and determining the presence of a cancer stem cell based on the presence of detected bound complex.

Suitable binding compounds are an Lgr5 and/or 6 ligand, an antibody or an antibody derivative or an antibody fragment capable of binding to Lgr5 and/or 6, i.e. an antibody or derivative or fragment thereof that has affinity for Lgr5 and/or 6.

The step of removing any unbound binding compound is for example accomplished by washing with a suitable solution or buffer.

Examples of body fluid are blood, urine, lymph fluid or tears.

In a preferred embodiment, said method is an in vitro method.

Suitable labels have been mentioned above.

The described diagnostic methods are also very useful for determining whether an anti cancer therapy leads to eradication of (at least part of the) cancer stem cells. If for example use is made of general anti cancer therapy (or combined treatment with for example an Lgr5 and/or 6 inhibitor), the effect of said therapy on the cancer stem cell can be determined by determining the presence or absence of cells bearing Lgr5 and/or 6.

In yet another embodiment, the invention provides a method for determining the effectivity of an anti cancer treatment, comprising treating cancer and determining whether cancer stem cells are present comprising contacting said cancer with an Lgr5 and/or 6 binding compound.

Such a method can be performed in vitro as well as in vivo.

Preferably the presence of cancer stem cells is determined before treatment and during or after treatment such that it can determined whether or not the applied treatment results in a changed (preferably decreased) amount of cancer stem cells.

The invention further provides a method for treating an individual in need thereof comprising administering an effective amount of a herein described pharmaceutical composition to said individual and optionally further subjecting said individual to conventional cancer therapy such as radiation or chemotherapy.

The invention will be explained in more detail in the following, non-limiting examples.

FIGURE LEGENDS

FIG. 1. Gpr49/Lgr5 is a Wnt target gene in a human colon cancer cell line and is expressed in mouse crypts. a: Northern blot analysis (upper panel); ethidium bromide-stained gel (lower panel). Lane 1: Control Ls174T-L8 cells. Lane 2: Ls174T cells after 24 hours doxycycline induced Wnt pathway inhibition as in 6 (References 2). Note the strong downregulation of the 4.4 kb Grp49 mRNA upon Wnt pathway inhibition. Lane 3: RNA extracted from isolated mouse small intestinal crypts, which unavoidably suffers from limited degradation resulting in some smearing. Lane 4: RNA extracted from isolated mouse villi. Note the specific expression of Grp49 in mouse crypts. b/c Two overlapping images of an in-situ hybridization performed on small intestines of an APCmin mouse, illustrating the ubiquitous expression of Grp49 at crypt bottoms (examples marked with white arrows) and the expression in the adenoma in the left panel (marked by a broken line).

Figure 2:
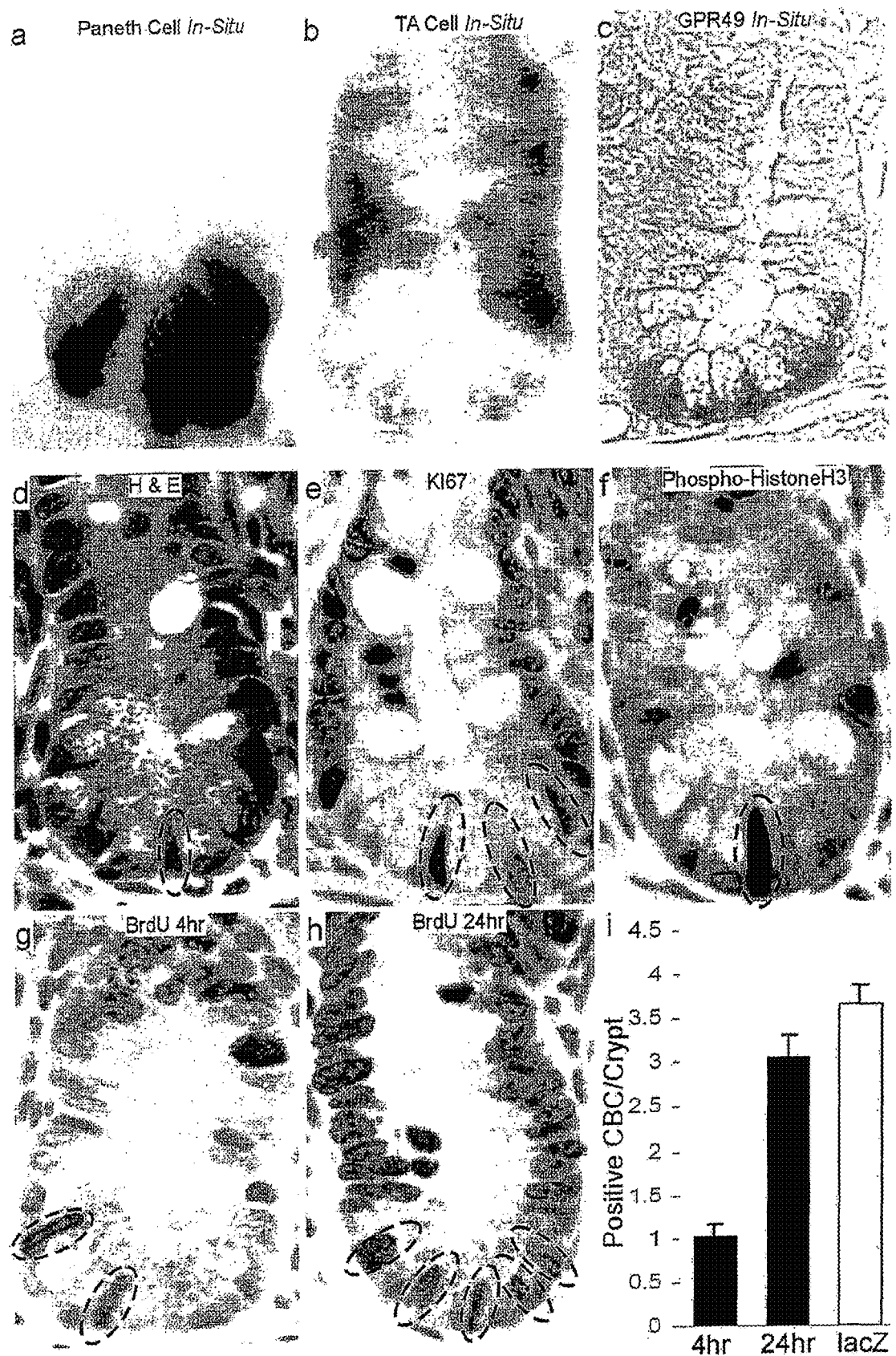

FIG. 2. Gpr49/Lgr5 expression in cycling Crypt Base Columnar (CBC) cells of the small intestine. a-c, In-Situ hybridization was performed with probes specific for 3 Tcf target genes demonstrating non-overlapping expression patterns on the crypt epithelium. a: Cryptdin specifically marks Paneth cells at the crypt base; b: KIAA0007 marks the TA cells located above the Paneth cells c: Gpr49/Lgr5 is specifically expressed in 4-8 cells intermingled with the Paneth cells at the crypt base. All sense controls were negative (not shown). d: CBC cells (circled) are only poorly visible on heamatoxylin/eosin stained sections. e: CBC cells (circled) are KI67+f: Some CBC cells express the M-phase marker phospho-histidine H3 (circled). g: BrdU incorporation in CBC cells 4 hours after a single dose of BrdU (circled). h: BrdU incorporation in CBC cells after 24 hour continuous BrdU labeling (circled). Black bars: Numbers of BrdU-positive CBC cells per crypt section after 4 hours or 24 hours. White bar: Total number of CBC cells per crypt section assessed by counting LacZ-positive cells in Gpr49-LacZ mice.

Figure 3:
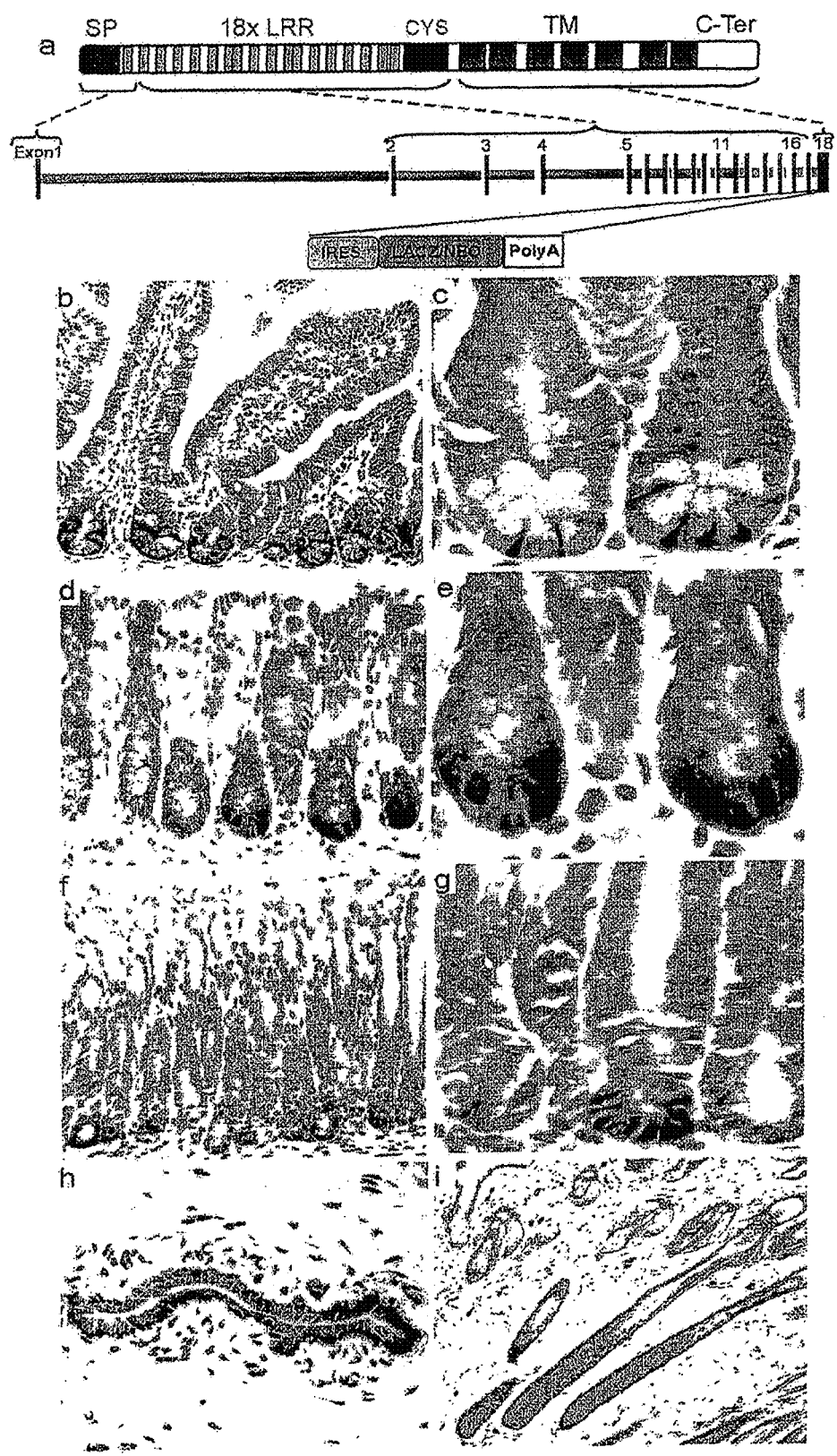

FIG. 3. Restricted expression of a GPR49-LacZ reporter gene in adult mice a: Generation of mice carrying lacZ integrated into the last exon of the Gpr49 gene, removing all transmembrane regions of the encoded Gpr49 protein. b-h, Expression of GPR49lacZ in selected adult mouse tissues. b/c: In the small intestine expression is restricted to 6-8 slender cells intermingled with the Paneth cells at the crypt base. d/e: In the colon, expression is confined to a few cells located at the crypt base. f/g: Expression in the stomach is limited to the base of the glands. h: In the mammary glands, expression was evident only in smaller, actively proliferating glands, where it was restricted to basal epithelial cells. i: In the skin, expression occurs in the outer root sheath of the hair follicles in a domain extending from the bulge to the dermal papilla.

Figure 4:
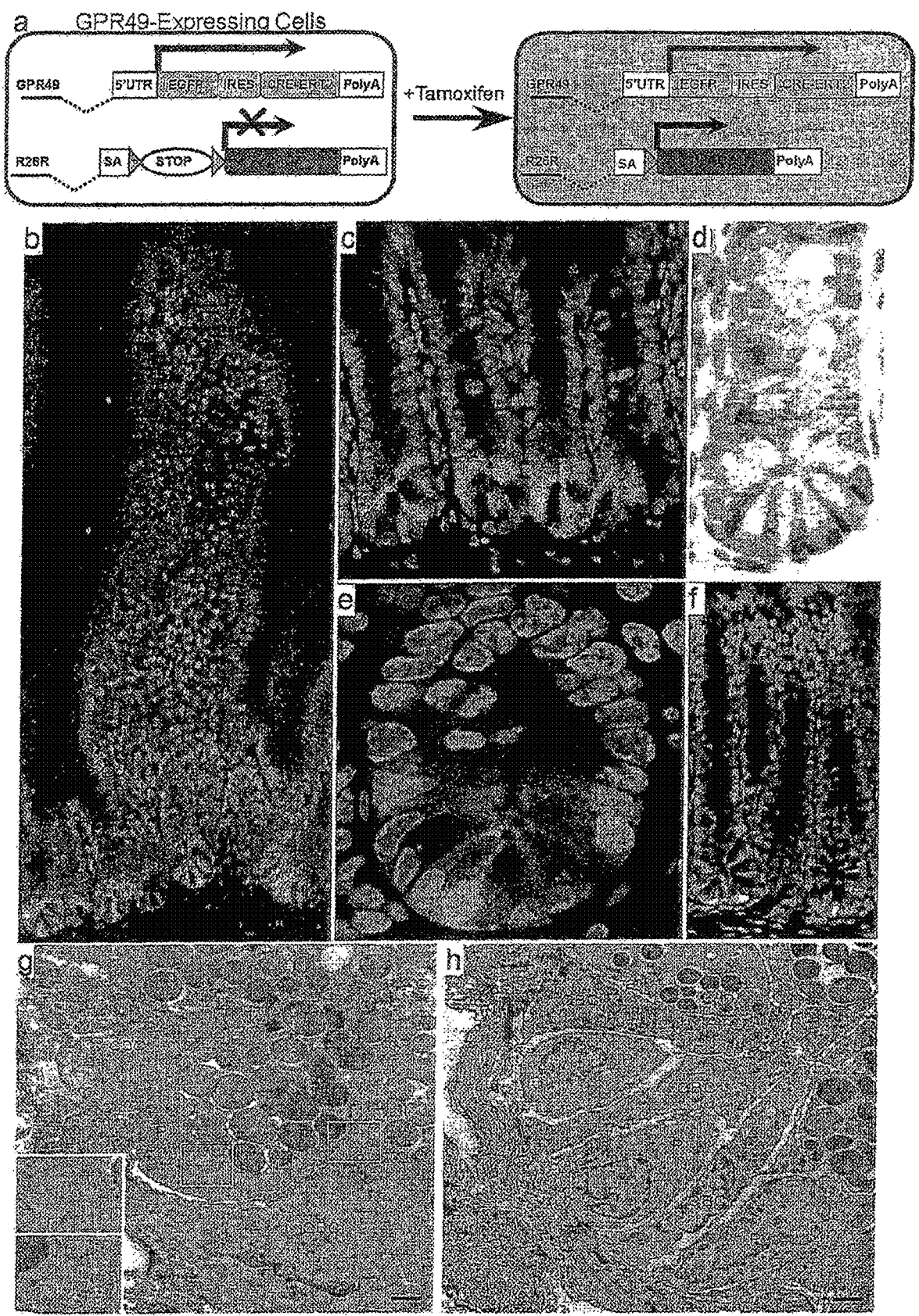

FIG. 4. EGFP expression in a GPR49-EGFP-Ires-CreERT2 knock-in mouse faithfully reproduces the GPR491acZ expression pattern in the intestinal tract. a: Generation of mice expressing EGFP and CreERT2 from a single bicistronic message by gene knock-in into the first exon of Gpr49. b,c,e: Confocal GFP imaging counterstained with the red DNA dye ToPro-3 confirms that Gpr49 expression is restricted to the 6-8 slender cells sandwiched between the Paneth cells at the crypt base of the small intestine. b: Entire crypt-villus unit; c: enlargement of crypt regions; d: Immunohistochemical analysis of EGFP expression in intestinal crypts. e: 2D image of 3D reconstruction supplied as supplemental movie in FIG. 7. Confocal imaging of EGFP expression in the colon confirms Gpr49 expression is restricted to a few cells located at the crypt base. g: CryoEM section of crypt stained for GFP with immunogold (scale bar=1000 nm). Quantification of specificity of labeling: Gold particles were counted over 255 µm2 of CBC cell cytosol (1113 particles), 261 µm2 of Paneth cell cytosol (305 particles) and 257 µm2 of fibroblast cytosol (263 particles) outside the crypt. Thus CBC cytoplasm had 4.36 gold particles/µm2 compared to the Paneth cells 1.17 gold particles/µm2 and to the fibroblast control 1.02 gold particles/µm2. C=Crypt lumen; P=Paneth cells; CBC=Crypt Base Columnar cells. h: Unlabeled CryoEM section (scale bar=2000 nm), underscoring the ultrastructural characteristics of CBC cells and their positioning relative to Paneth cells.

Figure 5:
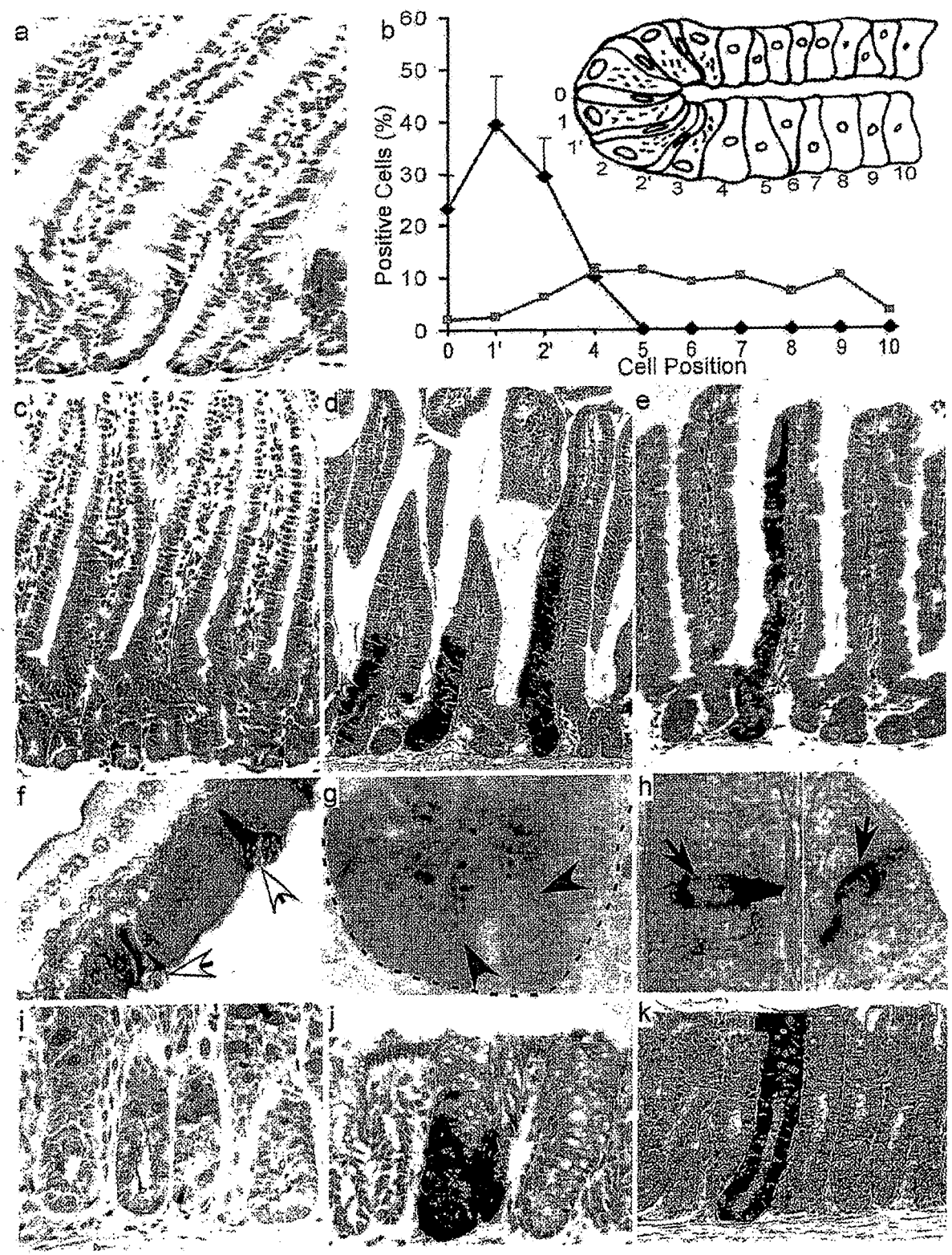

FIG. 5. Lineage tracing in the small intestine and colon. a: GPR49-EGFP-Ires-CreERT2 knock-in mouse crossed with Rosa26-LacZ reporter mice 12 hours after Tamoxifen injection b: frequency at which the blue cells appeared at specific positions relative to the crypt bottom, according to the scheme in the inset of FIG. 5b. The large majority of the Cre+ LacZ-labeled CBC cells occurred at positions between the Paneth cells, while only 10% of these cells were observed at the +4 position directly above the cells (blue line). Quantitative data on the position of long term DNA label-retaining cells obtained in adult mice post-irradiation (marking the "+4" intestinal stem cell) were published recently by Potten and colleagues17. Comparison of these data (red line) with the position of CBC cells carrying activated Cre. c-e: Histological analysis of LacZ activity in small intestine 1 day post-induction (c), 5 days post-induction (d) and 60 days post-induction (e). f-h: Double-labelling of LacZ-stained intestine using PAS demonstrates the presence of Goblet cells (f; white arrows) and Paneth Cells (g; blue arrows) in induced blue clones. Double-labelling with Synaptophysin demonstrates the presence of enteroendocrine cells within the induced blue clones (h; black arrows). i-k Histological analysis of LacZ activity in colon 1 day post-induction (1), 5 days post-induction (j) and 60 days post-induction (k).

Figure 6:
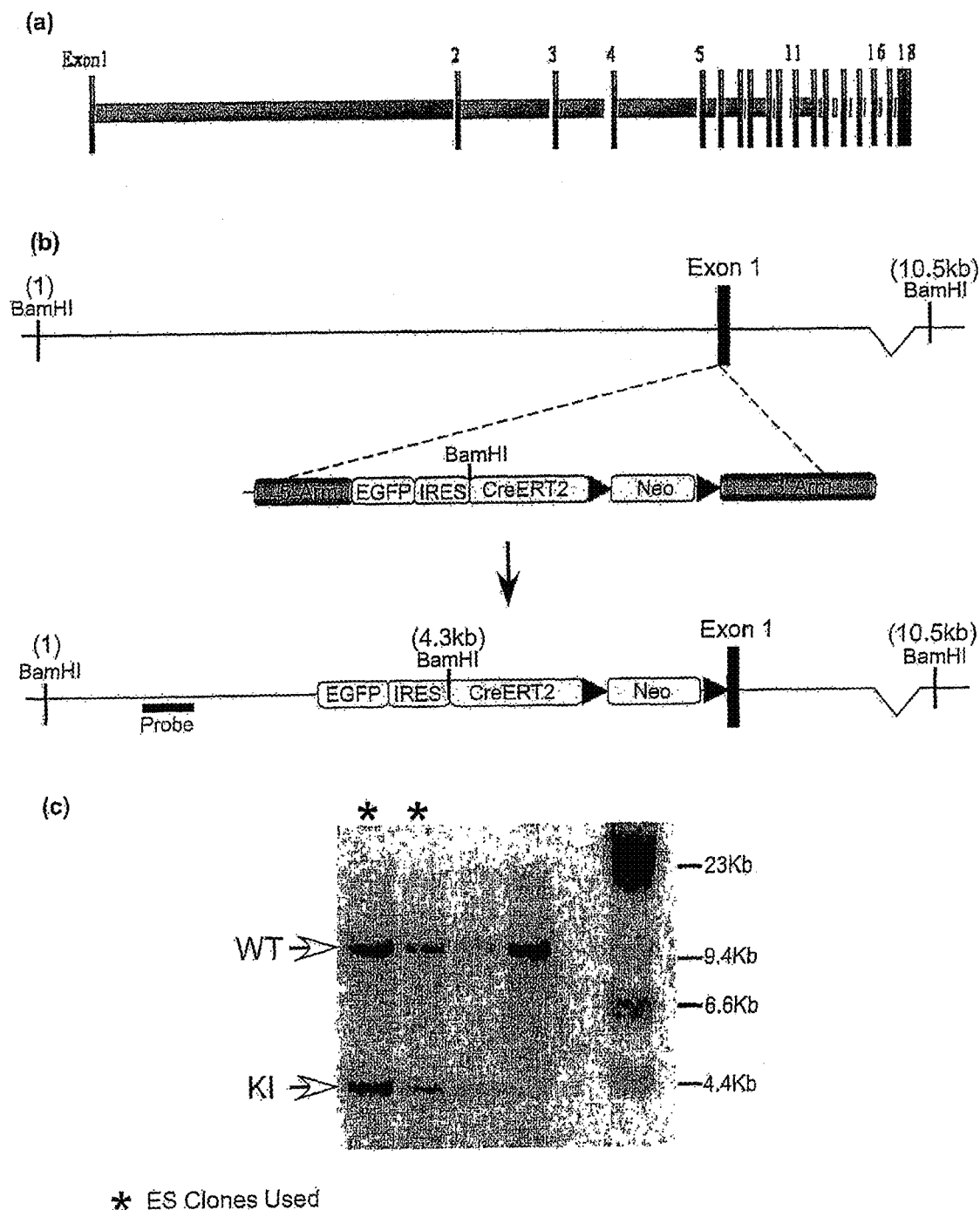

FIG. 6. Strategy for EGFP-ires-CreERT2 cassette knock-in into the Gpr49 locus a: Schematic structure of the mouse Gpr49 gene b: Southern blotting strategy to screen ES cells transfected with a knock-in construct targeting the ATG translational start in Exon I.

c: Four ES cell clones out of a total of 500 scored positive for the recombined BamHI band running at 4.3 kb. After re-screening of these 4 ES clones, the first two (asterisks) were selected for blastocyst injections.

Figure 7:
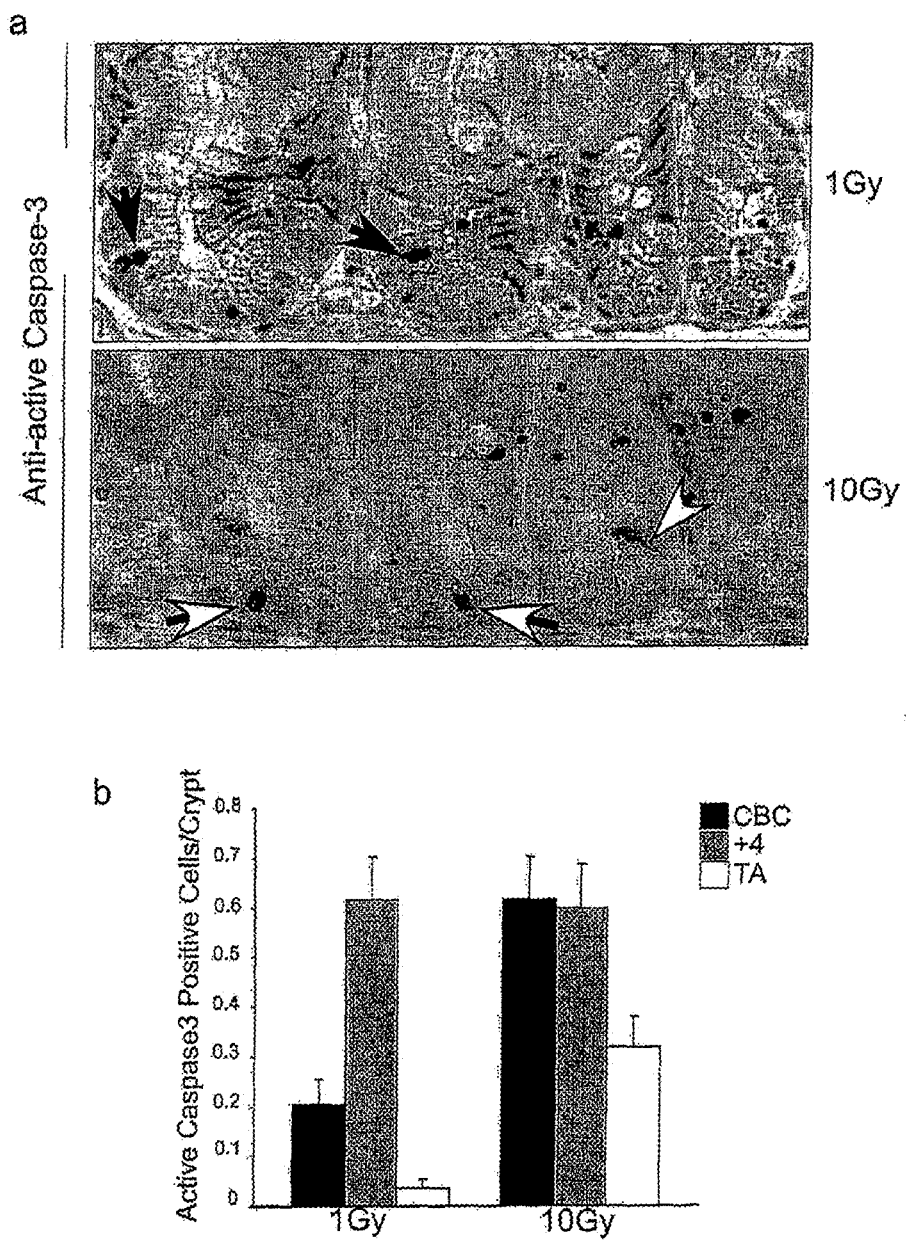

FIG. 7. Relative radiation sensitivity of CBC cells, +4 cells, and TA cells. Adult mice were irradiated with 1 Gy or 10 Gy and subsequently sacrificed 6 hours later, at the peak of apoptosis. a: Active Caspase-3-positive cells were visualized by immunohistochemistry (Upper panel—black arrows highlighting positive +4 cells following 1Gy irradiation; Lower panel-white arrows highlighting positive CBC cells following 10Gy irradiation). b: The frequency of positive cells per crypt was determined by counting three classes: CBC cells (located between the Paneth cells), +4 cells (located directly above the Paneth cells) and TA cells: located at position 5-15. Maximal apoptosis at +4 is already reached at 1 Gy while 10 Gy causes significantly more apoptosis than 1 Gy irradiation in CBC cells.

Figure 8:
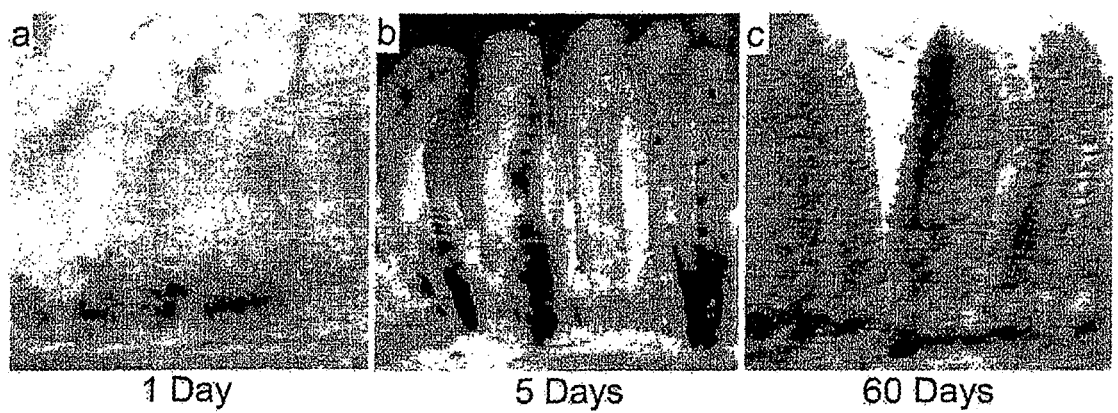

FIG. 8. Whole mount analysis of LacZ expression in small intestine of GPR49-EGFP-Ires-CreERT2 knock-in mice crossed with Rosa26-LacZ reporter mice at the indicated time points following Tamoxifen injection a:1 day post-induction. b: 5 days post-induction. c: 60 days post-induction.

Figure 9:
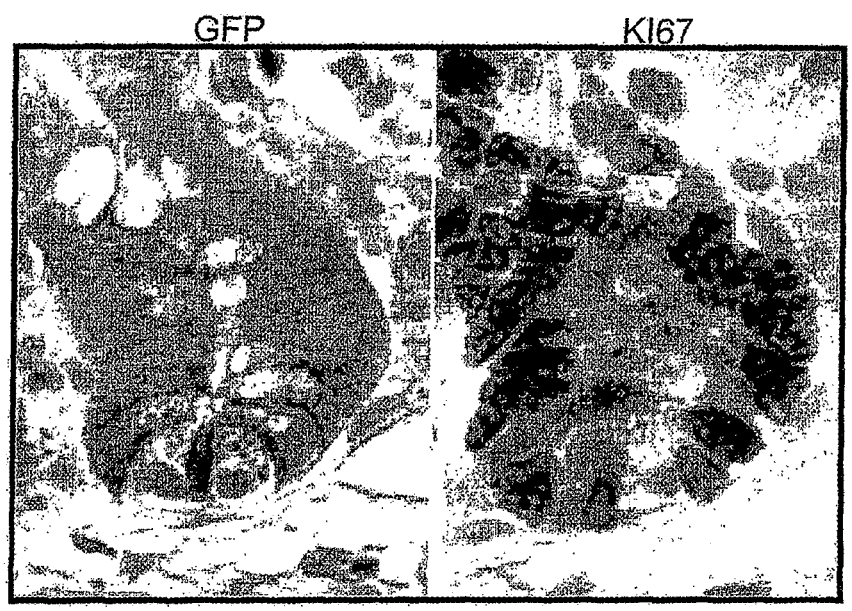

FIG. 9. Colocalisation of proliferation marker Ki67 and GFP-positive CBC cells in the intestinal crypts of GPR49-EGFP-CreERT2 mice (serial sections).

FIG. 10. Sequences of the human, mouse and rat receptors.

Figure 11:
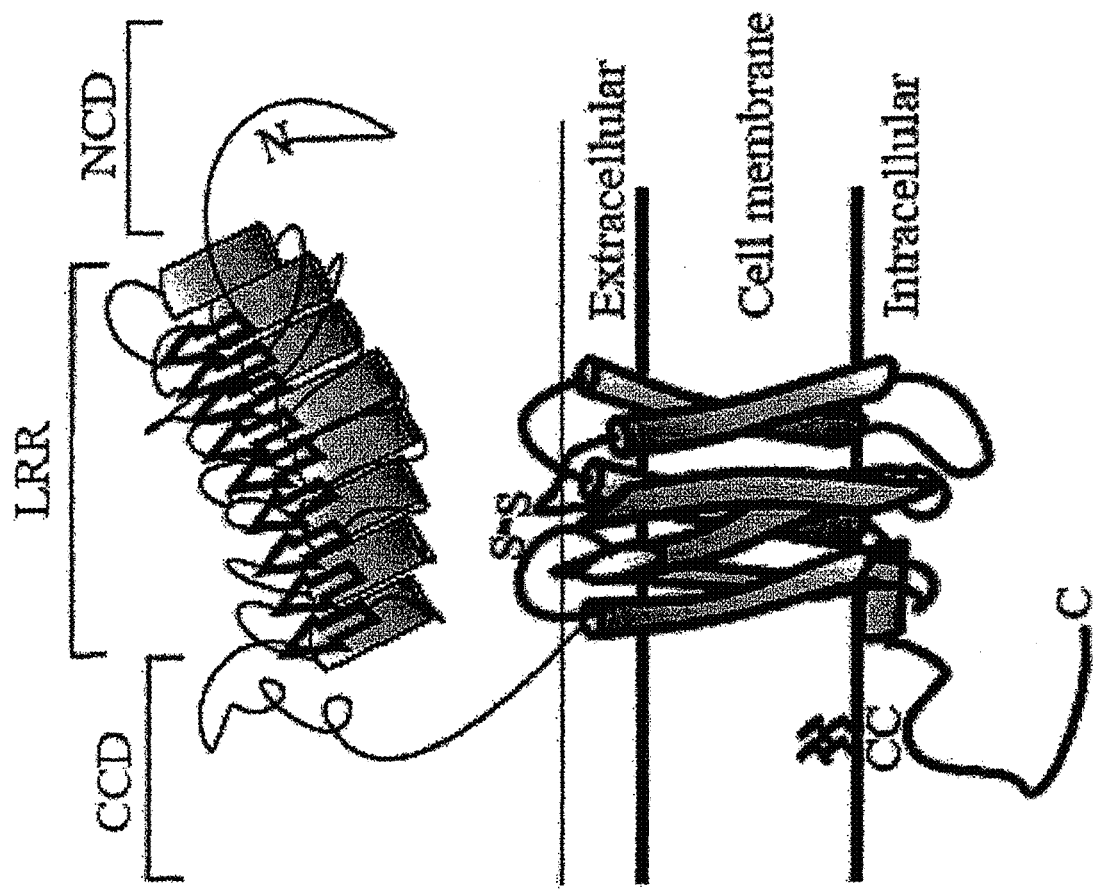

FIG. 11. Predicted structure of Lgr4, 5 and 6.

Figure 12:
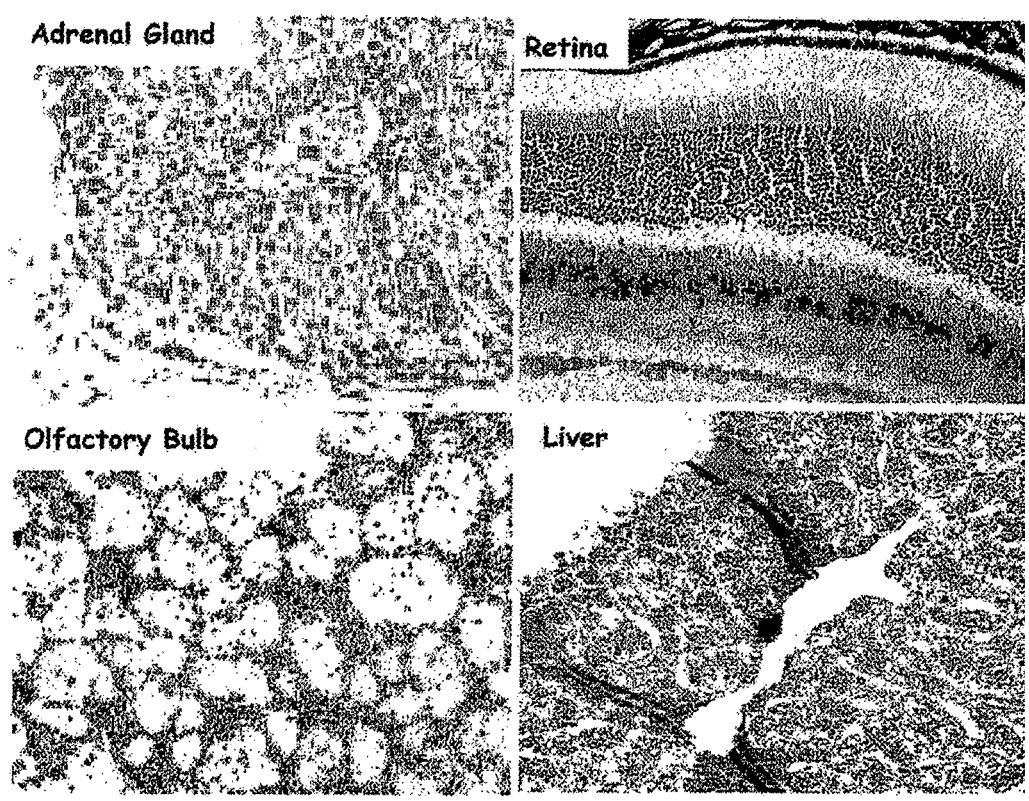

FIG. 12. Restricted expression of a GPR49-LacZ reporter gene in adult mice Expression of GPR49lacZ in selected adult mouse tissues. LGR5 is restricted to rare cell populations in the brain (glomeruli of the olfactory bulb and several other poorly defined regions) (A), the eye (inner nuclear layer of the retina) (B), liver (cells surrounding the portal triads) (C) and adrenal gland (D)

Figure 13:
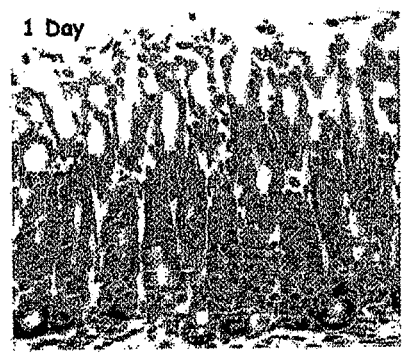
Figure 13:
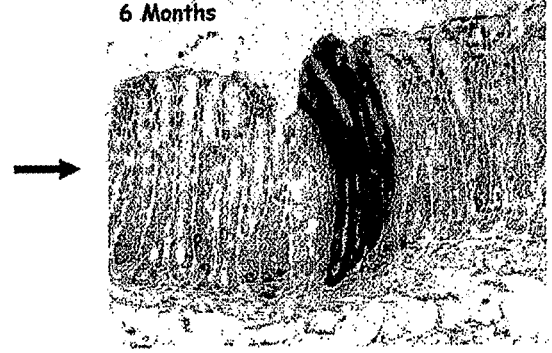

FIG. 13. Lineage tracing in the stomach Lgr5-EGFP-CreERT2 mice were crossed with Rosa26R reporter mice and Cre enzyme activity induced in the LGR5+ve cells by IP injection of Tamoxifen. LacZ reporter gene activity is initially restricted to the LGR5 cells (A), but rapidly expands to include the entire epithelium in the Stomach over time (B). This "lineage tracing" is maintained over long periods of time (B). This demonstrates that all epithelial cells are derived from the LGR5+ve population in this tissue, proving that they are stem cells.

Figure 14:
Figure 14:

FIG. 14. Lineage tracing in the mammary gland Lgr5-EGFP-CreERT2 mice were crossed with Rosa26R reporter mice and Cre enzyme activity induced in the LGR5+ve cells by IP injection of Tamoxifen. LacZ reporter gene activity is initially restricted to the LGR5 cells (A), but expands to include the myoepithelium of newly-formed milk glands in lactating females (B), indicating that LGR5 is specifically marking myoepithelial stem cells in this organ.

Figure 15:
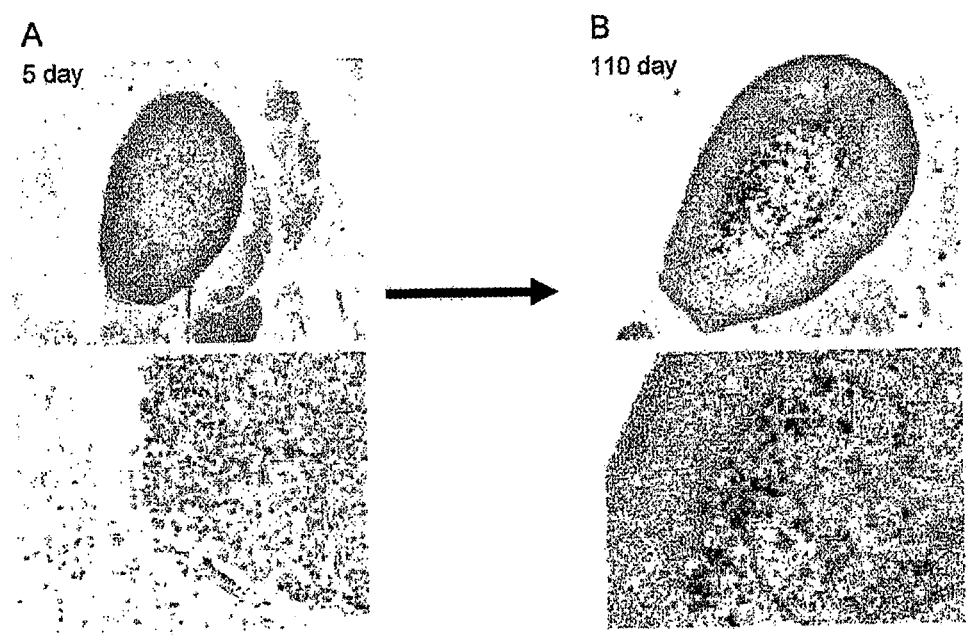

FIG. 15. Lineage tracing in the adrenal gland. Lgr5-EGFP-CreERT2 mice were crossed with Rosa26R reporter mice and Cre enzyme activity induced in the LGR5+ve cells by IP injection of Tamoxifen. LacZ reporter gene activity is initially restricted to the LGR5 cells (A), but expands to include the medulla of the adrenal gland (B), indicating that LGR5 is specifically marking adrenal medulla stem cells.

Figure 16:
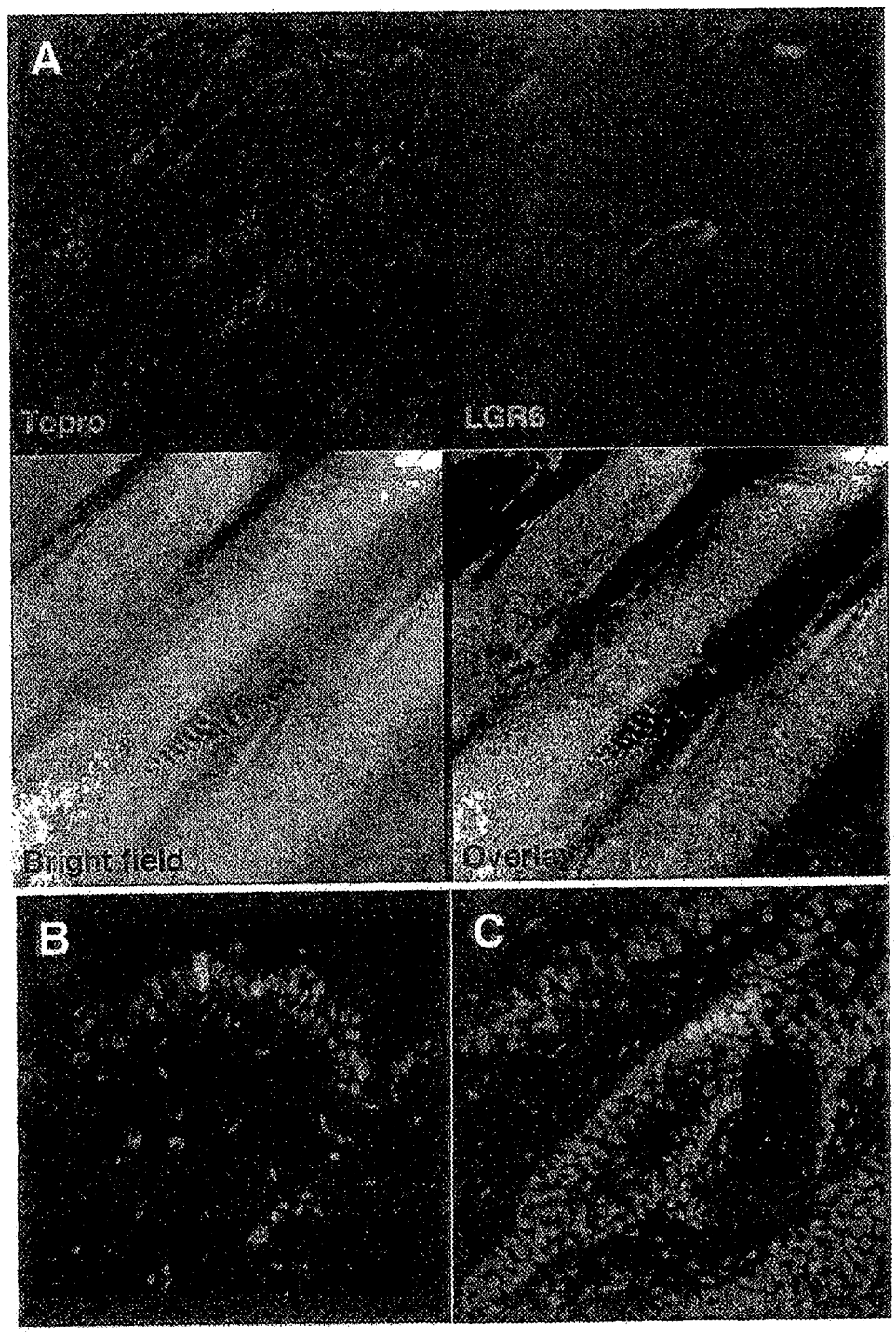

FIG. 16. Lgr6 is expressed in cells of the upper bulge area of the mouse hair follicle and in basal cells of the epidermis. Skin sections of appr. 26 days old Lgr6-EGFP-Ires-CreERT2 mice (early anagen) were obtained and stained for nuclear DNA (Topro) and EGFP visualized using confocal microscopy (A-C). During early anagen Lgr6 is expressed in the upper bulge (A, C) and the basal epidermis (A, B).

Figure 17:
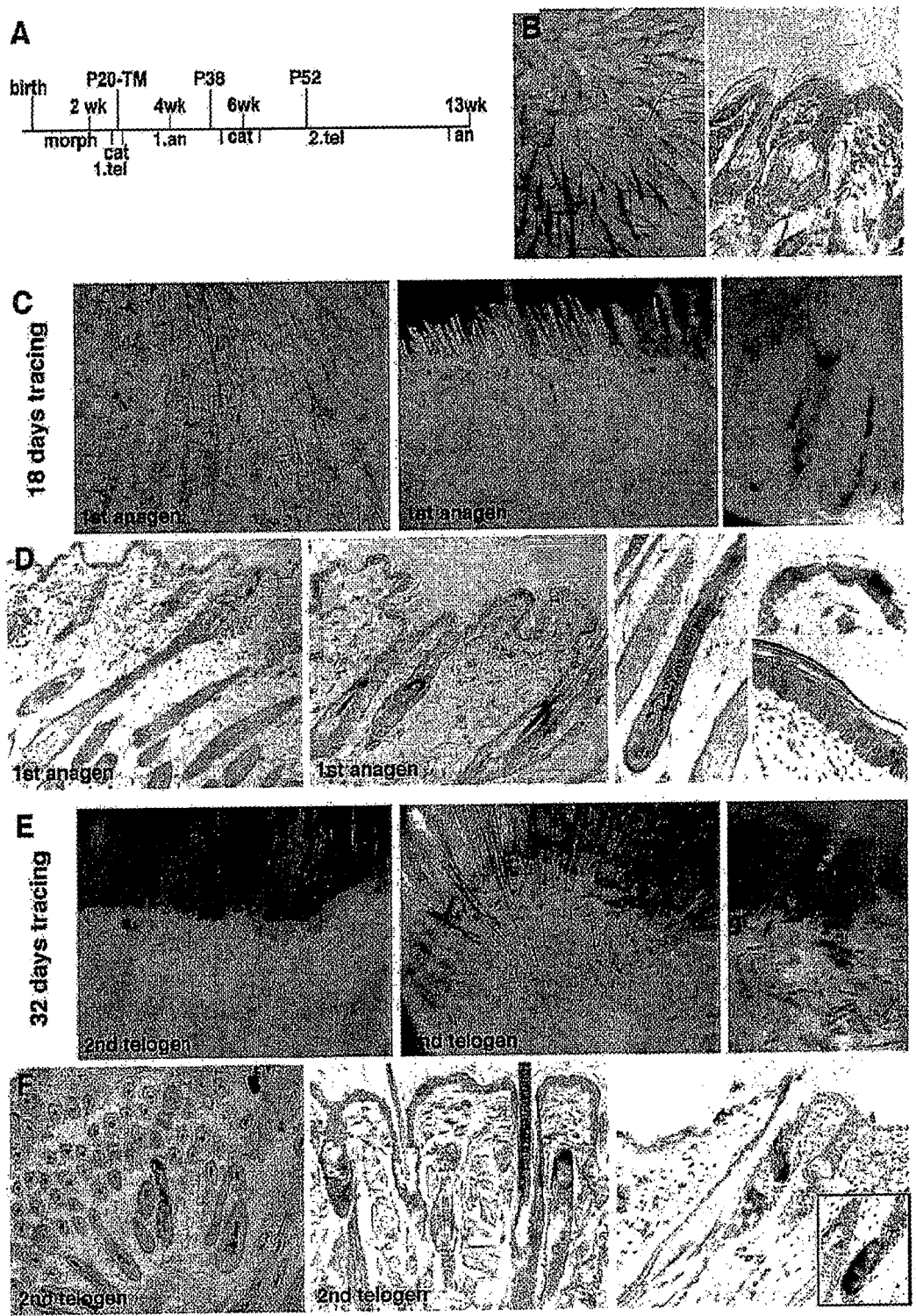

FIG. 17. The progeny of Lgr6+ cells contribute to all structures of the hair follicles (HF), interfollicular epidermis (IFE) and sebaceous glands (SG). To trace the progeny of Lgr6+ cells Lgr6-EGFP-Ires-CreERT2/ROSA26-LacZ mice were injected with tamoxifen (TM) at P20 when HFs are in telogen (A). At P23 a first staining in the IFE and HFs was detected (B). Analysis of LacZ staining progeny at P38 (1st anagen, C, D) and P52 (2nd telogen, E, F) revealed contribution to all parts of the HFs, IFEs and SGs.

Figure 18:
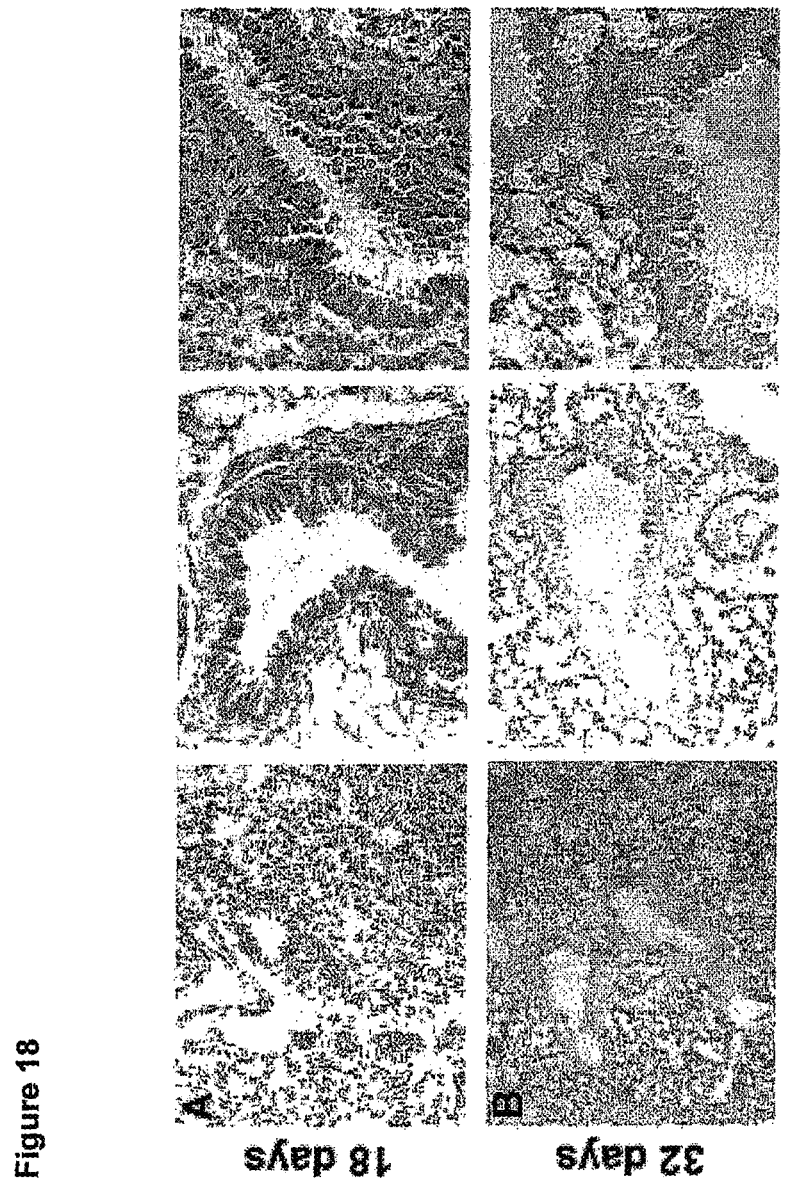

FIG. 18. The progeny of Lgr6+ cells contribute to the myoepithelium of the lung. To trace the progeny of Lgr6+ cells Lgr6-EGFP-Ires-CreERT2/ROSA26-LacZ mice were injected with tamoxifen (TM) at P20. Analysis of LacZ staining progeny at P38 (A, 10×, 20× and 40× magnification from left to right) and P52 (B, 10×, 20× and 40× magnification from left to right) revealed contribution to the myoepithelium underlying the bronchioles of the lung.

Figure 19:
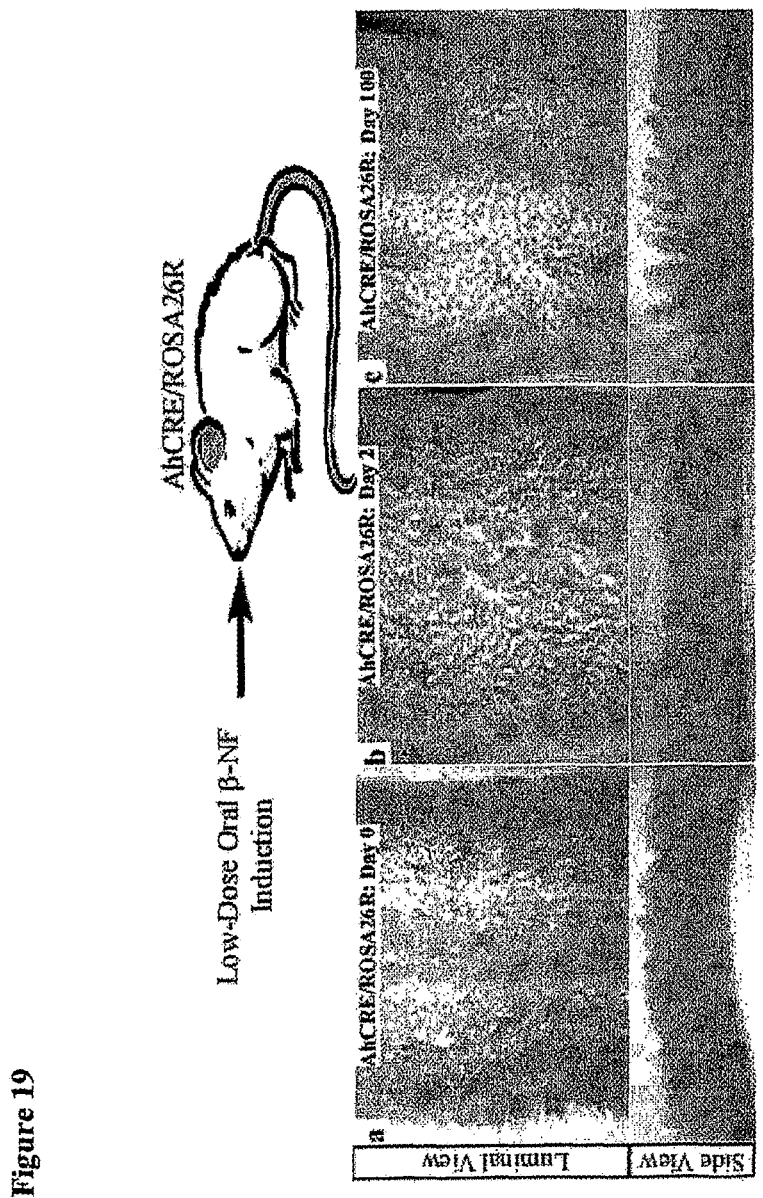

FIG. 19. Low-dose oral induction with ß-NF does not induce Cre-mediated deletion in stem cells of AHCre mice. Intestinal whole-mounts stained for ß-galactosidase from AhCre+ Rosa26R+ mice. a: No activation of the Rosa-lacZ reporter gene is observed in intestines from non-induced AhCre+ Rosa26R+ mice. b: Readily visible expression of lacZ throughout the intestine 2 days after a single gavage of 1 mg/kg ß-napthoflavone, indicating efficient Cre-mediated activation of the lacZ reporter. No lacZ expression is visible at the crypt base (lower panel) demonstrating the absence of Cre-mediated recombination at the crypt base. c: No lacZ-positive crypt/villus units are visible on whole-mount intestines 100 days post-induction, indicating that this dosing regime very rarely causes recombination within the intestinal stem cells.

Figure 20:
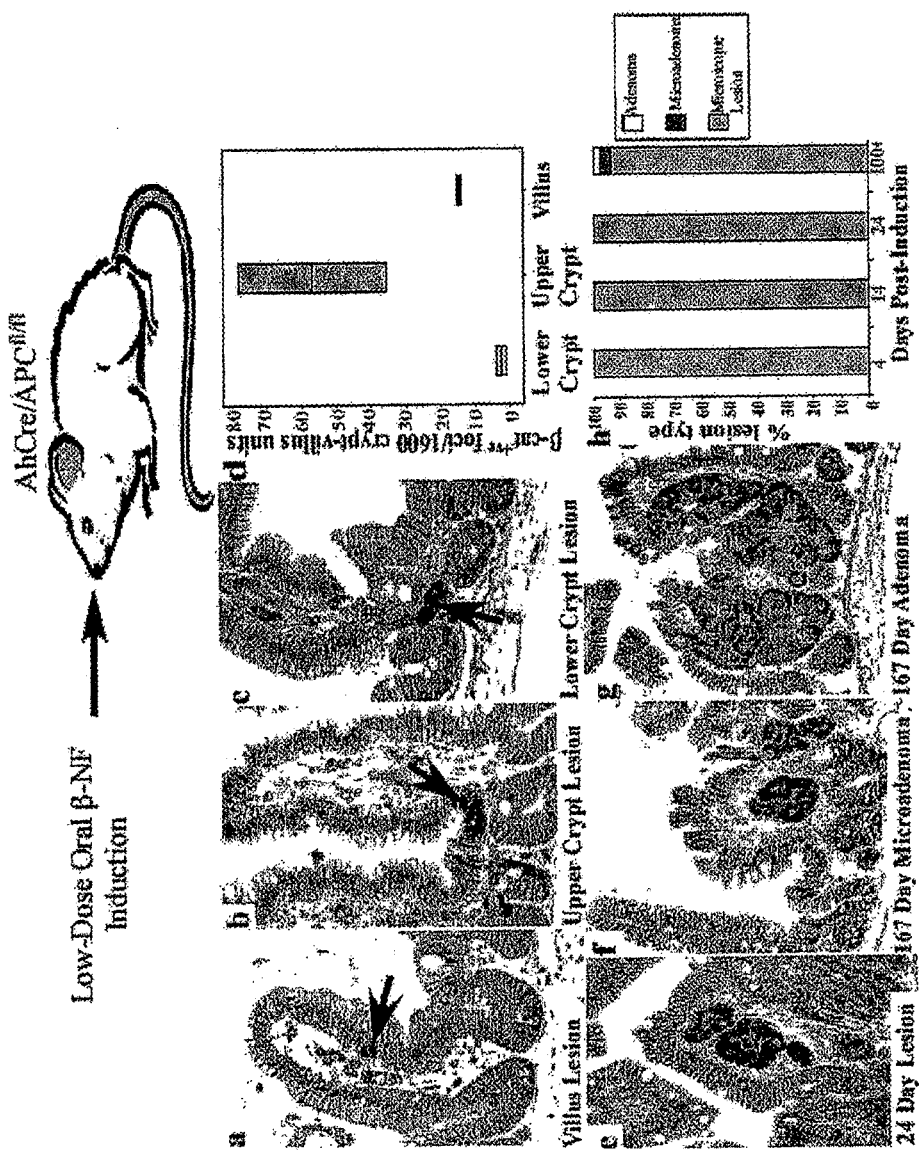

FIG. 20. Transformation of non-stem cells through loss of APC does not efficiently drive adenoma formation over extended time-periods. a-c: ß-catenin IHC performed on intestinal sections from AhCre+ Rosa26R+ Apcfl/fl 3 days following a single gavage of 1.0 mg/kg ß-napthoflavone.

Clusters of transformed cells with nuclear ß-catenin were frequently observed on the villus (a) and upper regions of the crypt (b). ß-cateninhigh clusters were only very rarely observed at the crypt base (c). These clusters are highlighted with black arrows. d: Quantification of the location of the ß-cateninhigh cell clusters on intestinal sections from AhCre+ Rosa26R+ Apcfl/fl 4 days following a single gavage of 1.0 mg/kg ß-napthoflavone. Box-plots showing numbers of foci observed at the crypt base, the upper crypt and the villus in 1600 crypt-villus units. Significantly more clusters were seen at the upper regions of the crypt than any other region (p=0.04, Mann Whitney, n=3). Nuclear ß-catenin foci were observed only very rarely at the crypt base. e:☐—ß-catenin IHC performed on intestinal section from AhCre+ Rosa26R+ Apcfl/fl 24 days following a single gavage of 1.0 mg/kg ß-napthoflavone. Here, nuclear ß-catenin is seen in a small lesion 24 days after cre induction. f,g: ß-catenin IHC performed on intestinal section from AhCre+ Rosa26R+ Apcfl/fl 167 days following a single gavage of 1.0 mg/kg ß-napthoflavone showing a microadenoma (f) and small adenoma (g) with nuclear ß-catenin. h: Quantification of adenoma formation over extended time-periods in AhCre+ Rosa26R+ Apcfl/fl following a single gavage of 1.0 mg/kg ß-napthoflavone. Lesion size was scored on intestinal whole-mounts from AhCre+ Rosa26R+ Apcfl/fl mice that had been stained for lacZ to help visualise the small lesions (at least 3 mice were used for each time-point). No adenomas were seen in mice up to and including day 24 and there was only the very rare microadenoma in mice at day 24. The occasional adenoma was observed in AhCre+ Rosa26R+ Apcfl/fl at 100 days (plus), however the majority of lesion remained microscopic showing that most lesions were not progressing to adenoma despite a long latency period.

Figure 21:
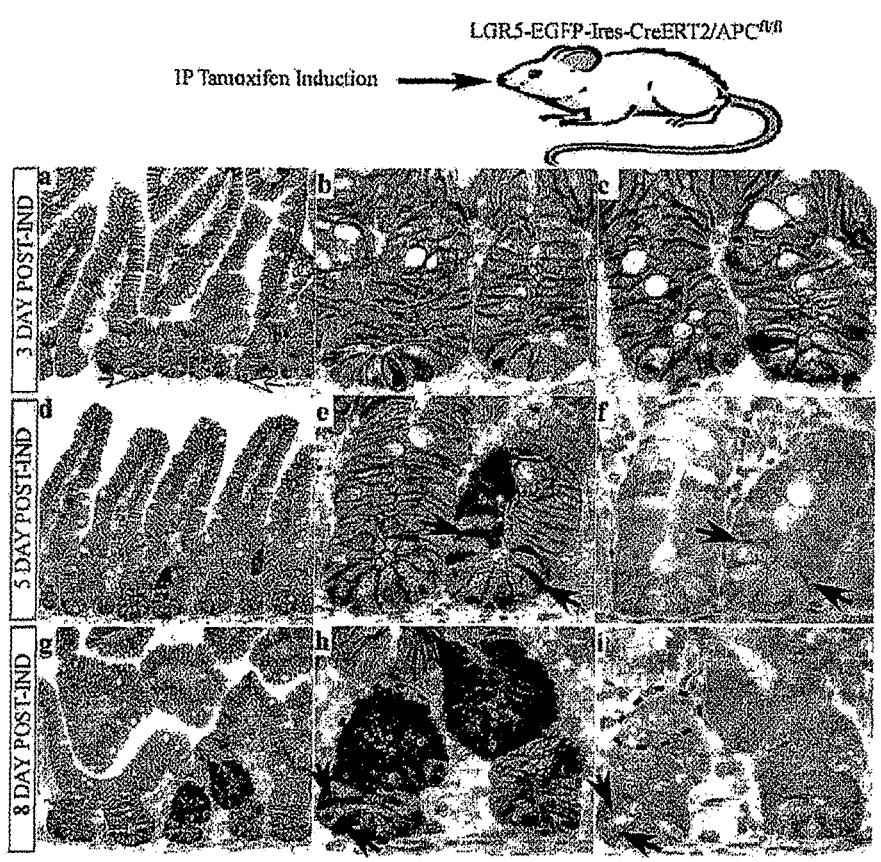

FIG. 21. Lgr5+ve intestinal stem cells transformed following loss of APC persist and fuel the rapid formation of ß-cateninhigh microadenomas. a-i: The consequences of Lgr5+ve intestinal stem cell transformation and their subsequent fate was tracked over an eight day period using ß-catenin and GFP as markers of transformed cells and Lgr5+ve stem cells respectively. a-c: Accumulation of the Wnt effector, ß-catenin is first observed in scattered Lgr5+ve stem cells 3 days after Cre induction in Lgr5-EGFP-Ires-CreERT2/APCfl/fl intestines. Representative examples of ß-cateninhigh Lgr5+ve stem cells are circled. d-f: Five days post-induction the transformed Lgr5-GFP+ve stem cells remain (e,f: black arrows) and are associated with clusters of transformed (ß-cateninhigh) cells within the TA compartment. g-h: Eight days post-induction the clusters of transformed cells have expanded to fill the TA compartment (h: red circle). The transformed Lgr5-GFP+ve stem cells at the crypt base persist (h,i: black arrows), but their transformed progeny within the TA compartment are Lgr5-GFP-ve. (h,i: red circles).

Figure 22:
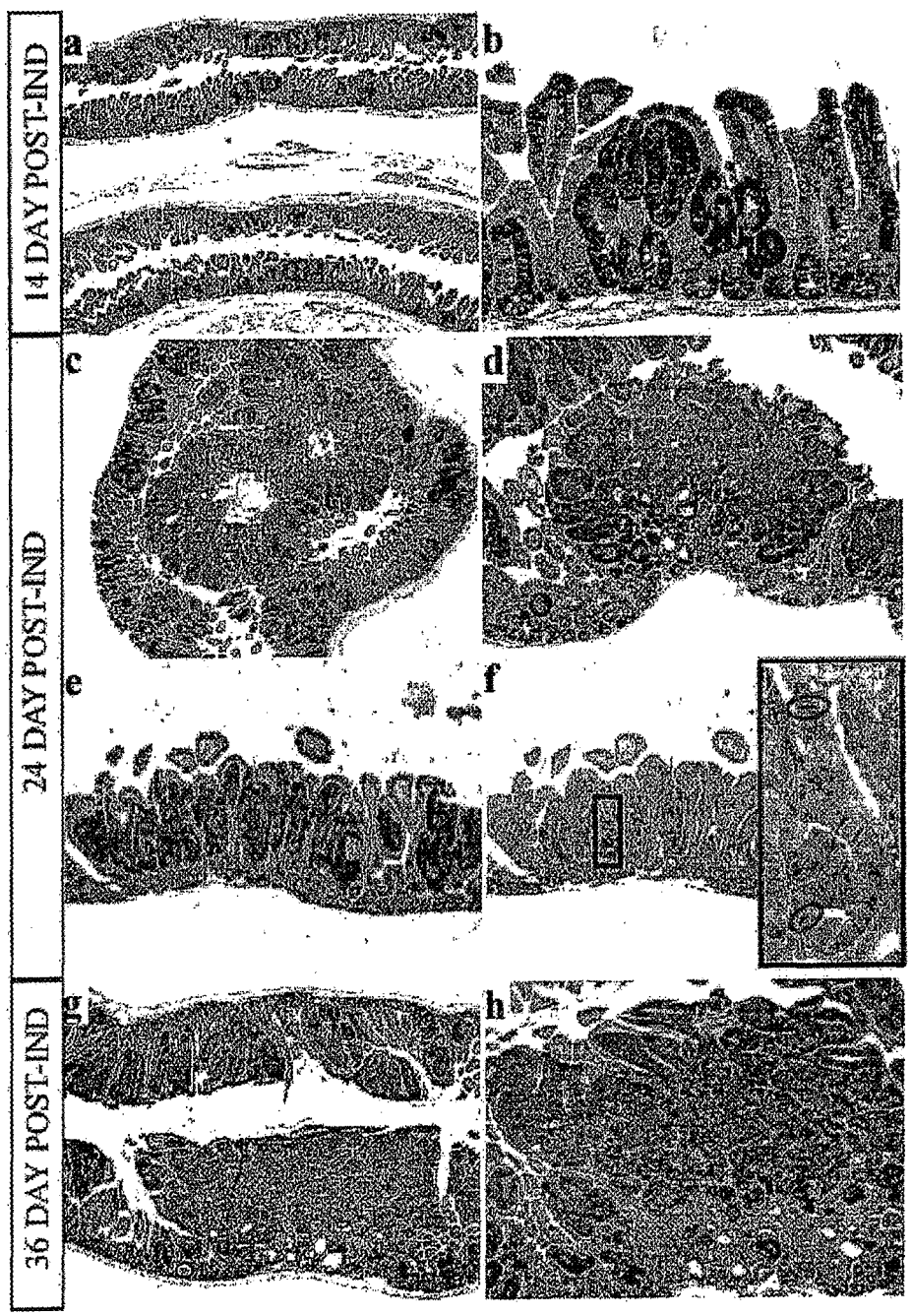

FIG. 22. Selective transformation of Lgr5+ve stem cells following loss of APC efficiently drives adenoma formation throughout the small intestine. a-h: The appearance and development of intestinal adenomas and the expression of the Lgr5-GFP stem cell marker within these adenomas was tracked over a 36 day period using GFP (f) and ß-catenin (all others) IHC.a-b: Multiple small adenomas are readily visible throughout the intestine 14 days after Lgr5+ve stem cell transformation. c-f: Multiple macroscopic adenomas (>100) are present after 24 days. Lgr5-GFP expression in adenomas is restricted to rare scattered cells (f; circled). g,h: At 36 days, a large proportion of the intestine is filled with macroscopic adenomas.

Figure 23:
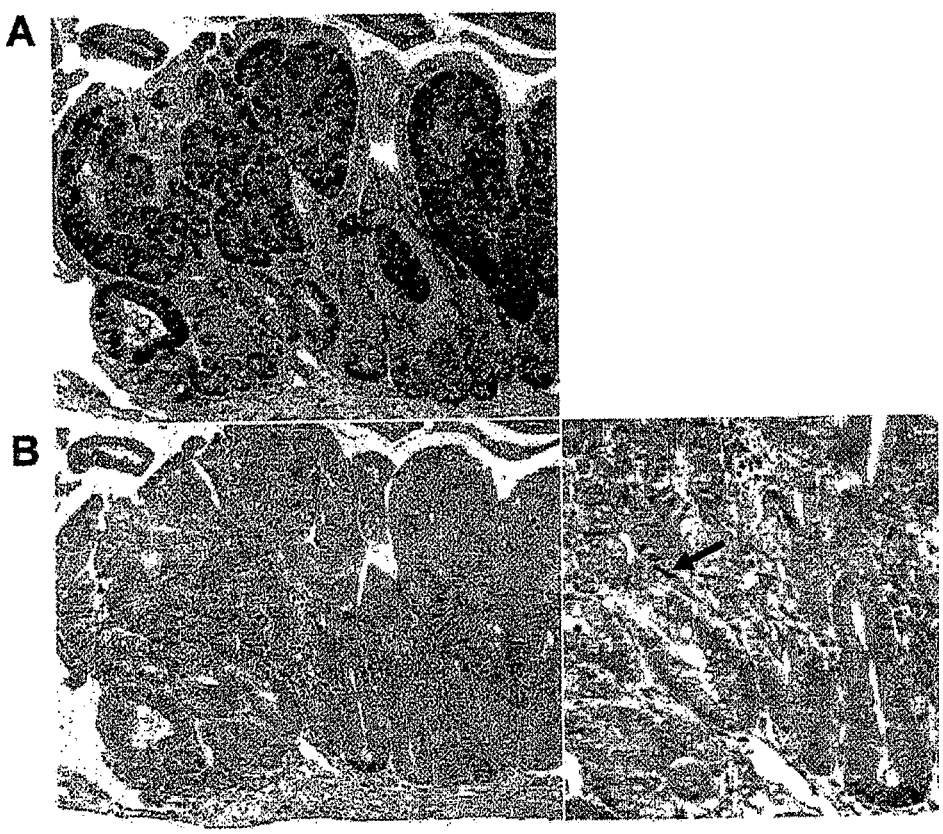

FIG. 23. Presence of Lgr5+ stem cells in intestinal adenomas. Intestinal adenomas express high levels of ß-catenin as a result of chronic activation of the Wnt pathway (A). In contrast to other Wnt target genes which are highly expressed throughout the adenoma (not shown), expression of the intestinal stem cell marker Lgr5-GFP is restricted to scattered cells with characteristic stem cell morphology: slender, comma-shaped cells; indicated with black arrow (B). We speculate that these Lgr5+ve cells within the adenoma are stem cells dedicated to maintaining the growth of the adenoma (so-called cancer stem cells).

Figure 24:
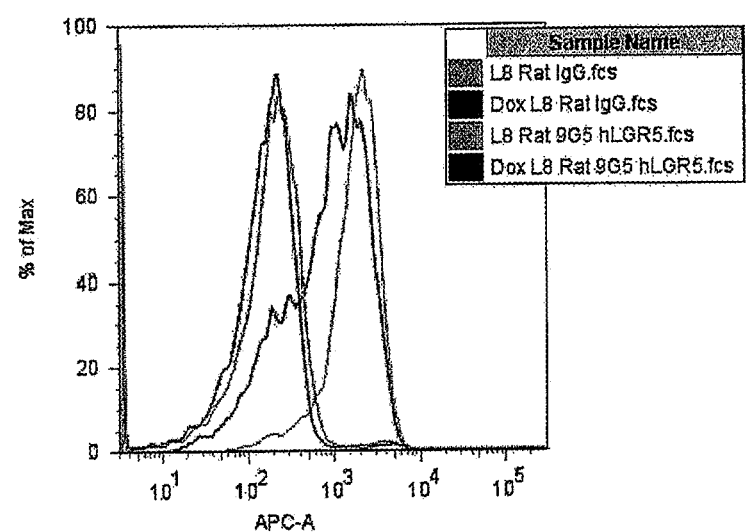

FIG. 24. FACS analyses of LGR5 expression in L8 cells, which are clonal derivatives of LS174T cells, which express dominant negative Tcf4 (DNTcf4) upon Doxycycline (DOX). DNTcf4 turns off constitutive active Wnt pathway. After 48 hrs of DOX induction, a reduction in hLgr5 protein levels is observed. Rat IgG is used as negative isotype control. 9G5 is a rat monoclonal derived antibody directed against hLgr5

Figure 25:
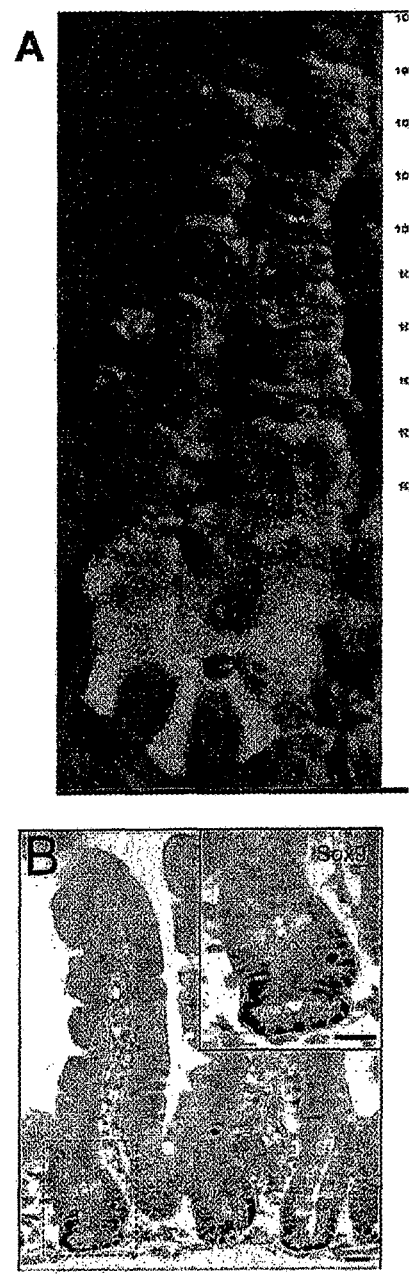

FIG. 25. Comparison of Lgr5+ stem cells and their direct progeny. GFP-positive epithelial cells from cell suspensions prepared from freshly isolated crypts of Lgr5-EGFP-ires-CreERT2 mice. FACS analysis distinguished a GFP-high (GFPhi) and a GFP-low (GFPlo) population, which we tentatively identified as CBC cells and their immediate transit-amplifying daughters, respectively (A). An example of a Wnt-responsive gene, Sox9, which shows high level expression in CBC cells, but TA cells directly above the Paneth cells also express this gene in in situ hybridizations, albeit at a much lower level (B).

Figure 26:
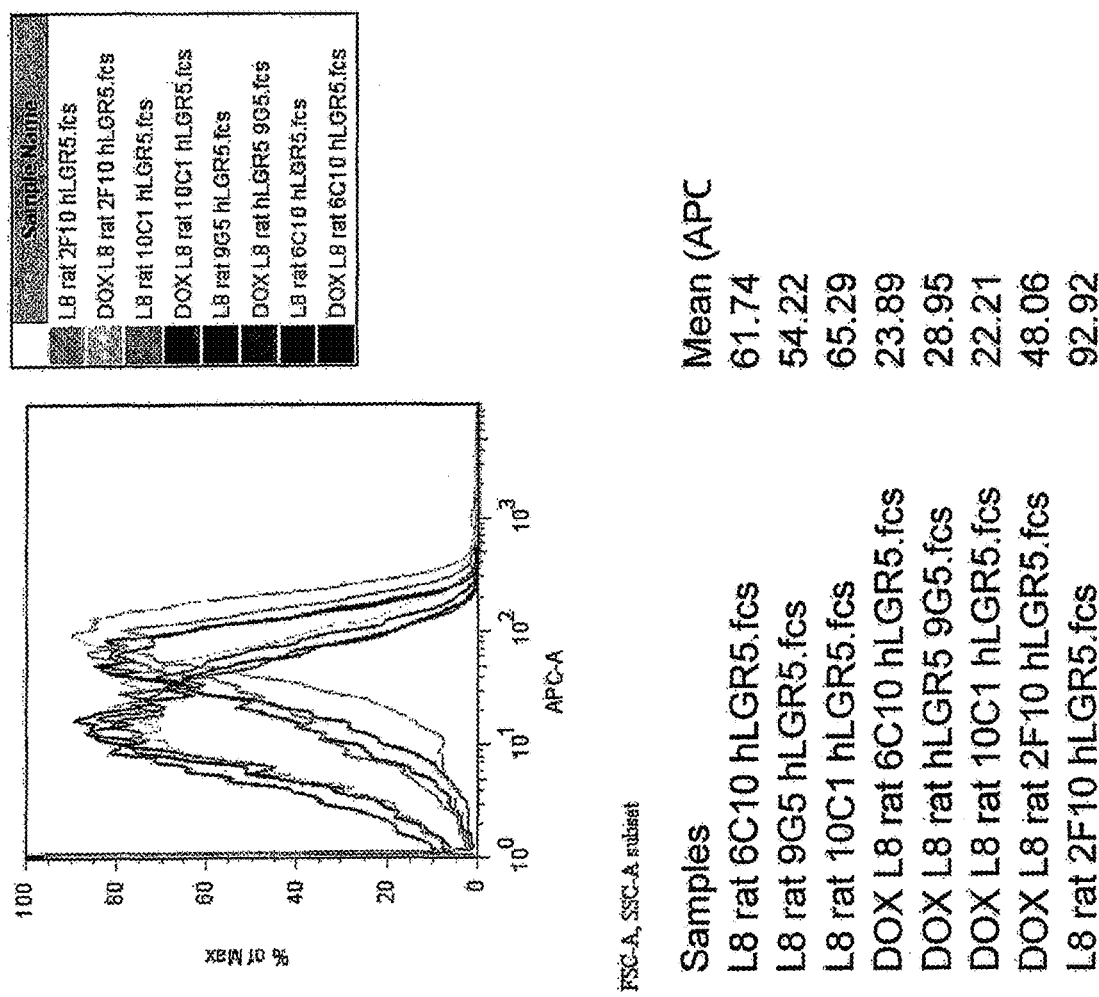

FIG. 26. Endogenous hLgr5 staining of a human colon cancer cell line (L8) using several Lgr5-specific monoclonal antibodies. L8 cells are a clonal derivative of the parental LS174T cell-line. Following Doxycycline (DOX) induction the L8 cells express a dominant-negative form of Tcf-4 (DNTcf4). DNTcf4 efficiently blocks the constitutive Wnt pathway activity in these cells and consequently switches off Tcf target genes. After 48 hrs of DOX induction a major reduction in hLgr5 protein levels is observed. Rat IgG is used as negative isotype control.

FIG. 27. Light chain+heavy chain sequences analyzed using KABAT method. CDR regions are in bold and in italics.

EXAMPLES

Example 1

Experimental Part

Northern blotting and induced Wnt pathway inhibition in LS174T clone L8: As in van de Wetering, M. et al. The beta-catenin/TCF-4 complex imposes a crypt progenitor phenotype on colorectal cancer cells. Cell 111, 241-50 (2002). The probe spanned the entire reading frame of mouse Gpr49. Crypt and villus epithelial preparations for RNA isolation were generated from 0.5 cm lengths of intestine by 4 successive rounds of incubation in pre-warmed 30 mM EDTA at 37° C. for 10 minutes, followed by vigorous shaking (10×) in ice-cold PBS. Fractions 1 and 4, comprising predominantly villi and crypts respectively were used for RNA isolation.

Mice: GPR49-LacZ mice were generated by homologous recombination in ES cells targeting an Ires-LacZ cassette to the 5' end of the last exon, essentially removing the region containing all TM regions and creating a null allele (Lexicon). GPR49-EGFP-Ires-CreERT2 mice were generated by homologous recombination in ES cells targeting an EGFP-Ires-CreERT2 cassette to the ATG of GPR49. Rosa26-lacZ Cre reporter mice were obtained from Jackson Labs.

Tamoxifen induction: Mice of at least 8 weeks of age were injected once intraperitoneally with 200 µl of Tamoxifen in sunflower oil at 10 mg/ml. BrdU injection: Mice were injected intraperitoneally at four hour intervals with 200 µl of a BrdU solution in PBS at 5 mg/ml.

Immuno Electron Microscopy: Intestines were dissected and perfuse-fixed in 4% PFA in 0.2 M PHEM-buffer, embedded in gelatine, cryosectioned with a Leica FCS cryoultratome and immunolabelled against GFP with polyclonal rabbit anti-GFP antibody. Samples were trimmed using a diamond Cryotrim 90 knife at −100° C. (Diatome, Switzerland) and ultrathin sections of 70 nm were cut at −120° C. using a Cryoimmuno knife (Diatome, Switzerland). For the low magnification EM images the 15 nm protein A-gold particles (UMCU, Utrecht, The Netherlands) were briefly silver enhanced with R-GENT SE-EM (Aurion, The Netherlands) according to the manufacturers instructions. Aspecific binding to Paneth cell granules was diminished by applying Blocking solution (Aurion, The Netherlands) prior to the primary antibody.

Tissue sample preparation for immunohistochemistry, in-situ hybridization and LacZ expression analysis: All performed as previously described in Muncan, V. et al. Rapid loss of intestinal crypts upon conditional deletion of the Wnt/Tcf-4 target gene c-Myc. Mol Cell Biol 26, 8418-26 (2006). In-situ probes comprising a 1 kb N-terminal fragment of mGPR49 were generated from sequence-verified Image Clone 30873333. Ki67 antibodies were purchased from Monosan (The Netherlands), Phospho-histone H3 from Campro Scientific (The Netherlands), anti-synaptophysin from Dako, anti BrdU from Roche. Polyclonal rabbit anti-GFP was provided by Edwin Cuppen, Hubrecht Institute.

Generation of Suspension of Human (Tumor) Tissue Cells.

Using a razor blade, mince freshly isolated human (tumor) tissue as much as possible. Do this in serum-free media. Draw minced tumor into a 25 ml pipette. Place the solution into a 50 ml conical tube. Incubate at 37 C for 30-60 min after adding collagenase IV (200 units/ml) (Sigma). The final concentration should be 200 units/ml. Pipette up and down a few times every 10 min (approx). Pass the solution through a filter (45 micrometer pore size; Becton Dickinson). Wash the filter with 4-5 ml of serum-free medium. Centrifuge the solution @ 1500 rpm for 10 min (4° C.) Resuspend the pellet in hypotonic ammonium chloride (approx. 5 ml). Leave 10 min at room temperature (this will lyse red blood cells). Then add equal volume of serum-free media and centrifuge again. Resuspend pellet in serum free medium. If clumpy then pass through another filter. Count with trypan blue to see the percent dead cells.

Cancer Stem Cell Assay by Xenografting in Immunodeficient Mice

The mice are sublethally irradiated with 320 Rad. The experimental procedure involves injecting human (colon) cancer cell suspensions under the renal capsule of NOD/SCID mice. The mice are handled using sterile techniques and anaesthetized using inhalational anaesthesia: isoflurane. The mice are placed on a heating pad during the procedure.

A clipper is used to shave the abdomen, which is then prepped sequentially with: (1) iodine based solution and (2) 70% ethanol solution. The area is then dabbed with a gauze. The mouse is placed on its side (left side up). A 1 cm (approximately) flank incision is made with scissors, just below the costal margin on the left side. Deliver the kidney into the wound. The cell suspension to be assayed for cancer stem cell activity is mixed 1:1 (medium: Matrigel) on ice. Utilizing a tuberculin syringe, inject 25 microliter of the cell suspension under the renal capsule. Deliver the kidney back into the abdomen. If cancer stem cell activity is present in the cell suspension, a tumor will grow out in the subsequent weeks/months which is analysed by histology and should resemble the original human tumor.

The intestinal epithelium is the most rapidly self-renewing tissue in adult mammals. Current models state that 4-6 crypt stem cells reside at the +4 position immediately above the Paneth cells in the small intestine; colon stem cells remain undefined. Gpr49/Lgr5 was selected from a panel of intestinal Wnt target genes for its restricted crypt expression. Two knock-in alleles revealed exclusive expression of Gpr49 in cycling, columnar cells at the crypt base. In addition, Gpr49 was expressed in rare cells in several other tissues including stomach, breast and hair follicle. Using an inducible Cre knock-in allele and the Rosa26-LacZ reporter strain, lineage tracing experiments were performed in adult mice. The Gpr49$^{+ve}$ crypt base columnar cell (CBC) generated all epithelial lineages over a 60-day period, implying that it represents the stem cell of the small intestine and colon. The expression pattern of Gpr49 shows that it marks stem cells in multiple adult tissues and cancers.

The absorptive epithelium of the small intestine is ordered into crypts and villi[1] (References 2). In the mouse, the small intestinal epithelium turns over every 3-5 days. The massive rate of cell production in the crypts is balanced by apoptosis at the tips of the villi. To date, intestinal stem cells have not been functionally identified, due to the lack of unique markers and the absence of stem cell assays. The analysis of mouse chimeras and mutagen-induced somatic clones[2, 3] (References 2) and the study of regeneration upon injury have allowed an operational definition of stem cell characteristics. Stem cells are believed to cycle steadily to produce the rapidly proliferating transit amplifying (TA) cells capable of differentiating towards all lineages. Stem cells self-renew throughout life, and regenerate the epithelium following injury. The estimated number of stem cells is between 4 and 6 per crypt[2] (References 2). Long-term DNA label retention has tentatively located stem cells at "position +4" directly above the Paneth cells[4] (References 2). Three differentiated cell types (enterocytes, goblet cells and enteroendocrine cells) form from TA cells at the crypt-villus junction and continue their migration in coherent bands stretching along the crypt-villus axis. While crypts are monoclonal, each villus receives cells from multiple different crypts and is therefore polyclonal. The fourth major differentiated cell-type, the Paneth cell, resides at the crypt bottom. The colon epithelium contains crypts, but has a flat surface rather than carrying villi. This epithelium comprises two major differentiated cell types: the absorptive colonocytes and the goblet cells' (References 2). To date, no stem cells have been identified in the colon.

Since Wnt signals constitute the major driving force behind the biology of the crypt[5] (References 2), we hypothesized that one or more Wnt/Tcf4(Tcf712) target genes may be specifically expressed in the stem cells. We have previously described the Wnt/Tcf4 target gene program in colorectal cancer cells and found that it is physiologically expressed in intestinal crypts[6, 7] (References 2). When we studied the expression of approximately 80 selected Tcf4 target genes[7], the overwhelming majority was expressed either in Paneth cells or TA cells. The Gpr49/Lgr5 gene, however, was expressed in a unique fashion. The Gpr49 gene behaved as a Wnt target gene, as its expression was extinguished upon the induced inhibition of Wnt pathway activity by dominant-negative TCF4 in the human colorectal cancer cell line LS174T, a cell system described earlier[6] (References 2) (FIG. 1a, lane 1 vs. 2). Accordingly, the gene was expressed in the crypts, but not the villi, of mouse small intestine (FIG. 1a, lane 3 vs. 4). In situ hybridization revealed expression in a limited number of cells located at all crypt bottoms as well as in adenomas in the small intestine of an APC$^{min}$ mouse (FIGS. 1b and c). This expression pattern, enlarged in FIG. 2c, clearly differed from that obtained with a Paneth cell-specific gene (FIG. 2a) or a TA-specific gene (FIG. 2b). The Gpr49 gene appeared to mark small cells interspersed between Paneth cells, the cycling Crypt Base Columnar (CBC) cells (FIG. 2d-h; see below).

Gpr49 encodes an orphan G protein-coupled receptor (GPCR), characterized by a large leucine-rich extracellular domain. It is closely related to GPCRs with glycoprotein ligands, such as the TSH-, FSH- and LH-receptors[8] (References 2). Gpr49 was on our original list of Tcf4 targets in colorectal cancer[6], but has since been observed to be overexpressed also in ovarian and hepatocellular carcinomas[9, 10] (References 2). In order to study its expression in detail we obtained a knock-in allele, in which LacZ, preceded by an internal ribosome entry site (ires), is integrated just N-terminal to the first transmembrane domain essentially creating a null allele (FIG. 3a).

While our study was in progress, Morita et al published the Gpr49$^{-/-}$ phenotype[11] (References 2). A malformation of the tongue and lower jaw causes newborn mutants to swallow large amounts of air leading to their demise soon after birth. We observed the same phenotype in our mice. Of note, crypts and intestinal stem cells are first established several weeks after birth[12] (References 2). The heterozygous Gpr49-LacZ mice allowed us to detail the expression of Gpr49. Before birth, a dynamic and complex expression pattern was observed (Barker et al, in preparation). Around birth, Gpr49 expression subsided in virtually all tissues. Expression in adult mice was restricted to rare, scattered cells in the eye, brain, hair follicle, mammary gland, reproductive organs, stomach and intestinal tract (FIG. 3, and not shown). In the small intestine, Gpr49 expression was observed in slender cells located between the Paneth cells in the small intestine (FIGS. 3b and c) and in a similar number of cells at the bottom of colon crypts (FIGS. 3d and e). Counting of blue cells in small intestinal crypts sectioned through the lumen revealed the presence of approximately 3.5 of such cells per sectioned crypt (FIG. 2i, white bar). More than 30 years ago, Leblond and Cheng noted the presence of cycling cells between the Paneth cells and have coined the term "Crypt Base Columnar" (CBC) cells[13] (References 2). Based on their position and their presence in long-term mutant epithelial clones, Cheng and Bjerknes[2, 14] (References 2) and Gordon and colleagues[15] (References 2) have proposed that these cells may harbor stem cell activity By morphology, the slender Gpr49$^{+ve}$ CBC cells with their scant cytoplasm and flat, wedge-shaped nuclei pointing towards the crypt lumen were readily distinguishable from the adjacent Paneth cells. Occasionally (once in approximately every ten crypts), these cells also expressed the M phase marker phospho-histone H3, indicating that the cells are in cycle (FIG. 2f). Indeed, a 4 hour pulse of BrdU labeled approximately 1 of these cells per crypt (FIGS. 2G and 2I, left black bar), while a 24 hour continuous BrdU labeling resulted in more than 3 positive cells per crypt (FIGS. 2h and i, right black bar), close to the total number of CBC cells per crypt (FIG. 2i, white bar). This observation implied that the average cycling time of CBC cells is in the order of 1 day. Direct colocalization of the proliferation marker Ki67 with GPR49-LacZ further confirmed that the LacZ positive CBC cells are typically cycling (FIG. 2e and FIG. 9).

In order to be able to visualize live CBC cells and to study their potential "sternness", we generated another knock-in allele, in which we integrated an EGFP-ires-CreERT2 cassette at the first ATG codon of Gpr49 (FIG. 4a and FIG. 6). Heterozygous mice carrying this allele were healthy and fertile. The GFP pattern observed in adult tissues faithfully recapitulated the pattern previously seen with the Gpr49-LacZ allele in eye, brain, hair follicle, mammary gland, reproductive organs, stomach and intestinal tract (not shown, and FIG. 4). Confocal imaging allowed the visualization of the Gpr49$^{+ve}$ cells by GFP fluorescence in small intestine (FIG. 4b,c,e) and colon (FIG. 4f). Immuno-Electron Microscopy using immunogold labeling of the GFP-positive CBC cells and of neighbouring Paneth cells and fibroblasts illustrated the unique ultrastructural anatomy of the CBC cells (FIGS. 4g and h). Typically, the CBC cells were relatively broad at their base, contained a flat wedge-shaped nucleus and scarce organelles. A slender extension of apical cytoplasm was squeezed inbetween neighboring endoplasmic reticulum- and granule-rich Paneth cells, extended to the crypt lumen and carried some apical microvilli.

We then crossed the EGFP-ires-CreERT2 knock-in allele with the Cre-activatable Rosa26-LacZ reporter[16] (See FIG. 4a for experimental strategy). Injection of Tamoxifen activates the CreERT2 fusion enzyme in Gpr49-expressing cells. Cre-mediated excision of the roadblock sequence in the Rosa26-LacZ reporter should then irreversibly mark the Gpr49$^{+ve}$ cells. Moreover, while potential progeny of these cells will no longer express GFP, the activated LacZ reporter should act as a genetic mark, facilitating lineage tracing.

LacZ expression was not observed in non-induced mice (not shown). To quantify the total number of CBC cells per crypt in which the latent Cre enzyme could be activated by Tamoxifen, we treated 2-3 months-old mice with Tamoxifen and sacrificed the mice 12 hours later. As evident in FIG. 5a, blue LacZ signals appeared at the typical CBC positions. We determined the frequency at which the blue cells appeared at specific positions relative to the crypt bottom, according to the scheme in FIG. 5b. The large majority of the Cre$^{+ve}$, LacZ-labelled CBC cells occurred at positions between the Paneth cells, while only 10% of these cells were observed at the +4 position directly above the cells (FIG. 5b, blue line). Quantitative data on the position of long term DNA label-retaining cells obtained in adult mice post-irradiation (marking the "+4" intestinal stem cell) were published recently by Potten and colleagues[17]. Comparison of these data (FIG. 5b, red line) with the position of CBC cells with activatable Cre revealed that the two markers identified largely non-overlapping cell populations.

Another defining characteristic of the +4 cell is their exquisite sensitivity to low dose (<1Gy) radiation[4]. To compare relative radiation sensitivity between CBC cells and +4 cells, adult mice were irradiated with 1 Gy or 10 Gy and subsequently sacrificed 6 hours later, at the peak of apoptosis. Active Caspase-3-positive cells were visualized by immunohistochemistry (FIG. 7a). The frequency of positive cells per crypt was determined by counting apoptotic cells in three classes: CBC cells (defined by their location between the Paneth cells), +4 cells (located directly above the Paneth cells) and TA cells: located at position 5-15 (FIG. 7b). Maximal apoptosis at the +4 position was already reached at 1 Gy (a: upper panel, black arrows) in concordance with[4] (References 2), while 10 Gy caused significantly more apoptosis than 1 Gy irradiation in CBC (a: lower panel) and TA cells, confirming the different identities of the CBC and +4 cells.

Adult mice were then subjected to a Tamoxifen pulse and were sacrificed at 1, 5, 12 (not shown) and 60 days post-induction. One day post-induction, occasional CBC cells in the crypts of small intestine and colon were observed to express LacZ (FIGS. 5c and 5i respectively). As is demonstrated for whole-mount small intestine in FIG. 8, parallel ribbons of cells emanated from the crypt bottoms and ran up the side of adjacent villi at later time points. The kinetics of stripe formation was not uniform. Some stripes already reached the villus tips 5 days post-induction, while blue staining in occasional crypts was still restricted to crypts. At 5 days post-induction (FIG. 5d), such crypt-restricted expression was very rarely seen. The CBC cells were capable of long-term maintenance of the self-renewing epithelium, since in 60-day intestines (FIG. 5e and FIG. 8) the frequency of blue crypts and ribbons was essentially identical to that seen at 5-12 days post-induction.

Double-labeling of 60 day-induced intestine demonstrated the presence of PAS-positive goblet cells (FIG. 5f), PAS-positive Paneth cells (FIG. 5g) and synaptophysin-positive enteroendocrine cells (FIG. 5h) in the LacZ-stained clones originating from the GPR49$^{+ve}$ CBC cells. Using mutational marking, Cheng and Bjerknes have reported the existence of different types of long-lived epithelial clones, i.e. columnar (enterocyte) clones, mucous (goblet) clones and mixed clones[2]. The clones observed in our study were exclusively of the mixed variety. In blue clones, the frequency of goblet cells (114 out of 2043 total cells counted), enterocytes (1846/2043) and Paneth cells (83/2043) was comparable to the frequency of goblet cells (127 out of 3691 total cells counted), enterocytes (3345/3691) and Paneth cells (127/3691) in unmarked adjacent epithelium. As noted[2] (References 2), the third secretory cell type, the enteroendocrine cell, was too rare to allow accurate enumeration. Taken together, we conclude that the Gpr49$^{+ve}$ CBC cells represent the genuine stem cells of the small intestine.

Analysis of the colon yielded essentially identical observations. The Gpr49$^{+ve}$ cells yielded blue clones emanating from the crypt bottom (FIG. 5i). These clones contained colonocytes as well as goblet cells, and essentially remained unchanged during the 60 days of chase (FIG. 5j,k). One significant difference with the situation in the small intestine involved the kinetics of clone-formation. At 5 days, blue staining in most crypts was still restricted to the bottom and entirely blue crypts were only rarely observed, implying that the colon stem cells were more often quiescent than their small intestinal counterparts. At later days, the relative number of entirely blue crypts increased. We concluded that the Gpr49$^{+ve}$ colon cells fulfilled the stem cell requirements in being pluripotent and capable of maintaining epithelial self-renewal over long periods of time.

Our observations provide the definitive characterization of the intestinal stem cell by lineage tracing using the expression of a single marker gene, Gpr49. The small intestinal Gpr49$^{+ve}$ cells are generally not quiescent, but are rapidly cycling, as evidenced by the expression of Ki67 and phospho-histone H3, the incorporation of BrdU, and by the kinetics of ribbon formation. Gpr49$^{+ve}$ cells of the small intestine appear more actively dividing than their colonic counterparts, likely reflecting differences in the rate of epithelial turnover between the two organs. It appears somewhat counterintuitive that stem cells cycle. This is, however, not unprecedented. Germ stem cells in the Drosophila testis and ovary of the fly, arguably the best understood adult stem cells in animals, cycle throughout the lifetime of the adult fly[18] (References 2). Similarly, a recent elegant study demonstrated that adult stem cells of mammalian skin are continuously cycling[19] (References 2).

The cycling +4 cells have previously been proposed by Potten and colleagues to represent the small intestinal stem cells[4] (References 2), a notion not confirmed here. The notion was based on the observation that a DNA label incorporated during periods of high stem cell activity was specifically retained in cells at the +4 position. Long-term label retention is often used as an indirect strategy to identify stem cells[12] (References 2). It should be noted, however, that terminally differentiating cells will also retain DNA labels and that label retention should therefore be interpreted with caution. Previous studies have proposed other markers for intestinal stem cells. Musashi[20, 21] (References 2) and CD133[22] (References 2) in our hands stain up to 30-50 cells per crypt (not shown), which appear to encompass CBC cells as well as early transit amplifying cells. Li and colleagues have described several molecular markers for the +4 cells, including phospho-PTEN, phospho-AKT and 14-3-$\zeta$[23] (References 2). Our current study implies that the validity of these putative stem cell markers should be reconsidered.

It appears rather unique that adult stem cells can be identified based on the expression of a single gene. This phenomenon may not be restricted to the intestine, since we observe highly restricted Gpr49 expression in a variety of other tissues. In the anagen hair follicle, the Gpr49 gene is expressed in the bulge area as well as in the outer root sheath (FIG. 3i). While quiescent LTR stem cells reside exclusively in the bulge, activated stem cells migrate down through the outer root sheath towards the basal papilla[24-26] (References 2). Indeed, Gpr49 was recently reported to be the second most highly upregulated gene as assessed by differential expression arraying on isolated hair follicle stem cells[27] (References 2). Moreover, preliminary lineage tracing experiments in the hair follicle support the notion that Gpr49$^{+ve}$ cells represent stem cells (Barker, Clevers and Toftgard, unpublished). While patterns of proliferation in stomach glands have indicated that the epithelial stem cells reside at the isthmus, halfway between the gland base and epithelial surface[28] (References 2) we find Gpr49 expressed at gland bottoms (FIG. 3f,g). Ongoing lineage tracing experiments imply that the entire glands derive from these cells (Barker and Clevers, unpublished). In the mammary gland, stem cells reside in the basal epithelial layer[29] (References 2), where we observe Gpr49 expression (FIG. 3h). Gpr49 may thus represent a more general marker of adult stem cells. If true, the mouse models developed in the course of this study will allow the isolation as well as specific genetic modification of live adult stem cells in a variety of organs. We first identified Gpr49 as a gene expressed in colon cancer cells[6] (References 2). It is expressed in other cancers[9, 10] (References 2) and, as described in the current study, also in premalignant mouse adenomas. Based on the observations reported here, we now know that Gpr49 may mark cancer stem cells ("tumor-initiating cells") in colorectal adenocarcinomas.

Example 2 Lgr5 Tissue Expression and Evidence for Lgr5⁺ Stem Cells in these Tissues Materials and Methods For experimental details, we refer to materials and methods as used in example 1

Results and Discussion

Lgr5 Expression Also Detected in Brain, Retina, Liver and Adrenal Gland

We studied the Lgr5 expression in multiple other tissues in the mice carrying lacZ integrated into the last exon of the Gpr49 gene, removing all transmembrane regions of the encoded Gpr49 protein. We determined that, analogous to colon and small intestine, Lgr5⁺ cells were detected in brain, retina, liver and adrenal gland (FIG. 12). In adult mice, LGR5 is restricted to rare cell populations in the brain (glomeruli of the olfactory bulb and several other poorly defined regions), the eye (inner nuclear layer of the retina), liver (cells surrounding the portal triads) and adrenal gland.

Lineage Tracing in the Stomach, Mammary Gland and Adrenal Gland Proves that Lgr5 is Marking Stem Cell Populations in these Tissues We used the LGR5KI/Rosa26-lacZ mice[16] (See example 1 for experimental strategy) to study the presence of Lgr5⁺ stem cells in multiple other tissues. Injection of Tamoxifen activates the CreERT2 fusion enzyme in Gpr49-expressing cells. Cre-mediated excision of the roadblock sequence in the Rosa26-LacZ reporter should then irreversibly mark the Gpr49⁺ᵛᵉ cells. Moreover, while potential progeny of these cells will no longer express GFP, the activated LacZ reporter should act as a permanent genetic mark, which will be passed on to any descendents of the LGR5+ve cells, allowing us to track their appearance and fate in-vivo.

Lineage tracing was initiated in young LGR5KI/Rosa26-lacZ mice and the stomach epithelium analyzed for LacZ activity after 6 months. LGR5-lacZ positive cells are initially restricted to the base of the glands (FIG. 13a). After 6 months, multiple entirely lacZ-positive glands are visible throughout the stomach (FIG. 13b), demonstrating that the LGR5+ve cells are capable of generating all cell-types on the glandular epithelium over long periods of time.

Similar lineage tracing experiments were performed and the mammary gland epithelium analyzed for LacZ activity over a 3 month period. LGR5-lacZ positive cells are initially restricted to rare basal epithelial cells on virgin glands (FIG. 14a). Following pregnancy, LacZ-positive cells are visible in the basal epithelium of the newly-formed milk glands (FIG. 14b). This demonstrates that LGR5⁺ cells in the mammary gland are myoepithelial stem cells.

Lineage tracing in the adrenal glands analyzed for LacZ activity over a 3 month period. LGR5-lacZ positive cells are initially restricted to the periphery of the adrenal gland 5 days after induction (FIG. 15a). After 3 months the majority of the adrenal medulla is LacZ positive (FIG. 15b). This remains positive over a 14 month period (not shown). This demonstrates that the LGR5⁺ cells are the stem cells of the adrenal medulla.

Example 3 Lgr6 Tissue Expression and Lgr6 Expression in Related Stem Cells

Material and Methods

Transgenic Mice and Treatments.

Lgr6-EGFP-Ires-CreERT2 mice were generated by homologous recombination in embryonic stem cells targeting an EGFP-Ires-CreERT2 cassette to the ATG of Lgr6. Rosa26-LacZ reporter mice were obtained from the Jackson laboratory. Mice were fed ad libitum. The Cre recombinase was activated in Lgr6-EGFP-Ires-CreERT2/Rosa26-LacZ mice by injecting 200 μl of tamoxifen (10 mg/ml dissolved in sunflower oil) intraperitoneally.

Confocal Analysis of EGFP Expression

For confocal imaging the skin samples were fixed in formalin for 15 minutes at RT and embedded in 4% low melting agarose. Longitudinal sections between 100 and 200 μM thick were prepared using a vibratome. Sections were then permeabilized in PBS supplemented with 1% BSA+1% DMSO+0.1% TritonX, stained for 30 minutes with TO-PRO 1:1000 dilution (Molecular Probes) and embedded using Vectashield (Vector Labs). Sections were imaged with a Sp2 confocal microscope (Leica) and processed using Volocity and Photoshop CS2 software.

Detection of Beta-Galactosidase Activity

Freshly obtained tissues were fixed for 2 hours in 1% Formaldehyde/0.2% glutaraldehyde/0.02% NP40 in PBS0 solution at 4° C. on a rolling platform. Samples were washed 3 times for 20 min with rinse buffer (2 mM $MgCl_2$/0.02% NP40/PBS0) and stained for 36-48 h in a solution consisting of 1 mg/ml X-gal, 5 mM ferrothiocyanide, 5 mM ferrithiocyanide, 0.1% sodium deoxycholate in rinse buffer. The substrate was removed and the samples washed twice in PBS0 for 20 min at room temperature on a rolling platform. The tissues were then fixed overnight in 4% PFA in PBS0 at 4° C. in the dark on a rolling platform. The PFA was removed and the tissues washed twice in PBS0 for 20 min at room temperature. The samples were embedded in paraffin, sectioned (4 μm) and counterstained with neutral red.

Results and Discussion

To characterize the expression of Lgr6 in the skin we utilized a knock-in mouse, where the Lgr6 promoter controls the expression of EGFP and the CreERT2 fusion protein, termed Lgr6-EGFP-Ires-CreERT2. At P25 when the hair follicles (HFs) are in the growing (anagen) phase, the GFP-positive cells were localized to cells of the upper bulge/isthmus area of the HF (FIG. 16A, C) and basal cells of the interfollicular epidermis (IFE, FIG. 16A, B). This expression pattern suggests that Lgr6 expression marks a SC/early progenitor cell population of the hair follicle and the epidermis.

To address the question whether the Lgr6⁺ cells of the anagen HF and IFE represent functional stem cells 20 day-old Lgr6-EGFP-Ires-CreERT2/Rosa26-LacZ mice were injected with tamoxifen. At P20 Lgr6 is expressed in the upper bulge/isthmus area of the HF and basal cells of the IFE (data not shown). Three days post tamoxifen injection a scattered pattern of labeled cells could be seen in the HFs and the IFE (FIG. 17B). At 18 days post-injection the progeny of Lgr6⁺ cells could be seen in the anagen HFs (FIG. 17C, D) as well as in the IFE and the sebaceous glands (SG) (FIG. 17C, D). In the next telogen labeled cells were found in the bulge and isthmus of the HFs (FIG. 17E, F) and the IFE and SGs (FIG. 17E, F). This observation strongly suggests that Lgr6⁺ cells located in the bulge/isthmus area of the HF and the basal IFE exhibit stem cell properties. In particular, Lgr6⁺ cells can contribute to all the appendages of the skin, i.e. the growing HFs, the IFE and the SG.

It seems rather unique that adult stem cells can be identified on the basis of expression of a single gene, in this case Lgr6. This phenomenon may not be restricted to the skin, because we observe highly restricted expression of Lgr6 in a variety of other tissues. To address the question whether the Lgr6⁺ cells represent functional stem cells in any other tissues 20 day-old Lgr6-EGFP-Ires-CreERT2/Rosa26-LacZ mice were injected with tamoxifen. LacZ staining was performed on 18 and 32 days post tamoxifen injection to assess for lineage tracing in a variety of tissues. Interestingly, LacZ positive cells were present in the myoepithelium underlying the bronchioles of the lung at both timepoints (FIG. 18). Thus, Lgr6+ cells contribute to the myoepithelium of the lung strongly suggesting that Lgr6+ cells located in the lung exhibit stem cell properties as well.

Example 4 the Role of Lgr5+ Cancer Stem Cells in Adenoma

The anatomy of the intestinal crypt is uniquely suited to study adult stem cells in their niche. The epithelium of the murine small intestine renews every five days[1,2] (references 5). Vigorous proliferation occurs within the crypt compartment. We have recently identified slender, undifferentiated cells expressing the Lgr5 gene located at crypt bottoms as the stem cells of the small intestine and colon. Each small intestinal crypt contains approximately 6 independent, long-lived stem cells that are intermingled with Paneth cells in the small intestine and with goblet cells in the colon. Counterintuitively, these cells are not quiescent, but complete a cell cycle every day[3] (references 5). Leblond and colleagues have originally named these cells morphologically Crypt Base Columnar (CBC) cells[4,5] (references 5). Their daughter cells constitute the readily distinguishable transit amplifying (TA) crypt compartment. TA cells divide every 12-16 hours, generating some 300 cells per crypt every day[6] (references 5). Newly-formed TA cells reside within crypts for approximately 48-72 hours, undergoing up to 6 rounds of cell division while migrating upwards[6] (references 5). When the committed TA cells reach the crypt-villus junction, they rapidly and irreversibly differentiate. The proliferation is balanced by apoptosis at the other end of the epithelial conveyor belt, the tip of the villus. Only Paneth cells escape this flow; they have a residence time of 3-6 weeks at the crypt base[7-9] (references 5). Initiating mutation in intestinal malignancies in mouse and man target components of the Wnt pathway, most frequently the negative Wnt regulator APC[10,11] (references 5). This results in the constitutive activation of a Wnt target gene program that drives the formation of benign adenomas or polyps[12-15] (references 5). However, it remains unclear which cell type sustains the cancer-initiating mutation.

The Cytochrome P450-promoter-driven AH-Cre mouse allows conditional deletion of foxed alleles in the intestinal epithelium following administration of the inducing agent, ß-Napthoflavone (B-NF). Importantly, the AH-Cre allele is highly active in all cell types of the epithelium, including the stem cells[16] (references 5). We have previously employed a floxed allele of APC[17] (references 5) in combination with the AH-Cre mouse line to demonstrate that acute loss of APC throughout the adult intestinal epithelium following IP injection of ß-NF leads to an immediate quantitative transformation of the epithelium[16] (references 5), a process almost entirely dependent on the downstream Wnt target gene c-Myc[18] (references 5). High-dose oral ß-NF induces more stochastic deletion of APC, resulting in rapid adenoma formation throughout the intestine within 3 weeks[19] (references 5). Both these high-dose induction protocols effect deletion in all compartments of the epithelium, including the stem cells at the crypt base.

Having validated the AHCre/APC$^{flox/flox}$ mouse as an inducible model of intestinal cancer, we sought to dissect the mechanism of adenoma formation by identifying its cell-of-origin. We reasoned that oral administration of low-dose ß-NF would restrict its range of action to cells on the villi and the upper regions of the crypts. Careful titration of the required dosage revealed that following oral administration of 1 mg/kg ß-NF, the efficiency of Cre activation in the stem cells at the crypt base was extremely low, as measured by the negligible frequency of long-term lineage tracing initiated in AHCre/R26R mice receiving this dose. This dose was still very efficient in inducing Cre activity in the TA compartment and villus epithelium, as detected using the Rosa26-LacZ mouse[20] (references 5) as a Cre reporter (FIG. 19a, b). In a typical experiment over 70% of villi contained blue cells 2 days after induction, but at day 7 blue staining could no longer be detected. In line with this, no crypt/villus ribbons were detected at day 100 post-oral induction (FIG. 19c).

Using this dosing regime on AHCre/APC$^{flow/Flox}$/R26R mice, multiple ß-catenin$^{high}$ foci/lesions rapidly became visible throughout the upper crypt and villus epithelium. Representative pictures taken at day 3 post-induction are given in FIG. 20. Mutant APC foci evident by high ß-catenin levels occurred predominantly at crypt-villus junctions, but were also seen on the villi (FIG. 19d). Very infrequently these lesions were also seen near the crypt base.

The majority of the APC-deficient cells present on the villus epithelium were lost after 4-5 days, presumably by shedding. The remaining APC-deficient lacZ-positive lesions/foci present within the crypts failed to expand over a 24 day period. A typical example of such a lesion is given in FIG. 20e. No macroscopic adenomas were visible at this stage. Strikingly, these small lesions persisted over a 180 day period (FIG. 20g), and only very rarely progressed to small adenomas, which did not expand beyond 2-3 villi (FIG. 20f, h). This was in stark contrast to the high frequency formation of large adenomas initiated in the AHcre/APC$^{flox/flox}$. mice following high-dose ß-NF induction. This suggested that the vast majority of adenomas in the latter mice resulted from loss of APC in stem cells.

In order to formally prove that transformation of intestinal stem cells is the major route to adenoma formation, we employed our Lgr5-EGFP-ires-CreERT2 knock-in mice as a stem cell-specific Cre line to inducibly delete the foxed APC. To this end, Lgr5-EGFP-ires-CreERT2×APC$^{flox/flox}$ mice were generated. In these mice, the stem cell-specific Cre enzyme was activated with a single IP injection of Tamoxifen (FIG. 21a). Subsequent phenotypic changes in the intestine were tracked over a 2 month period. Accumulation of the Wnt-effector protein ß-catenin was first observed in isolated CBC cells at the crypt base after 3 days (FIG. 21a). These transformed cells were GFP-positive, confirming the targeted deletion of APC in the intestinal stem cells (FIG. 21b). After 5 days, multiple crypts throughout the intestine were observed to harbor transformed (i.e. ß-catenin$^{high}$) stem cells in association with highly proliferative clusters/pockets of ß-catenin$^{high}$ cells within the transit-amplifying (TA) compartment (FIG. 21c, d). This indicated that the Wnt-transformed stem cells remain viable and rapidly generate an expanding population of transformed progeny higher up the crypts. Eight days after inducing APC deletion in the stem cells, the "pockets" of transformed cells had continued to expand within the crypts and outpockets/evaginations of the crypt epithelium and small microadenomas within the associated villus stroma became evident (FIG. 21e). Cells with accumulated ß-catenin were never present on the villus epithelium in these mice, demonstrating that the expanding transformed population were restricted to the intestinal crypts. These observations are strikingly reminiscent of a model of adenoma formation, in which Wnt-transformed cells expressing high levels of the Wnt target gene EphB2 and -B3 expand within the crypt until they come into contact with the Ephrin-positive villus epithelium[21,22] (references 5). The resulting repulsive forces consequently dictate that the microadenoma can only continue to expand by invading the stroma of the neighbouring villus where it is shielded from the Ephrin-positive villus epithelium.

The "outpockets" and microadenomas present in the 8 day induced Lgr5KI/APC$^{flox/flox}$ mice continued their aggressive expansion, as evidenced by the presence of multiple large adenomas throughout the intestine 36 days after initiating stem cell transformation (FIG. 21*f*).

To further investigate the hierarchy that exists between the APC-deficient stem cells and their transformed progeny, we examined expression of the stem cell marker protein Lgr5-EGFP during the various stages of adenoma formation in our model. In non-transformed stem cells, Lgr5-EGFP expression was restricted to the Crypt Base Columnar (CBC) cells (FIG. 22*a*). Expression of this stem cell marker was maintained following the initial transformation of the stem cells after 3 days (FIG. 22*b*) and was also clearly evident in the "pockets" of recently expanded transformed progeny within the crypts after 8 days (FIG. 22*c*), indicating that at least some aspect of "stemness" was conferred to these cells. However, there was a marked down-regulation of Lgr5-EGFP expression on the larger adenomas present in the intestines of 36-day induced mice, despite uniformly high ß-catenin levels throughout the tumor (FIG. 22*d*). Lgr5-EGFP expression was limited to a few scattered cells within the tumor mass (FIG. 23). These GFP-positive cells retained the slender, wedge-shaped morphology characteristic of the CBC intestinal stem cells. It is therefore tempting to speculate that the Lgr5 expression in larger adenomas is marking a rare population of stem cells responsible for fueling their continued growth. Taken together, these data demonstrate that transformation of stem cells through loss of Apc is an extremely efficient route towards initiating intestinal adenoma formation. The kinetics of this process suggest that no further mutations are required once both Apc alleles are lost in intestinal epithelium, which is in accordance with the tissue-tropism of Apc's tumor suppressor activity.

Example 5 Generation and Use of Antibodies Directed Against LGR5 and LGR6

Materials and Methods

Monoclonal rat antibodies were generated by Genovac (Freiburg, Germany) by intramuscular injection of rats with an expression plasmid expressing either human Lgr5 or Lgr6. Rat B-cells were fused with mouse myeloma cells. The resulting hybridomas were screened on HEK293 cells that were transfected with human or Mouse Lgr5 or Lgr6 expression plasmids.

L8 (DNTcf4-LS174T) cells were cultured with and without Doxycycline for 48 hrs. L8 cells are clonal derivatives of LS174T cells. Upon Doxycycline (DOX) induction the L8 cells express a dominant negative form of T-cell Factor 4 (DNTcf4; see Roose et al., 1999, Science 285: 1923-1926). DNTcf4 turns off constitutive active Wnt pathway. Rat IgG was used as negative isotype control. After 48 hrs cells are washed with ice cold PBS and brought into suspension using 5 mM EDTA. All the following steps are done at 4° C. Cells were blocked for 30 min in PBS containing 2% BSA. Primary (1st) and Secondary (2nd) antibody reagent were incubated subsequently for 1 hr, and washed with ice cold PBS/2% BSA. For the primary antibody staining we used undiluted hybridoma supernatant, 2nd antibody staining was done using Qdot® 655 goat F(ab')2 anti-rat IgG conjugates (H+L) (Molecular Probes/Invitrogen). Prior to analysis propidium iodine was added to exclude dead cells in the analysis.

Results

The specificity of some of the isolated antibodies is shown in Tables 4 and 5, as tested by FACS analysis. 9G5 is a rat monoclonal antibody directed against hLgr5. The analysis of endogenous Lgr5 expression was determined in L8 cells. L8 cells are clonal derivatives of LS174T cells. Upon Doxycycline (DOX) induction, L8 cells express dominant negative Tcf4 (DNTcf4). DNTcf4 turns off constitutive active Wnt pathway. This is reflected in FIG. 24, showing FACS staining of L8 cells with 9G5 antibody or IgG control antibody. After 48 hrs of DOX induction, indeed a reduction in endogenous hLgr5 protein levels was observed, as also becomes clear from the reduction in the fluorescent means of the peak for the L8 cells treated with doxycycline.

This experiment was also performed with LGR5-specific antibodies 2F10, 10C1 and 6C10. As shown in FIG. 26, similar results are obtained with any of these LGR5-specific antibodies.

TABLE 4

Specificity of Lgr5 antibodies. 9G5 recognize both mouse and human Lgr5. The colon cancer cell lines; DLD1 and SW480, LIM1863 do not show specific staining for Lgr5. These antibodies were tested negative for cross reactivity against mouse Lgr4, 6 and human Lgr4, and 6.

|  | mLgr5-293T overexpression | hLgr5-293T overexpression | LS174 | L8 (DNTcf4-LS174) |
|---|---|---|---|---|
| NR 1D9 | − | + | + | + |
| NR 2F10 | − | + | + | + |
| NR 4D11 | − | + | + | + |
| NR 6C10 | − | + | + | + |
| NR 9B3 | − | + | + | + |
| NR 3A4 | − | + | + | + |
| NR 5A7 | − | + | + | + |
| NR 6G2 | − | + | + | + |
| NR 9G5 | ++ | ++ | ++ | ++ |
| NR 2B8 | − | ++ | ++ | ++ |
| NR 3B9 | − | ++ | ++ | ++ |
| NR 5C8 | − | + | + | + |
| NR 7B11 | − | + | + | + |
| NR10C1 | − | + | + | + |
| NR 4D6 | − | + | + | + |
| NR 5E9 | − | + | + | + |
| NR 8F2 | − | ++ | ++ | ++ |
| NR10F7 | − | + | + | + |

TABLE 5

Specificity of Lgr6 antibodies. Antibodies 1d8 and 3d8 recognize mouse Lgr6 and hLgr5 in addition to human Lgr6. The colon cancer cell lines; LS174, DLD1 and SW480 do not show specific staining for Lgr6. These antibodies were tested negative for cross reactivity against mouse Lgr4, 5 and human Lgr4.

|  | Clone number | | | | | |
|---|---|---|---|---|---|---|
|  | 1d8 | 3d8 | 6d8 | 2f4 | 2h10 | 5e10 |
| hLgr5-293T overexpression | + | + | − | − | − | − |
| mLgr6-293T overexpression | + | + | − | − | − | − |
| hLgr6-293T overexpression | ++ | ++ | ++ | ++ | + | ++ |

TABLE 5-continued

Specificity of Lgr6 antibodies. Antibodies 1d8 and 3d8 recognize mouse Lgr6 and hLgr5 in addition to human Lgr6. The colon cancer cell lines; LS174, DLD1 and SW480 do not show specific staining for Lgr6. These antibodies were tested negative for cross reactivity against mouse Lgr4, 5 and human Lgr4.

| | Clone number | | | | | |
|---|---|---|---|---|---|---|
| | 1d8 | 3d8 | 6d8 | 2f4 | 2h10 | 5e10 |
| LS174 | − | − | − | − | − | − |
| L8 (LS174-DNTcf4) | − | − | − | − | − | − |

Example 6 Expression Analysis of Colon and Small Intestine Derived Stem Cells Compared to their Direct Progeny Materials and Methods Isolation of GFP Positive Epithelial Cells Freshly isolated small intestines or colons were incised along their length and villi (in case of small intestine) were removed by scraping. The tissue was then incubated in PBS/5 mM EDTA for 5 minutes. Gentle shaking removed remaining villi and the intestinal tissue was subsequently incubated in PBS/EDTA for 30 minutes at 4° C. Vigorous shaking yielded free crypts which were incubated in PBS supplemented with Trypsine (10 mg/ml) and DNAse (0.8 u/μl) for 30 minutes at 37° C. After incubation, cells were spun down, resuspended in SMEM (Invitrogen) and filtered through a 40 μM mesh. GFP-expressing cells were isolated using a MoFlo cell sorter (DAKO).

Microarray Analysis

RNA was isolated from the $GFP^{hi}$ and $GFP^{lo}$ cell fractions of intestines from Lgr5-EGFP-ires-CreERT2 mice. 250 ng of total RNA was labeled using low RNA Input Linear Amp kit (Agilent Technologies, Pato Alto, Calif., USA). Labeling, hybridization, and washing protocols were done according to guidelines (Agilent Technologies, Santa Clara, Calif., USA). Differentially labelled cRNA from $GFP^{hi}$ and $GFP^{lo}$ cells from two different sorts (each combining three different mice) were combined and hybridised on 4X44K Agilent Whole Mouse Genome dual colour Microarrays (G4122F) in two dye swap experiments, resulting in four individual arrays. All data analyses were performed using ArrayAssist (Stratagene Inc, La Jolla, Calif., USA) and Microsoft Excel (Microsoft Corporation, Redmond, Wash., USA). Raw signal intensities were corrected by subtracting local background. Negative values were changed by a positive value close to zero (standard deviation of the local background) in order to allow calculation of rations between intensities for features only present in one sample ($GFP^{hi}$ or $GFP^{lo}$). Data were filtered if both ($GFP^{hi}$ or $GFP^{lo}$) intensities were changed or if both intensities were less than two time the background signal and normalized by a Loess algorithm. Statistical analysis was performed by running an Excel version of SAM (Significant Analysis of Microarrays) using an Excel plug-in of the software (Tusher PNAS 2001, References 6) and "one class" as the response value. Genes were considered to be significantly enriched in $GFP^{hi}$ cells if they had a q-value of <0.1 and where present in at least 3 out of 4 arrays and the average of all four arrays exceeded a log 2 ration of 0.6.

Results

In order to define a gene expression profile for $Lgr5^+$ intestinal stem cells, we established a protocol to sort GFP-positive epithelial cells from cell suspensions prepared from freshly isolated crypts of Lgr5-EGFP-ires-CreERT2 mice (see Methods). FACS analysis distinguished a GFP-high ($GFP^{hi}$) and a GFP-low ($GFP^{lo}$) population, which we tentatively identified as CBC cells and their immediate transit-amplifying daughters, respectively (FIG. 25). A single mouse intestine routinely yielded several hundred thousand $GFP^{hi}$ and $GFP^{lo}$) cells. An example of an almost pure population of Lgr5-expressing cells is provided in FIG. 25A. In order to identify novel stem cell genes, mRNA samples of the two populations were subjected to comparative gene expression profiling. The gene that was most highly enriched in the $GFP^{hi}$ cells was, satisfactorily, the Lgr5 gene itself. Multiple genes on the list (Table 6) were already identified as intestinal Wnt target genes previously, for instance in human colon cancer (van der Flier et al, 2007, Gastroenterology 132, 628-632), which further validated the gene list. While in situ hybridizations on these Wnt target genes typically confirmed high level expression in CBC cells, TA cells directly above the Paneth cells also expressed these genes, albeit at a much lower level. As an example, FIG. 25B shows the expression of Sox9, a Wnt-responsive gene (Blache et al., 2004) crucial for Paneth cell specification (Bastide et al., 2007; Mori-Akiyama et al., 2007).

DISCUSSION

In the intestine, a long-lived pool of cycling stem cells is defined by Lgr5 expression, a Wnt responsive orphan G-coupled receptor (Barker et al., 2007, Nature 449, 1003-1007). These $Lgr5^+$ cells have previously been observed by Leblond and colleagues, who named them Crypt Base Columnar (CBC) cells and already speculated that these CBC cells represent the stem cells of the intestinal epithelium (Cheng and Leblond, 1974, Am J Anat 141, 461-79). Here, we define a minimal gene expression profile for these CBC cells by exploiting the Lgr5-EGFP-ires-CreERT2 knock-in mice for sorting, based on GFP expression. We defined a set genes differently expressed between $GFP^{hi}$ and $GFP^{lo}$ fractions. Based on confocal images of isolated crypts, we tentatively identified these as CBC cells and their daughters, respectively. Lgr5 was found as the most differential gene in this set, implying that its expression is strongly restricted to CBC cells. Many other genes in the signature represented previously identified Wnt-dependent genes, e.g. Ascl2, CD44, Ephb3, Sox9 and Spy (van der Flier et al, 2007, Gastroenterology 132, 628-632). Given the intimate connection between Wnt signaling and the biology of stem cells in many tissues (Reya and Clevers, 2005, Nature 434, 843-850), this was not surprising.

Table 6 Expression Analysis of Stem Cells and their Direct Progeny

Small intestinal (Table 6a) and colon stem cell (Table 6b) signature based on Lgr5 expression. GFP-positive epithelial cells from pure crypt preparations of Lgr5-EGFP-ires-CreERT2 mice were isolated using FACS sorting. FACS analysis distinguished two populations $GFP^{hi}$ and $GFP^{lo}$ cells, corresponding to the CBC cells and their immediate transit-amplifying daughters respectively. In order to identify novel stem cell genes, mRNA samples of the two populations were subjected to comparative gene expression profiling using Agilent microarray analysis.

TABLE 6a

Comparison of small intestinal stem cells with direct progeny

| Gene name | avg log2 ratio[1] (gfp$^{high}$/gfp$^{low}$) |
|---|---|
| Lgr5 | 2.54 |
| Ephb3 | 1.38 |
| Cd44 | 1.15 |
| Rnf43 | 1.14 |
| Sox9 | 1.12 |
| Slc12a2 | 0.87 |
| Ets2 | 0.80 |

[1]Q value <0.15

TABLE 6b

Comparison of colon stem cells with direct progeny

| Gene name | avg log2 ratio[1] (gfp$^{high}$/gfp$^{low}$) |
|---|---|
| Lgr5 | 2.98 |
| Cd44 | 1.47 |
| Cdca7 | 1.23 |
| Ephb3 | 1.11 |
| Myb | 0.81 |
| Myc | 0.77 |

[1]Q value <0.05

Example 7 Sequence Determination of Light Chain and Heavy Chains, Including CDR Regions, of LGR5-Specific/LGR6-Specific Antibodies Materials and Methods:

Hybridoma Sequence

The hybridomas were produced as described in the materials and methods section of Example 5.

Hybridoma sequences were determined from Lgr5-specific and/or Lgr6-specific clonal hybridoma cell lines NR 2F10 (see Table 4) and 6d8 and 2f4 (see Table 5). Total RNA was isolated using Trizol reagent and cDNA generated using superscript reverse transcriptase (Promega). cDNA was amplified using PCR primers designed to amplify the IgG antibody Fv-DNA sequences in a 'touch-down' PCR. PCR fragments were cloned into either PJET1.2 (Fermentas) or PGEM-T (Promega) cloning vectors and subsequently sequenced using vector-specific primers on an ABI sequencer.

IgG Antibody Fc-DNA Sequence PCR Primers:

Kappa L-chain reverse primers; 25 individually synthesized oligos, pooled, representing 50 variants:

MVK-1
(SEQ ID NO: 1)
GACATTGTTCTCACCCAGTCTCC

MVK-2
(SEQ ID NO: 2)
GACATTGTGCTSACCCAGTCTCC

MVK-3
(SEQ ID NO: 3)
GACATTGTGATGACTCAGTCTCC

MVK-4
(SEQ ID NO: 4)
GACATTGTGCTMACTCAGTCTCC

MVK-5
(SEQ ID NO: 5)
GACATTGTGYTRACACAGTCTCC

MVK-6
(SEQ ID NO: 6)
GACATTGTRATGACACAGTCTCC

MVK-7
(SEQ ID NO: 7)
GACATTMAGATRACCCAGTCTCC

MVK-8
(SEQ ID NO: 8)
GACATTGCAGATGAMCCAGTCTCC

MVK-9
(SEQ ID NO: 9)
GACATTCAGATGACDCAGTCTCC

MVK-10
(SEQ ID NO: 10)
GACATTCAGATGACACAGACTAC

MVK-11
(SEQ ID NO: 11)
GACATTCAGATGATTCAGTCTCC

MVK-12
(SEQ ID NO: 12)
GACATTGTTCTCAWCCAGTCTCC

MVK-13
(SEQ ID NO: 13)
GACATTGTTCTCTCCCAGTCTCC

MVK-14
(SEQ ID NO: 14)
GACATTGWGCTSACCCAATCTCC

MVK-15
(SEQ ID NO: 15)
GACATTSTGATGACCCARTCTC

MVK-16
(SEQ ID NO: 16)
GACATTKTGATGACCCARACTCC

MVK-17
(SEQ ID NO: 17)
GACATTGTGATGACTCAGGCTAC

MVK-18
(SEQ ID NO: 18)
GACATTGTGATGACBCAGGCTGC

MVK-19
(SEQ ID NO: 19)
GACATTGTGATAACYCAGGATG

MVK-20
(SEQ ID NO: 20)
GACATTGTGATGACCCAGTTTGC

MVK-21
(SEQ ID NO: 21)
GACATTGTGATGACACAACCTGC

MVK-22
(SEQ ID NO: 22)
GACATTGTGATGACCCAGATTCC

MVK-23
(SEQ ID NO: 23)
GACATTTTGCTGACTCAGTCTCC

MVK-24
(SEQ ID NO: 24)
GACATTGTAATGACCCAATCTCC

-continued

MVK-25
(SEQ ID NO: 25)
GACATTGTGATGACCCACACTCC

Kappa L-Chain Forward Primer:

mck-1
(SEQ ID NO: 26)
ACACTCATTCCTGTTGAAGCTCTTGAC

H-chain variable region reverse primers, 25 individually synthesized oligos, pooled, representing 88 variants:

MVH-1
(SEQ ID NO: 27)
GCCGGCCATGGCCGAGGTRMAGCTTCAGGAGTCAGGAC

MVH-2
(SEQ ID NO: 28)
GCCGGCCATGGCCGAGGTSCAGCTKCAGCAGTCAGGAC

MVH-3
(SEQ ID NO: 29)
GCCGGCCATGGCCCAGGTGCAGCTGAAGSASTCAGG

MVH-4
(SEQ ID NO: 30)
GCCGGCCATGGCCGAGGTGCAGCTTCAGGAGTCSGGAC

MVH-5
(SEQ ID NO: 31)
GCCGGCCATGGCCGARGTCCAGCTGCAACAGTCYGGAC

MVH-6
(SEQ ID NO: 32)
GCCGGCCATGGCCCAGGTCCAGCTKCAGCAATCTGG

MVH-7
(SEQ ID NO: 33)
GCCGGCCATGGCCCAGSTBCAGCTGCAGCAATCTGG

MVH-8
(SEQ ID NO: 34)
GCCGGCCATGGCCCAGGTYCAGCTGCAGCAGTCTGGRC

MVH-9
(SEQ ID NO: 35)
GCCGGCCATGGCCCAGGTYCAGCTYCAGCAGTCTGG

MVH-10
(SEQ ID NO: 36)
GCCGGCCATGGCCGAGGTCCARCTGCAACAATCTGGACC

MVH-11
(SEQ ID NO: 37)
GCCGGCCATGGCCCAGGTCCACGTGAAGCAGTCTGGG

MVH-12
(SEQ ID NO: 38)
GCCGGCCATGGCCGAGGTGAASSTGGTGGAATCTG

MVH-13
(SEQ ID NO: 39)
GCCGGCCATGGCCGAVGTGAAGYTGGTGGAGTCTG

MVH-14
(SEQ ID NO: 40)
GCCGGCCATGGCCGAGGTGCAGSKGGTGGAGTCTGGGG

MVH-15
(SEQ ID NO: 41)
GCCGGCCATGGCCGAKGTGCAMCTGGTGGAGTCTGGG

MVH-16
(SEQ ID NO: 42)
GCCGGCCATGGCCGAGGTGAAGCTGATGGARTCTGG

MVH-17
(SEQ ID NO: 43)
GCCGGCCATGGCCGAGGTGCARCTTGTTGAGTCTGGTG

MVH-18
(SEQ ID NO: 44)
GCCGGCCATGGCCGARGTRAAGCTTCTAGAGTCTGGA

MVH-19
(SEQ ID NO: 45)
GCCGGCCATGGCCGAAGTGAARSTTGAGGAGTCTGG

MVH-20
(SEQ ID NO: 46)
GCCGGCCATGGCCGAAGTGATGCTGGTGGAGTCTGGG

MVH-21
(SEQ ID NO: 47)
GCCGGCCATGGCCCAGGTTACTCTRAAAGWGTSTGGCC

MVH-22
(SEQ ID NO: 48)
GCCGGCCATGGCCCAGGTCCAACTVCAGCARCCTGG

MVH-23
(SEQ ID NO: 49)
GCCGGCCATGGCCCAGGTYCARCTGCAGCAGTCTG

MVH-24
(SEQ ID NO: 50)
GCCGGCCATGGCCGATGTGAACTTGGAAGTGTCTGG

MVH-25
(SEQ ID NO: 51)
GCCGGCCATGGCCGAGGTGAAGGTCATCGAGTCTGG

H-Chain Forward Primers:

MJH-REV1&2
(SEQ ID NO: 64)
GGGGGTGTCGTTTTGGCTGAGGAGACGGTGACCGTGG

MJH-REV2INT
(SEQ ID NO: 65)
GGGGGTGTCGTTTTGGCTGAGGAGACGGTGACAGTGG

MJH-REV3
(SEQ ID NO: 66)
GGGGGTGTCGTTTTGGCTGAGGAGACGGTGACCAGAG

MJH-REV4
(SEQ ID NO: 67)
GGGGGTGTCGTTTTGGCTGAGGAGACGGTGACCGAGG

Variable position key: R (A/G); M (A/C); Y (T/C); W (A/T); S (G/C); K (G/T); H (A/T/C); B (G/C/T); V (G/A/C); D (G/A/T); N (G/A/T/C)

In this experiment, mouse-specific oligos are used. For more reproducible results, rat-specific oligos can be used as well.

Results

The light chain sequence of LGR5-specific antibody NR 2F10 (see Table 4) and the heavy chain sequences of LGR6-specific antibodies 6d8 and 2f4 (see Table 5) are depicted in FIG. 27. The CDR regions are indicated in bold and in italics. The CDR sequences were determined according to Kabat (Kabat et al., "Sequences of Proteins of Immunological Interest," U.S. Dept. of Health and Human Services, National Institute of Health, 1987). Antibodies or functional equivalents thereof comprising at least one of these CDR sequences constitute a high affinity binding compound with a high specificity for their target proteins LGR5 and/or LGR6.

REFERENCES 1

1) Reya, T., Morrison, S. J., Clarke, M. F. & Weissman, I. L. Stem cells, cancer, and cancer stem cells. Nature 414, 105-111 (2001)
2) Stingl J, Eirew P, Ricketson I, Shackleton M, Vaillant F, Choi D, Li H I, Eaves C J Purification and unique properties of mammary epithelial stem cells. Nature. 439:993-7
3) Bach S P, Renehan A G, Potten C S. Stem cells: the intestinal stem cell as a paradigm. Carcinogenesis 21(3): 469-76 (2000)
4) Booth C, Potten C S. Gut instincts: thoughts on intestinal epithelial stem cells. J. Clin. Invest 105(11):1493-9 (2000)
5) Bjerknes M, Cheng H. Clonal analysis of mouse intestinal epithelial progenitors. Gastroenterology 116(1):7-14 (1999)
6) Nishimura S, Wakabayashi N, Toyoda K, Kashima K, Mitsufuji S. Expression of Musashi-1 in human normal colon crypt cells: a possible stem cell marker of human colon epithelium. Dig. Dis. Sci. 48(8):1523-9 (2003)
7) Potten C S, Booth C, Tudor G L, Booth D, Brady G, Hurley P, Ashton G, Clarke R, Sakakibara S, Okano H. Identification of a putative intestinal stem cell and early lineage marker; musashi-1. Differentiation 71(1):28-41 (2003)
8) He X C, Zhang J, Tong W G, Tawfik O, Ross J, Scoville D H, Tian Q, Zeng X, He X, Wiedemann L M, Mishina Y, Li L B M P signaling inhibits intestinal stem cell self-renewal through suppression of Wnt-beta-catenin signaling. Nat Genet. 36:1117-21 (2004)
9) Bjerknes M, Cheng H. Re-examination of P-PTEN staining patterns in the intestinal crypt. Nat Genet. 37: 1016-7 (2005)
10) Marshman E, Booth C, Potten C S. The intestinal epithelial stem cell. Bioessays 24(1):91-8 (2002)
11) Yatabe Y, Tavare S, Shibata D. Investigating stem cells in human colon by using methylation patterns. Proc. Natl. Acad. Sci. USA 98(19):10839-44 (2001)
12) Radtke, F and Clevers, H., Self-renewal and cancer of the gut: Two sides of a coin. Review Science. 307: 1904-1909 (2005)
13) Reya, T., Morrison, S. J., Clarke, M. F. & Weissman, I. L. Stem cells, cancer, and cancer stem cells. Nature 414, 105-111 (2001)
14) Clarke M F, Dick J E, Dirks P B, Eaves C J, Jamieson C H, Jones D L, Visvader J, Weissman I L, Wahl G M. Cancer Stem Cells—Perspectives on Current Status and Future Directions: AACR Workshop on Cancer Stem Cells. Cancer Res. 66:9339-44 (2006).
15) Lapidot T, Sirard C, Vormoor J, Murdoch B, Hoang T, Caceres-Cortes J, Minden M, Paterson B, Caligiuri M A, Dick J E. A cell initiating human acute myeloid leukaemia after transplantation into SCID mice. Nature. 367:645-8 (1994)
16) Bonnet D, Dick J E. Human acute myeloid leukemia is organized as a hierarchy that originates from a primitive hematopoietic cell. Nat Med. 3:730-7 (1997).
17) Al-Hajj M, Wicha M S, Benito-Hernandez A, Morrison S J, Clarke M F. Prospective identification of tumorigenic breast cancer cells. Proc Natl Acad Sci USA. 100:3983-8 (2003).
18) Nakano I, Kornblum H I Brain tumor stem cells. Pediatr Res. 59:54R-8R. Review (2006)
19) Collins A T, Maitland N J. Prostate cancer stem cells. Eur J Cancer. 42:1213-8. Review (2006)
20) O'Brien C A, Pollett A, Gallinger S, Dick J E A human colon cancer cell capable of initiating tumour growth in immunodeficient mice. Nature 445:106-10 (2007).
21) Ricci-Vitiani L, Lombardi D G, Pilozzi E, Biffoni M, Todaro M, Peschle C, De Maria R. Identification and expansion of human colon-cancer-initiating cells. Nature. 445:111-5 (2007)
22) van de Wetering, M., Sancho, E., Verweij, C., de Lau, W., Oving, I., Hurlstone, A., van der Horn, K., Batlle, E., Coudreuse, D., Haramis, A-P., Tjon-Pon-Fong, M., Moerer, P., van den Born, M., Soete, G., Pals, S., Eilers, M., Medema, R., Clevers, H. The beta-catenin/TCF4 complex imposes a crypt progenitor phenotype on colorectal cancer cells. Cell 111: 241-250 (2002)
23) Wielenga, V. J., Smits, R., Korinek, V., Smit, L., Kielman, M., Fodde, R., Clevers, H., Pals, S. T. Expression of CD44 in Apc and Tcf mutant mice implies regulation by the WNT pathway. Am J Pathol 54: 515-523 (1999)
24) Malaterre, J. et al. c-Myb is required for progenitor cell homeostasis in colonic crypts. Proc. Natl. Acad. Sci USA 104, 3829-3834 (2007)
25) Brigelius-Flohe, R. Glutathione peroxidases and redox-regulated transcription factors (2006) *Biological Chemistry,* 387 (10-11), pp. 1329-1335.
26) Neid, M., Wittekind, C. Epidemiology, pathology, and staging of mesenchymal and endocrine tumours of the gastrointestinal tract (2007) *Chirurgische Gastroenterologie nterdisziplinar,* 23 (2), pp. 108-112.
27) Battle, E., Henderson, J. T., Beghtel, H., van den Born, M., Sancho, E., Huls, G., Meeldijk, J., Robertson, J., van de Wetering, M., Pawson, T., Clevers, H. Beta-catenin and TCF mediate cell positioning in the intestinal epithelium by controlling the expression of EphB/ephrinB. Cell 111: 251-263 (2002)
28) Haramis, A. P., Begthel, H., van den Born, M., van Es, J., Jonkheer, S., Offerhaus, G. J., Clevers, H. De novo crypt formation and Juvenile Polyposis upon BMP inhibition Science. 303: 1684-1686 (2004)
29) Hewitt, K. J., Agarwal, R., Morin, P. J. The claudin gene family: Expression in normal and neoplastic tissues (2006) *BMC Cancer,* 6, art. no. 186
30) Shea Yu Hsu, Kudo, M., Chen, T., Nakabayashi, K., Bhalla, A., Van der Spek, P. J., Van Duin, M., ( . . . ), Hsueh, A. J. W. The three subfamilies of leucine-rich repeat-containing G protein-coupled receptors (LGR): Identification of LGR6 and LGR7 and the signaling mechanism for LGR7 (2000) *Molecular Endocrinology,* 14 (8), pp. 1257-1271.
31) Van Schoore, G., Mendive, F., Pochet, R., Vassart, G. Expression pattern of the orphan receptor LGR4/GPR48 gene in the mouse (2005) *Histochemistry and Cell Biology,* 124 (1), pp. 35-50
32) Mazerbourg, S., Bouley, D. M., Sudo, S., Klein, C. A., Zhang, J. V., Kawamura, K., Goodrich, L. V., ( . . . ), Hsueh, A. J. W. Leucine-rich repeat-containing, G protein-coupled receptor 4 null mice exhibit intrauterine growth retardation associated with embryonic and perinatal lethality. (2004) *Molecular Endocrinology,* 18 (9), pp. 2241-2254
33) Mendive, F., Laurent, P., Van Schoore, G., Skarnes, W., Pochet, R., Vassart, G. Defective postnatal development of the male reproductive tract in LGR4 knockout mice. 2006) *Developmental Biology,* 290 (2), pp. 421-434.
34) Kato, S., Matsubara, M., Matsuo, T., Mohri, Y., Kazama, I., Hatano, R., Umezawa, A., ( . . . ), Nishimori, K. Leucine-rich repeat-containing G protein-coupled receptor-4 (LGR4, Gpr48) is essential for renal development in mice (2006) *Nephron—Experimental Nephrology*, 104 (2), pp. e63-e75

35) Morita H, Mazerbourg S, Bouley D M, Luo C W, Kawamura K, Kuwabara Y, Baribault H, Tian H, Hsueh A J. Neonatal lethality of LGR5 null mice is associated with ankyloglossia and gastrointestinal distension. Mol Cell Biol. 24:9736-43 (2004)

36) Yamamoto Y, Sakamoto M, Fujii G, Tsuiji H, Kenetaka K, Asaka M, Hirohashi S. Overexpression of orphan G-protein-coupled receptor, Gpr49, in human hepatocellular carcinomas with beta-catenin mutations. Hepatology. 37:528-33 (2003)

37) McClanahan T, Koseoglu S, Smith K, Grein J, Gustafson E, Black S, Kirschmeier P, Samatar A A. Identification of overexpression of orphan G protein-coupled receptor GPR49 in human colon and ovarian primary tumors. Cancer Biol Ther. 5:419-26. (2006).

REFERENCES 2

1. Gregorieff, A. & Clevers, H. Wnt signaling in the intestinal epithelium: from endoderm to cancer. Genes Dev 19, 877-90 (2005).
2. Bjerknes, M. & Cheng, H. Clonal analysis of mouse intestinal epithelial progenitors. Gastroenterology 116, 7-14 (1999).
3. Winton, D. J. & Ponder, B. A. Stem-cell organization in mouse small intestine. Proc Biol Sci 241, 13-8 (1990).
4. Potten, C. S., Booth, C. & Pritchard, D. M. The intestinal epithelial stem cell: the mucosal governor. Int J Exp Pathol 78, 219-43 (1997).
5. Korinek, V. et al. Depletion of epithelial stem-cell compartments in the small intestine of mice lacking Tcf-4. Nat Genet 19, 379-83 (1998).
6. van de Wetering, M. et al. The beta-catenin/TCF-4 complex imposes a crypt progenitor phenotype on colorectal cancer cells. Cell 111, 241-50 (2002).
7. Van der Flier, L. G. et al. The Intestinal Wnt/TCF Signature. Gastroenterology 132, 628-32 (2007).
8. Hsu, S. Y., Liang, S. G. & Hsueh, A. J. Characterization of two LGR genes homologous to gonadotropin and thyrotropin receptors with extracellular leucine-rich repeats and a G protein-coupled, seven-transmembrane region. Mol Endocrinol 12, 1830-45 (1998).
9. McClanahan, T. et al. Identification of overexpression of orphan G protein-coupled receptor GPR49 in human colon and ovarian primary tumors. Cancer Biol Ther 5, 419-26 (2006).
10. Yamamoto, Y. et al. Overexpression of orphan G-protein-coupled receptor, Gpr49, in human hepatocellular carcinomas with beta-catenin mutations. Hepatology 37, 528-33 (2003).
11. Morita, H. et al. Neonatal lethality of LGR5 null mice is associated with ankyloglossia and gastrointestinal distension. Mol Cell Biol 24, 9736-43 (2004).
12. Reya, T. & Clevers, H. Wnt signalling in stem cells and cancer. Nature 434, 843-50 (2005).
13. Cheng, H. & Leblond, C. P. Origin, differentiation and renewal of the four main epithelial cell types in the mouse small intestine. V. Unitarian Theory of the origin of the four epithelial cell types. Am J Anat 141, 537-61 (1974).
14. Bjerknes, M. & Cheng, H. The stem-cell zone of the small intestinal epithelium. III. Evidence from columnar, enteroendocrine, and mucous cells in the adult mouse. Am J Anat 160, 77-91 (1981).
15. Stappenbeck, T. S., Mills, J. C. & Gordon, J. I. Molecular features of adult mouse small intestinal epithelial progenitors. Proc Natl Acad Sci USA 100, 1004-9 (2003).
16. Soriano, P. Generalized lacZ expression with the ROSA26 Cre reporter strain. Nat Genet 21, 70-1 (1999).
17. Potten, C. S., Owen, G. & Booth, D. Intestinal stem cells protect their genome by selective segregation of template DNA strands. J Cell Sci 115, 2381-8 (2002).
18. Ohlstein, B., Kai, T., Decotto, E. & Spradling, A. The stem cell niche: theme and variations. Curr Opin Cell Biol 16, 693-9 (2004).
19. Clayton, E. et al. A single type of progenitor cell maintains normal epidermis. Nature 446, 185-9 (2007).
20. Nishimura, S., Wakabayashi, N., Toyoda, K., Kashima, K. & Mitsufuji, S. Expression of Musashi-1 in human normal colon crypt cells: a possible stem cell marker of human colon epithelium. Dig Dis Sci 48, 1523-9 (2003).
21. Potten, C. S. et al. Identification of a putative intestinal stem cell and early lineage marker; musashi-1. Differentiation 71, 28-41 (2003).
22. O'Brien, C. A., Pollett, A., Gallinger, S. & Dick, J. E. A human colon cancer cell capable of initiating tumour growth in immunodeficient mice. Nature 445, 106-10 (2007).
23. He, X. C. et al. BMP signaling inhibits intestinal stem cell self-renewal through suppression of Wnt-beta-catenin signaling. Nat Genet 36, 1117-21 (2004).
24. Claudinot, S., Nicolas, M., Oshima, H., Rochat, A. & Barrandon, Y. Long-term renewal of hair follicles from clonogenic multipotent stem cells. Proc Natl Acad Sci USA 102, 14677-82 (2005).
25. Cotsarelis, G., Sun, T. T. & Lavker, R. M. Label-retaining cells reside in the bulge area of pilosebaceous unit: implications for follicular stem cells, hair cycle, and skin carcinogenesis. Cell 61, 1329-37 (1990).
26. Tumbar, T. et al. Defining the epithelial stem cell niche in skin. Science 303, 359-63 (2004).
27. Morris, R. J. et al. Capturing and profiling adult hair follicle stem cells. Nat Biotechnol 22, 411-7 (2004).
28. Bjerknes, M. & Cheng, H. Multipotential stem cells in adult mouse gastric epithelium. Am J Physiol Gastrointest Liver Physiol 283, G767-77 (2002).
29. Sleeman, K. E. et al. Dissociation of estrogen receptor expression and in vivo stem cell activity in the mammary gland. J Cell Biol 176, 19-26 (2007).
30. Muncan, V. et al. Rapid loss of intestinal crypts upon conditional deletion of the Wnt/Tcf-4 target gene c-Myc. Mol Cell Biol 26, 8418-26 (2006).

REFERENCES 5

1. Barker, N. v. d. W., M. Clevers, H. The intestinal stem cell. Gen Dev in press, (2008).
2. Potten, C. S. Kinetics and possible regulation of crypt cell populations under normal and stress conditions. Bull Cancer 62, 419-30 (1975).
3. Barker, N. et al. Identification of stem cells in small intestine and colon by marker gene Lgr5. Nature 449, 1003-7 (2007).
4. Cheng, H. & Leblond, C. P. Origin, differentiation and renewal of the four main epithelial cell types in the mouse small intestine. V. Unitarian Theory of the origin of the four epithelial cell types. Am J Anat 141, 537-61 (1974).
5. Cheng, H. & Leblond, C. P. Origin, differentiation and renewal of the four main epithelial cell types in the mouse small intestine. I. Columnar cell. Am J Anat 141, 461-79 (1974).

6. Marshman, E., Booth, C. & Potten, C. S. The intestinal epithelial stem cell. Bioessays 24, 91-8 (2002).
7. Bjerknes, M. & Cheng, H. The stem-cell zone of the small intestinal epithelium. II. Evidence from paneth cells in the newborn mouse. Am J Anat 160, 65-75 (1981).
8. Bjerknes, M. & Cheng, H. The stem-cell zone of the small intestinal epithelium. I. Evidence from Paneth cells in the adult mouse. Am J Anat 160, 51-63 (1981).
9. Ireland, H., Houghton, C., Howard, L. & Winton, D. J. Cellular inheritance of a Cre-activated reporter gene to determine Paneth cell longevity in the murine small intestine. Dev Dyn 233, 1332-6 (2005).
10. Jones, S. et al. Comparative lesion sequencing provides insights into tumor evolution. Proc Natl Acad Sci USA 105, 4283-8 (2008).
11. Kinzler, K. W. & Vogelstein, B. Lessons from hereditary colorectal cancer. Cell 87, 159-70 (1996).
12. Korinek, V. et al. Constitutive transcriptional activation by a beta-catenin-Tcf complex in APC−/−colon carcinoma. Science 275, 1784-7 (1997).
13. Morin, P. J. et al. Activation of beta-catenin-Tcf signaling in colon cancer by mutations in beta-catenin or APC. Science 275, 1787-90 (1997).
14. van de Wetering, M. et al. The beta-catenin/TCF-4 complex imposes a crypt progenitor phenotype on colorectal cancer cells. Cell 111, 241-50 (2002).
15. Van der Flier, L. G. et al. The Intestinal Wnt/TCF Signature. Gastroenterology 132, 628-32 (2007).
16. Sansom, O. J. et al. Loss of Apc in vivo immediately perturbs Wnt signaling, differentiation, and migration. Genes Dev 18, 1385-90 (2004).
17. Shibata, H. et al. Rapid colorectal adenoma formation initiated by conditional targeting of the Apc gene. Science 278, 120-3 (1997).
18. Sansom, O. J. et al. Myc deletion rescues Apc deficiency in the small intestine. Nature 446, 676-9 (2007).
19. Sansom, O. J. et al. Cyclin D1 is not an immediate target of beta-catenin following Apc loss in the intestine. J Biol Chem 280, 28463-7 (2005).
20. Soriano, P. Generalized lacZ expression with the ROSA26 Cre reporter strain. Nat Genet 21, 70-1 (1999).

The invention claimed is:

1. A method for testing the effect of a compound comprising
   (a) contacting a cell population comprising cancer stem cells in vitro with said compound, wherein the cancer stem cells
      comprise Lgr6 and/or Lgr5 embedded in their cell membrane;
      and
   (b) testing the ability of said contacted cancer stem cells to generate a tumor relative to cancer stem cells that are not contacted with said compound,
   wherein a difference in the tumor-generating ability of the contacted and non-contacted cancer stem cells indicates an effect of the compound.

2. The method of claim 1, further comprising testing the effect of said compound on normal tissue stem cells or organ stem cells, comprising contacting normal tissue stem cells or organ stem cells with said compound and determining a change in the number of normal tissue stem cells or organ stem cells, following contact with said compound.

3. The method of claim 1, wherein the cell population comprises at least 50% Lgr5 and/or Lgr6 positive stem cells, at least 60% Lgr5 and/or Lgr6 positive stem cells, at least 70% Lgr5 and/or Lgr6 positive stem cells, at least 80% Lgr5 and/or Lgr6 positive stem cells, at least 90% Lgr5 and/or Lgr6 positive stem cells, or at least 95% Lgr5 and/or Lgr6 positive stem cells.

4. The method of claim 1, wherein said compound is an anti-Lgr5 antibody.

5. The method of claim 1, further comprising measuring the number of cancer stem cells in the cell population before and after contact with said compound.

6. The method of claim 1, further comprising, prior to step (a), obtaining the cell population comprising cancer stem cells by contacting a cell suspension prepared from a solid or liquid tumor sample with an Lgr6 specific antibody or antibody fragment, and isolating cells that bind to the Lgr6 specific antibody or antibody fragment.

* * * * *

UNITED STATES PATENT AND TRADEMARK OFFICE
CERTIFICATE OF CORRECTION

PATENT NO. : 10,940,180 B2
APPLICATION NO. : 15/813863
DATED : March 9, 2021
INVENTOR(S) : Johannes C. Clevers et al.

Page 1 of 1

It is certified that error appears in the above-identified patent and that said Letters Patent is hereby corrected as shown below:

On the Title Page

Item (30), Replace the Foreign Application Priority Data as follows:
(30) Foreign Application Priority Data
Aug. 10, 2007 (EP) ....................................... 07114192.3

In the Specification

Replace the paragraph beginning at Column 1, Line 5, with the following paragraph:
RELATED APPLICATIONS
This application is a divisional of U.S. patent application Ser. No. 14/494,511,
filed Sep. 23, 2014, now U.S. Pat. No. 9,833,496, which is a continuation of U.S. patent
application Ser. No. 12/705,336, filed May 10, 2010, now U.S. Pat. No. 8,906,631,
which is a continuation of International Application No. PCT/NL2008/050543, filed
Aug. 8, 2008, which was published under PCT Article 21 (2) in English and which
claims priority to European Application No. 07114192.3, filed Aug. 10, 2007, the entire
contents of all of which are incorporated by reference herein.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 67

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacattgttc tcacccagtc tcc                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacattgtgc tsacccagtc tcc                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gacattgtga tgactcagtc tcc                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```
gacattgtgc tmactcagtc tcc                                            23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gacattgtgy tracacagtc tcc                                            23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacattgtra tgacacagtc tcc                                            23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacattmaga tracccagtc tcc                                            23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gacattgcag atgamccagt ctcc                                           24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gacattcaga tgacdcagtc tcc                                            23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacattcaga tgacacagac tac                                            23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gacattcaga tgattcagtc tcc                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gacattgttc tcawccagtc tcc                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gacattgttc tctcccagtc tcc                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gacattgwgc tsacccaatc tcc                                              23

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacattstga tgacccartc tc                                               22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gacattktga tgacccarac tcc                                              23

```
<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacattgtga tgactcaggc tac                                              23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gacattgtga tgacbcaggc tgc                                              23

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gacattgtga taacycagga tg                                               22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gacattgtga tgacccagtt tgc                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gacattgtga tgacacaacc tgc                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gacattgtga tgacccagat tcc                                              23
```

```
<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gacattttgc tgactcagtc tcc                                            23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gacattgtaa tgacccaatc tcc                                            23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gacattgtga tgacccacac tcc                                            23

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acactcattc ctgttgaagc tcttgac                                        27

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gccggccatg gccgaggtrm agcttcagga gtcaggac                            38

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gccggccatg gccgaggtsc agctkcagca gtcaggac                            38

<210> SEQ ID NO 29
```

-continued

```
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gccggccatg gcccaggtgc agctgaagsa stcagg                                     36

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gccggccatg gccgaggtgc agcttcagga gtcsggac                                   38

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gccggccatg gccgargtcc agctgcaaca gtcyggac                                   38

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gccggccatg gcccaggtcc agctkcagca atctgg                                     36

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gccggccatg gcccagstbc agctgcagca atctgg                                     36

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gccggccatg gcccaggtyc agctgcagca gtctggrc                                   38

<210> SEQ ID NO 35
<211> LENGTH: 36
```

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gccggccatg gcccaggtyc agctycagca gtctgg    36

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gccggccatg gccgaggtcc arctgcaaca atctggacc    39

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gccggccatg gcccaggtcc acgtgaagca gtctggg    37

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gccggccatg gccgaggtga asstggtgga atctg    35

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gccggccatg gccgavgtga agytggtgga gtctg    35

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gccggccatg gccgaggtgc agskggtgga gtctgggg    38

<210> SEQ ID NO 41
<211> LENGTH: 37
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 41
gccggccatg gccgakgtgc amctggtgga gtctggg                          37

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gccggccatg gccgaggtga agctgatgga rtctgg                           36

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gccggccatg gccgaggtgc arcttgttga gtctggtg                         38

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gccggccatg gccgargtra agcttctaga gtctgga                          37

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccggccatg gccgaagtga arsttgagga gtctgg                           36

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gccggccatg gccgaagtga tgctggtgga gtctggg                          37

<210> SEQ ID NO 47
<211> LENGTH: 38
<212> TYPE: DNA
<213> ORGANISM: Artificial Sequence -continued
<220> FEATURE:
<223> OTHER INFORMATION: Description of Artificial Sequence: Synthetic
      primer

<400> SEQUENCE: 47
gccggccatg gcccaggtta ctctraaagw gtstggcc                                    38

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gccggccatg gcccaggtcc aactvcagca rcctgg                                      36

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gccggccatg gcccaggtyc arctgcagca gtctg                                       35

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gccggccatg gccgatgtga acttggaagt gtctgg                                      36

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gccggccatg gccgaggtga aggtcatcga gtctgg                                      36

<210> SEQ ID NO 52
<211> LENGTH: 951
<212> TYPE: PRT
<213> ORGANISM: Homo sapiens

<400> SEQUENCE: 52

Met Pro Gly Pro Leu Gly Leu Leu Cys Phe Leu Ala Leu Gly Leu Leu
1               5                   10                  15

Gly Ser Ala Gly Pro Ser Gly Ala Ala Pro Leu Cys Ala Ala Pro
            20                  25                  30

Cys Ser Cys Asp Gly Asp Arg Arg Val Asp Cys Ser Gly Lys Gly Leu
        35                  40                  45

Thr Ala Val Pro Glu Gly Leu Ser Ala Phe Thr Gln Ala Leu Asp Ile
    50                  55                  60

-continued

```
Ser Met Asn Asn Ile Thr Gln Leu Pro Glu Asp Ala Phe Lys Asn Phe
 65                  70                  75                  80

Pro Phe Leu Glu Glu Leu Gln Leu Ala Gly Asn Asp Leu Ser Phe Ile
                 85                  90                  95

His Pro Lys Ala Leu Ser Gly Leu Lys Glu Leu Lys Val Leu Thr Leu
            100                 105                 110

Gln Asn Asn Gln Leu Lys Thr Val Pro Ser Glu Ala Ile Arg Gly Leu
        115                 120                 125

Ser Ala Leu Gln Ser Leu Arg Leu Asp Ala Asn His Ile Thr Ser Val
130                 135                 140

Pro Glu Asp Ser Phe Glu Gly Leu Val Gln Leu Arg His Leu Trp Leu
145                 150                 155                 160

Asp Asp Asn Ser Leu Thr Glu Val Pro Val His Pro Leu Ser Asn Leu
                165                 170                 175

Pro Thr Leu Gln Ala Leu Thr Leu Ala Leu Asn Lys Ile Ser Ser Ile
            180                 185                 190

Pro Asp Phe Ala Phe Thr Asn Leu Ser Ser Leu Val Val Leu His Leu
        195                 200                 205

His Asn Asn Lys Ile Arg Ser Leu Ser Gln His Cys Phe Asp Gly Leu
210                 215                 220

Asp Asn Leu Glu Thr Leu Asp Leu Asn Tyr Asn Asn Leu Gly Glu Phe
225                 230                 235                 240

Pro Gln Ala Ile Lys Ala Leu Pro Ser Leu Lys Glu Leu Gly Phe His
                245                 250                 255

Ser Asn Ser Ile Ser Val Ile Pro Asp Gly Ala Phe Asp Gly Asn Pro
            260                 265                 270

Leu Leu Arg Thr Ile His Leu Tyr Asp Asn Pro Leu Ser Phe Val Gly
        275                 280                 285

Asn Ser Ala Phe His Asn Leu Ser Asp Leu His Ser Leu Val Ile Arg
290                 295                 300

Gly Ala Ser Met Val Gln Gln Phe Pro Asn Leu Thr Gly Thr Val His
305                 310                 315                 320

Leu Glu Ser Leu Thr Leu Thr Gly Thr Lys Ile Ser Ser Ile Pro Asn
                325                 330                 335

Asn Leu Cys Gln Glu Gln Lys Met Leu Arg Thr Leu Asp Leu Ser Tyr
            340                 345                 350

Asn Asn Ile Arg Asp Leu Pro Ser Phe Asn Gly Cys His Ala Leu Glu
        355                 360                 365

Glu Ile Ser Leu Gln Arg Asn Gln Ile Tyr Gln Ile Lys Glu Gly Thr
370                 375                 380

Phe Gln Gly Leu Ile Ser Leu Arg Ile Leu Asp Leu Ser Arg Asn Leu
385                 390                 395                 400

Ile His Glu Ile His Ser Arg Ala Phe Ala Thr Leu Gly Pro Ile Thr
                405                 410                 415

Asn Leu Asp Val Ser Phe Asn Glu Leu Thr Ser Phe Pro Thr Glu Gly
            420                 425                 430

Leu Asn Gly Leu Asn Gln Leu Lys Leu Val Gly Asn Phe Lys Leu Lys
        435                 440                 445

Glu Ala Leu Ala Ala Lys Asp Phe Val Asn Leu Arg Ser Leu Ser Val
450                 455                 460

Pro Tyr Ala Tyr Gln Cys Cys Ala Phe Trp Gly Cys Asp Ser Tyr Ala
465                 470                 475                 480
```

-continued

Asn Leu Asn Thr Glu Asp Asn Ser Leu Gln Asp His Ser Val Ala Gln
            485                 490                 495

Glu Lys Gly Thr Ala Asp Ala Ala Asn Val Thr Ser Thr Leu Glu Asn
            500                 505                 510

Glu Glu His Ser Gln Ile Ile Ile His Cys Thr Pro Ser Thr Gly Ala
            515                 520                 525

Phe Lys Pro Cys Glu Tyr Leu Leu Gly Ser Trp Met Ile Arg Leu Thr
            530                 535                 540

Val Trp Phe Ile Phe Leu Val Ala Leu Phe Phe Asn Leu Leu Val Ile
545                 550                 555                 560

Leu Thr Thr Phe Ala Ser Cys Thr Ser Leu Pro Ser Ser Lys Leu Phe
            565                 570                 575

Ile Gly Leu Ile Ser Val Ser Asn Leu Phe Met Gly Ile Tyr Thr Gly
            580                 585                 590

Ile Leu Thr Phe Leu Asp Ala Val Ser Trp Gly Arg Phe Ala Glu Phe
            595                 600                 605

Gly Ile Trp Trp Glu Thr Gly Ser Gly Cys Lys Val Ala Gly Phe Leu
            610                 615                 620

Ala Val Phe Ser Ser Glu Ser Ala Ile Phe Leu Leu Met Leu Ala Thr
625                 630                 635                 640

Val Glu Arg Ser Leu Ser Ala Lys Asp Ile Met Lys Asn Gly Lys Ser
            645                 650                 655

Asn His Leu Lys Gln Phe Arg Val Ala Ala Leu Leu Ala Phe Leu Gly
            660                 665                 670

Ala Thr Val Ala Gly Cys Phe Pro Leu Phe His Arg Gly Glu Tyr Ser
            675                 680                 685

Ala Ser Pro Leu Cys Leu Pro Phe Pro Thr Gly Glu Thr Pro Ser Leu
            690                 695                 700

Gly Phe Thr Val Thr Leu Val Leu Leu Asn Ser Leu Ala Phe Leu Leu
705                 710                 715                 720

Met Ala Val Ile Tyr Thr Lys Leu Tyr Cys Asn Leu Glu Lys Glu Asp
            725                 730                 735

Leu Ser Glu Asn Ser Gln Ser Ser Met Ile Lys His Val Ala Trp Leu
            740                 745                 750

Ile Phe Thr Asn Cys Ile Phe Phe Cys Pro Val Ala Phe Phe Ser Phe
            755                 760                 765

Ala Pro Leu Ile Thr Ala Ile Ser Ile Ser Pro Glu Ile Met Lys Ser
            770                 775                 780

Val Thr Leu Ile Phe Phe Pro Leu Pro Ala Cys Leu Asn Pro Val Leu
785                 790                 795                 800

Tyr Val Phe Phe Asn Pro Lys Phe Lys Glu Asp Trp Lys Leu Leu Lys
            805                 810                 815

Arg Arg Val Thr Lys Lys Ser Gly Ser Val Ser Val Ser Ile Ser Ser
            820                 825                 830

Gln Gly Gly Cys Leu Glu Gln Asp Phe Tyr Tyr Asp Cys Gly Met Tyr
            835                 840                 845

Ser His Leu Gln Gly Asn Leu Thr Val Cys Asp Cys Cys Glu Ser Phe
            850                 855                 860

Leu Leu Thr Lys Pro Val Ser Cys Lys His Leu Ile Lys Ser His Ser
865                 870                 875                 880

Cys Pro Ala Leu Ala Val Ala Ser Cys Gln Arg Pro Glu Gly Tyr Trp
            885                 890                 895

Ser Asp Cys Gly Thr Gln Ser Ala His Ser Asp Tyr Ala Asp Glu Glu

```
                    900                 905                 910
Asp Ser Phe Val Ser Asp Ser Ser Asp Gln Val Gln Ala Cys Gly Arg
            915                 920                 925

Ala Cys Phe Tyr Gln Ser Arg Gly Phe Pro Leu Val Arg Tyr Ala Tyr
            930                 935                 940

Asn Leu Pro Arg Val Lys Asp
945                 950

<210> SEQ ID NO 53
<211> LENGTH: 953
<212> TYPE: PRT
<213> ORGANISM: Rattus norvegicus

<400> SEQUENCE: 53

Met Pro Gly Pro Leu Arg Leu Leu Cys Phe Phe Ala Leu Gly Leu Leu
1               5                   10                  15

Gly Ser Ala Gly Pro Ser Gly Ala Ala Pro Pro Leu Cys Ala Ala Pro
            20                  25                  30

Cys Ser Cys Asp Gly Asp Arg Arg Val Asp Cys Ser Gly Lys Gly Leu
        35                  40                  45

Thr Ala Val Pro Glu Gly Leu Ser Ala Phe Thr Gln Ala Leu Asp Ile
    50                  55                  60

Ser Met Asn Asn Ile Thr Gln Leu Pro Glu Asp Ala Phe Lys Ser Phe
65                  70                  75                  80

Pro Phe Leu Glu Glu Leu Gln Leu Ala Gly Asn Asp Leu Ser Phe Ile
                85                  90                  95

His Pro Lys Ala Leu Ser Gly Leu Lys Glu Leu Lys Val Leu Thr Leu
            100                 105                 110

Gln Asn Asn Gln Leu Arg Thr Val Pro Ser Glu Ala Ile His Gly Leu
        115                 120                 125

Ser Ala Leu Gln Ser Leu Arg Leu Asp Ala Asn His Ile Thr Ser Val
    130                 135                 140

Pro Glu Asp Ser Phe Glu Gly Leu Val Gln Leu Arg His Leu Trp Leu
145                 150                 155                 160

Asp Asp Asn Ser Leu Thr Glu Val Pro Val Arg Pro Leu Ser Asn Leu
                165                 170                 175

Pro Thr Leu Gln Ala Leu Thr Leu Ala Leu Asn Asn Ile Ser Ser Ile
            180                 185                 190

Pro Asp Phe Ala Phe Thr Asn Leu Ser Ser Leu Val Val Leu His Leu
        195                 200                 205

His Asn Asn Lys Ile Lys Ser Leu Ser Gln His Cys Phe Asp Gly Leu
    210                 215                 220

Asp Asn Leu Glu Thr Leu Asp Leu Asn Tyr Asn Asn Leu Asp Glu Phe
225                 230                 235                 240

Pro Gln Ala Ile Lys Ala Leu Pro Ser Leu Lys Glu Leu Gly Phe His
                245                 250                 255

Ser Asn Ser Ile Ser Val Ile Pro Asp Gly Ala Phe Gly Gly Asn Pro
            260                 265                 270

Leu Leu Arg Thr Ile His Leu Tyr Asp Asn Pro Leu Ser Phe Val Gly
        275                 280                 285

Asn Ser Ala Phe His Asn Leu Ser Asp Leu His Ser Leu Val Ile Arg
    290                 295                 300

Gly Ala Ser Leu Val Gln Trp Phe Pro Asn Leu Thr Gly Thr Val His
305                 310                 315                 320
```

-continued

Leu Glu Ser Leu Thr Leu Thr Gly Thr Lys Ile Ser Ile Pro Asp
            325                 330                 335

Asp Leu Cys Gln Asn Gln Lys Met Leu Arg Thr Leu Asp Leu Ser Tyr
        340                 345                 350

Asn Asn Ile Arg Asp Leu Pro Ser Phe Asn Gly Cys Arg Ala Leu Glu
            355                 360                 365

Glu Ile Ser Leu Gln Arg Asn Gln Ile Ser Leu Ile Lys Glu Asn Thr
        370                 375                 380

Phe Gln Gly Leu Thr Ser Leu Arg Ile Leu Asp Leu Ser Arg Asn Leu
385                 390                 395                 400

Ile Arg Glu Ile His Ser Gly Ala Phe Ala Lys Leu Gly Thr Ile Thr
            405                 410                 415

Asn Leu Asp Val Ser Phe Asn Glu Leu Thr Ser Phe Pro Thr Glu Gly
            420                 425                 430

Leu Asn Gly Leu Asn Gln Leu Lys Leu Val Gly Asn Phe Lys Leu Lys
        435                 440                 445

Asp Ala Leu Ala Ala Arg Asp Phe Ala Asn Leu Arg Ser Leu Ser Val
        450                 455                 460

Pro Tyr Ala Tyr Gln Cys Cys Ala Phe Trp Gly Cys Asp Ser Tyr Ala
465                 470                 475                 480

Asn Leu Asn Thr Glu Asp Asn Ser Pro Gln Glu His Ser Val Thr Lys
            485                 490                 495

Glu Lys Gly Lys Cys Ala Thr Asp Ala Ala Asn Val Thr Ser Thr Ala
            500                 505                 510

Glu Asn Glu Glu His Ser Gln Ile Ile His Cys Thr Pro Ser Thr
            515                 520                 525

Gly Ala Phe Lys Pro Cys Glu Tyr Leu Leu Gly Ser Trp Met Ile Arg
        530                 535                 540

Leu Thr Val Trp Phe Ile Phe Leu Val Ala Leu Leu Phe Asn Leu Leu
545                 550                 555                 560

Val Ile Leu Thr Val Phe Ala Ser Cys Ser Ser Leu Pro Ala Ser Lys
            565                 570                 575

Leu Phe Ile Gly Leu Ile Ser Val Ser Asn Leu Leu Met Gly Ile Tyr
        580                 585                 590

Thr Gly Ile Leu Thr Phe Leu Asp Ala Val Ser Trp Gly Arg Phe Ala
        595                 600                 605

Glu Phe Gly Ile Trp Trp Glu Thr Gly Ser Gly Cys Lys Val Ala Gly
        610                 615                 620

Ser Leu Ala Val Phe Ser Ser Glu Ser Ala Val Phe Leu Leu Thr Leu
625                 630                 635                 640

Ala Ala Val Glu Arg Ser Val Phe Ala Lys Asp Leu Met Lys His Gly
            645                 650                 655

Lys Ser Ser His Leu Arg Gln Phe Gln Val Ala Ala Leu Leu Ala Leu
            660                 665                 670

Leu Gly Ala Ala Val Ala Gly Cys Phe Pro Leu Phe His Gly Gly Gln
        675                 680                 685

Tyr Ser Ala Ser Pro Leu Cys Leu Pro Phe Pro Thr Gly Glu Thr Pro
        690                 695                 700

Ser Leu Gly Phe Thr Val Thr Leu Val Leu Leu Asn Ser Leu Ala Phe
705                 710                 715                 720

Leu Leu Met Ala Ile Ile Tyr Thr Lys Leu Tyr Cys Asn Leu Glu Lys
            725                 730                 735

Glu Asp Leu Ser Glu Asn Ser Gln Ser Ser Val Ile Lys His Val Ala

```
                    740                 745                 750
Trp Leu Ile Phe Thr Asn Cys Ile Phe Phe Cys Pro Val Ala Phe Phe
                755                 760                 765

Ser Phe Ala Pro Leu Ile Thr Ala Ile Ser Ile Ser Pro Glu Ile Met
            770                 775                 780

Lys Ser Val Thr Leu Ile Phe Phe Pro Leu Pro Ala Cys Leu Asn Pro
785                 790                 795                 800

Val Leu Tyr Val Phe Phe Asn Pro Lys Phe Lys Glu Asp Trp Lys Leu
                805                 810                 815

Leu Lys Arg Arg Val Thr Arg Lys His Gly Ser Val Ser Val Ser Ile
            820                 825                 830

Ser Ser Gln Gly Gly Cys Gly Glu Gln Asp Phe Tyr Tyr Asp Cys Gly
        835                 840                 845

Met Tyr Ser His Leu Gln Gly Asn Leu Thr Val Cys Asp Cys Glu
        850                 855                 860

Ser Phe Leu Leu Thr Lys Pro Val Ser Cys Lys His Leu Ile Lys Ser
865                 870                 875                 880

His Ser Cys Pro Val Leu Thr Ala Ala Ser Cys Gln Arg Pro Glu Ala
                885                 890                 895

Tyr Trp Ser Asp Cys Gly Thr Gln Ser Ala His Ser Asp Tyr Ala Asp
            900                 905                 910

Glu Glu Asp Ser Phe Val Ser Asp Ser Ser Asp Gln Val Gln Ala Cys
        915                 920                 925

Gly Arg Ala Cys Phe Tyr Gln Ser Arg Gly Phe Pro Leu Val Arg Tyr
    930                 935                 940

Ala Tyr Asn Leu Gln Arg Val Arg Asp
945                 950

<210> SEQ ID NO 54
<211> LENGTH: 951
<212> TYPE: PRT
<213> ORGANISM: Mus musculus

<400> SEQUENCE: 54

Met Pro Gly Pro Leu Gly Leu Leu Cys Cys Leu Ala Leu Gly Leu Leu
1               5                   10                  15

Gly Ser Ala Gly Pro Ser Gly Ala Ala Pro Leu Cys Ala Ala Pro
            20                  25                  30

Cys Ser Cys Asp Gly Asp Arg Arg Val Asp Cys Ser Gly Lys Gly Leu
        35                  40                  45

Thr Ala Val Pro Glu Gly Leu Ser Ala Phe Thr Gln Ala Leu Asp Ile
    50                  55                  60

Ser Met Asn Asn Ile Thr Gln Leu Pro Glu Asp Ala Phe Lys Asn Phe
65                  70                  75                  80

Pro Phe Leu Glu Glu Leu Gln Leu Ala Gly Asn Asp Leu Ser Phe Ile
                85                  90                  95

His Pro Lys Ala Leu Ser Gly Leu Lys Glu Leu Lys Val Leu Thr Leu
            100                 105                 110

Gln Asn Asn Gln Leu Lys Thr Val Pro Ser Glu Ala Ile Arg Gly Leu
        115                 120                 125

Ser Ala Leu Gln Ser Leu Arg Leu Asp Ala Asn His Ile Thr Ser Val
    130                 135                 140

Pro Glu Asp Ser Phe Glu Gly Leu Val Gln Leu Arg His Leu Trp Leu
145                 150                 155                 160
```

```
Asp Asp Asn Ser Leu Thr Glu Val Pro Val His Pro Leu Ser Asn Leu
                165                 170                 175

Pro Thr Leu Gln Ala Leu Thr Leu Ala Leu Asn Lys Ile Ser Ser Ile
            180                 185                 190

Pro Asp Phe Ala Phe Thr Asn Leu Ser Ser Leu Val Val Leu His Leu
        195                 200                 205

His Asn Asn Lys Ile Lys Ser Leu Ser Gln His Cys Phe Asp Gly Leu
    210                 215                 220

Asp Asn Leu Glu Thr Leu Asp Leu Asn Tyr Asn Leu Gly Glu Phe
225                 230                 235                 240

Pro Gln Ala Ile Lys Ala Leu Pro Ser Leu Lys Glu Leu Gly Phe His
                245                 250                 255

Ser Asn Ser Ile Ser Val Ile Pro Asp Gly Ala Phe Asp Gly Asn Pro
            260                 265                 270

Leu Leu Arg Thr Ile His Leu Tyr Asp Asn Pro Leu Ser Tyr Val Gly
        275                 280                 285

Asn Ser Ala Phe Arg Asn Leu Ser Asp Leu His Ser Leu Val Ile Arg
    290                 295                 300

Gly Ala Ser Met Val Gln Gln Phe Pro Asn Leu Thr Gly Thr Ala His
305                 310                 315                 320

Leu Glu Ser Leu Thr Leu Thr Gly Thr Lys Ile Ser Ser Ile Pro Asn
                325                 330                 335

Asn Leu Cys Gln Glu Gln Lys Met Leu Arg Thr Leu Asp Leu Ser Tyr
            340                 345                 350

Asn Asn Ile Arg Asp Leu Pro Ser Phe Asn Gly Cys His Ala Leu Glu
        355                 360                 365

Glu Ile Ser Leu Gln Arg Asn Gln Ile Tyr Gln Ile Lys Glu Gly Thr
    370                 375                 380

Phe Gln Gly Leu Ile Ser Leu Arg Ile Leu Asp Leu Ser Arg Asn Leu
385                 390                 395                 400

Ile His Glu Ile His Ser Lys Ala Phe Ala Thr Leu Gly Pro Ile Thr
                405                 410                 415

Asn Leu Asp Val Ser Phe Asn Glu Leu Thr Ser Phe Pro Thr Glu Gly
            420                 425                 430

Leu Asn Gly Leu Asn Gln Leu Lys Leu Val Gly Asn Phe Lys Leu Lys
        435                 440                 445

Glu Ala Leu Ala Ala Lys Asp Phe Val Asn Leu Arg Ser Leu Ser Val
    450                 455                 460

Pro Tyr Ala Tyr Gln Cys Cys Ala Phe Trp Gly Cys Asp Ser Tyr Ala
465                 470                 475                 480

Asn Leu Asn Thr Glu Asp Asn Ser Leu Gln Asp His Ser Val Ala Gln
                485                 490                 495

Glu Lys Gly Thr Ala Asp Ala Ala Asn Val Thr Ser Thr Val Glu Asn
            500                 505                 510

Glu Glu His Ser Gln Ile Ile Ile His Cys Thr Pro Ser Thr Gly Ala
        515                 520                 525

Phe Lys Pro Cys Glu Tyr Leu Leu Gly Ser Trp Met Ile Arg Leu Thr
    530                 535                 540

Val Trp Phe Ile Phe Leu Val Ala Leu Phe Phe Asn Leu Leu Val Ile
545                 550                 555                 560

Leu Thr Thr Phe Ala Ser Cys Thr Ser Leu Pro Ser Ser Lys Leu Phe
                565                 570                 575

Ile Gly Leu Ile Ser Val Ser Asn Leu Phe Met Gly Ile Tyr Thr Gly
```

```
            580             585             590
Ile Leu Thr Phe Leu Asp Ala Val Ser Trp Gly Arg Phe Ala Glu Phe
            595                 600             605

Gly Ile Trp Trp Glu Thr Gly Ser Gly Cys Lys Val Ala Gly Phe Leu
        610             615                 620

Ala Val Phe Ser Ser Glu Ser Ala Ile Phe Leu Met Leu Ala Thr
625             630             635                 640

Val Glu Arg Ser Leu Ser Ala Lys Asp Val Met Lys Asn Gly Lys Ser
                645             650             655

Asn His Leu Lys Gln Phe Arg Val Ala Ala Leu Leu Ala Phe Leu Gly
            660             665             670

Ala Thr Val Ala Gly Cys Phe Pro Leu Phe His Arg Gly Glu Tyr Ser
        675             680             685

Ala Ser Pro Leu Cys Leu Pro Phe Pro Thr Gly Glu Thr Pro Ser Leu
        690             695             700

Gly Phe Thr Val Thr Leu Val Leu Leu Asn Ser Leu Ala Phe Leu Leu
705             710             715             720

Met Ala Ile Ile Tyr Thr Lys Leu Tyr Cys Asn Leu Glu Lys Glu Asp
                725             730             735

Leu Ser Glu Asn Ser His Ser Ser Met Ile Lys His Val Ala Trp Leu
            740             745             750

Ile Phe Thr Asn Cys Ile Phe Phe Cys Pro Val Ala Phe Phe Ser Phe
            755             760             765

Ala Pro Leu Ile Thr Ala Ile Ser Ile Ser Pro Glu Ile Met Lys Ser
        770             775             780

Val Thr Leu Ile Phe Phe Pro Leu Pro Ala Cys Leu Asn Pro Val Leu
785             790             795             800

Tyr Val Phe Phe Asn Pro Lys Phe Lys Glu Asp Trp Lys Leu Leu Lys
                805             810             815

Arg Arg Val Thr Lys Lys Ser Gly Ser Val Ser Val Ser Ile Ser Ser
            820             825             830

Gln Gly Gly Cys Leu Glu Gln Asp Phe Tyr Tyr Asp Cys Gly Met Tyr
        835             840             845

Ser His Leu Gln Gly Asn Leu Thr Val Cys Asp Cys Cys Glu Ser Phe
        850             855             860

Leu Leu Thr Lys Pro Val Ser Cys Lys His Leu Ile Lys Ser His Ser
865             870             875             880

Cys Pro Ala Leu Ala Val Ala Ser Cys Gln Arg Pro Glu Gly Tyr Trp
                885             890             895

Ser Asp Cys Gly Thr Gln Ser Ala His Ser Tyr Ala Asp Glu Glu
            900             905             910

Asp Ser Phe Val Ser Asp Ser Ser Asp Gln Val Gln Ala Cys Gly Arg
            915             920             925

Ala Cys Phe Tyr Gln Ser Arg Gly Phe Pro Leu Val Arg Tyr Ala Tyr
        930             935             940

Asn Leu Pro Arg Val Lys Asp
945             950

<210> SEQ ID NO 55
<211> LENGTH: 907
<212> TYPE: PRT
<213> ORGANISM: Homo sapiens

<400> SEQUENCE: 55
```

```
Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
            35                  40                  45

Arg Val Asp Cys Ser Asp Leu Gly Leu Ser Glu Leu Pro Ser Asn Leu
        50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
                100                 105                 110

Leu Tyr Ser Leu Lys Val Leu Met Leu Gln Asn Asn Gln Leu Arg His
            115                 120                 125

Val Pro Thr Glu Ala Leu Gln Asn Leu Arg Ser Leu Gln Ser Leu Arg
        130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
                180                 185                 190

Leu Ala Leu Asn Lys Ile His His Ile Pro Asp Tyr Ala Phe Gly Asn
            195                 200                 205

Leu Ser Ser Leu Val Val Leu His Leu His Asn Asn Arg Ile His Ser
210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
        290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
            355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile Ile His Pro Asn
                405                 410                 415

Ala Phe Ser Thr Leu Pro Ser Leu Ile Lys Leu Asp Leu Ser Ser Asn
```

```
                420                 425                 430
Leu Leu Ser Ser Phe Pro Ile Thr Gly Leu His Gly Leu Thr His Leu
            435                 440                 445
Lys Leu Thr Gly Asn His Ala Leu Gln Ser Leu Ile Ser Ser Glu Asn
            450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Asp Leu His Lys Lys Asp Ala Gly
            500                 505                 510
Met Phe Gln Ala Gln Asp Glu Arg Asp Leu Glu Asp Phe Leu Leu Asp
            515                 520                 525
Phe Glu Glu Asp Leu Lys Ala Leu His Ser Val Gln Cys Ser Pro Ser
            530                 535                 540
Pro Gly Pro Phe Lys Pro Cys Glu His Leu Leu Asp Gly Trp Leu Ile
545                 550                 555                 560
Arg Ile Gly Val Trp Thr Ile Ala Val Leu Ala Leu Thr Cys Asn Ala
                565                 570                 575
Leu Val Thr Ser Thr Val Phe Arg Ser Pro Leu Tyr Ile Ser Pro Ile
            580                 585                 590
Lys Leu Leu Ile Gly Val Ile Ala Ala Val Asn Met Leu Thr Gly Val
            595                 600                 605
Ser Ser Ala Val Leu Ala Gly Val Asp Ala Phe Thr Phe Gly Ser Phe
            610                 615                 620
Ala Arg His Gly Ala Trp Trp Glu Asn Gly Val Gly Cys His Val Ile
625                 630                 635                 640
Gly Phe Leu Ser Ile Phe Ala Ser Glu Ser Ser Val Phe Leu Leu Thr
                645                 650                 655
Leu Ala Ala Leu Glu Arg Gly Phe Ser Val Lys Tyr Ser Ala Lys Phe
            660                 665                 670
Glu Thr Lys Ala Pro Phe Ser Ser Leu Lys Val Ile Ile Leu Leu Cys
            675                 680                 685
Ala Leu Leu Ala Leu Thr Met Ala Ala Val Pro Leu Leu Gly Gly Ser
            690                 695                 700
Lys Tyr Gly Ala Ser Pro Leu Cys Leu Pro Leu Pro Phe Gly Glu Pro
705                 710                 715                 720
Ser Thr Met Gly Tyr Met Val Ala Leu Ile Leu Leu Asn Ser Leu Cys
                725                 730                 735
Phe Leu Met Met Thr Ile Ala Tyr Thr Lys Leu Tyr Cys Asn Leu Asp
            740                 745                 750
Lys Gly Asp Leu Glu Asn Ile Trp Asp Cys Ser Met Val Lys His Ile
            755                 760                 765
Ala Leu Leu Leu Phe Thr Asn Cys Ile Leu Asn Cys Pro Val Ala Phe
            770                 775                 780
Leu Ser Phe Ser Ser Leu Ile Asn Leu Thr Phe Ile Ser Pro Glu Val
785                 790                 795                 800
Ile Lys Phe Ile Leu Leu Val Val Val Pro Leu Pro Ala Cys Leu Asn
                805                 810                 815
Pro Leu Leu Tyr Ile Leu Phe Asn Pro His Phe Lys Glu Asp Leu Val
            820                 825                 830
Ser Leu Arg Lys Gln Thr Tyr Val Trp Thr Arg Ser Lys His Pro Ser
            835                 840                 845
```

Leu Met Ser Ile Asn Ser Asp Asp Val Glu Lys Gln Ser Cys Asp Ser
            850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905

<210> SEQ ID NO 56
<211> LENGTH: 907
<212> TYPE: PRT
<213> ORGANISM: Rattus norvegicus

<400> SEQUENCE: 56

Met Asp Thr Ser Arg Val Arg Met Leu Leu Ser Leu Ala Leu Leu
1               5                   10                  15

Gln Leu Val Ala Ala Gly Ser Pro Pro Arg Pro Asp Thr Met Pro Arg
                20                  25                  30

Gly Cys Pro Ser Tyr Cys His Cys Glu Leu Asp Gly Arg Met Leu Leu
            35                  40                  45

Arg Val Asp Cys Ser Asp Leu Gly Leu Ser Glu Leu Pro Ser Asn Leu
50                  55                  60

Ser Val Phe Thr Ser Tyr Leu Asp Leu Ser Met Asn Asn Ile Ser Gln
65                  70                  75                  80

Leu Pro Ala Ser Leu Leu His Arg Leu Arg Phe Leu Glu Glu Leu Arg
                85                  90                  95

Leu Ala Gly Asn Ala Leu Thr His Ile Pro Lys Gly Ala Phe Ala Gly
            100                 105                 110

Leu His Ser Leu Lys Val Leu Met Leu Gln Asn Asn Gln Leu Arg Gln
            115                 120                 125

Val Pro Glu Glu Ala Leu Gln Asn Leu Arg Ser Leu Gln Ser Leu Arg
        130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Asp
                165                 170                 175

Val Pro Val Gln Ala Phe Arg Ser Leu Ser Ala Leu Gln Ala Met Thr
            180                 185                 190

Leu Ala Leu Asn Lys Ile His His Ile Ala Asp His Ala Phe Gly Asn
            195                 200                 205

Leu Ser Ser Leu Val Val Leu His Leu His Asn Asn Arg Ile His Ser
        210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Lys Thr Leu
                245                 250                 255

Ser Asn Leu Lys Glu Leu Gly Phe His Ser Asn Asn Ile Arg Ser Ile
            260                 265                 270

Pro Glu Arg Ala Phe Val Gly Asn Pro Ser Leu Ile Thr Ile His Phe
            275                 280                 285

Tyr Asp Asn Pro Ile Gln Phe Val Gly Ile Ser Ala Phe Gln His Leu
        290                 295                 300

Pro Glu Leu Arg Thr Leu Thr Leu Asn Gly Ala Ser Gln Ile Thr Glu

-continued

```
              305                 310                 315                 320
              Phe Pro Asp Leu Thr Gly Thr Ala Thr Leu Glu Ser Leu Thr Leu Thr
                              325                 330                 335
              Gly Ala Lys Ile Ser Ser Leu Pro Gln Thr Val Cys Asp Gln Leu Pro
                              340                 345                 350
              Asn Leu Gln Val Leu Asp Leu Ser Tyr Asn Leu Leu Glu Asp Leu Pro
                              355                 360                 365
              Ser Leu Ser Gly Cys Gln Lys Leu Gln Lys Ile Asp Leu Arg His Asn
                              370                 375                 380
              Glu Ile Tyr Glu Ile Lys Gly Gly Thr Phe Gln Gln Leu Phe Asn Leu
              385                 390                 395                 400
              Arg Ser Leu Asn Leu Ala Arg Asn Lys Ile Ala Ile His Pro Asn
                              405                 410                 415
              Ala Phe Ser Thr Leu Pro Ser Leu Ile Lys Leu Asp Leu Ser Ser Asn
                              420                 425                 430
              Leu Leu Ser Ser Phe Pro Val Thr Gly Leu His Gly Leu Thr His Leu
                              435                 440                 445
              Lys Leu Thr Gly Asn Arg Ala Leu Gln Ser Leu Ile Pro Ser Ala Asn
                              450                 455                 460
              Phe Pro Glu Leu Lys Ile Ile Glu Met Pro Tyr Ala Tyr Gln Cys Cys
              465                 470                 475                 480
              Ala Phe Gly Gly Cys Glu Asn Val Tyr Lys Ile Pro Asn Gln Trp Asn
                              485                 490                 495
              Lys Asp Asp Ser Ser Val Asp Asp Leu Arg Lys Lys Asp Ala Gly
                              500                 505                 510
              Leu Phe Gln Val Gln Asp Glu Arg Asp Leu Glu Asp Phe Leu Leu Asp
                              515                 520                 525
              Phe Glu Glu Asp Leu Lys Val Leu His Ser Val Gln Cys Ser Pro Pro
                              530                 535                 540
              Pro Gly Pro Phe Lys Pro Cys Glu His Leu Phe Gly Ser Trp Leu Ile
              545                 550                 555                 560
              Arg Ile Gly Val Trp Thr Thr Ala Val Leu Ala Leu Ser Cys Asn Ala
                              565                 570                 575
              Leu Val Ala Phe Thr Val Phe Arg Thr Pro Leu Tyr Ile Ser Ser Ile
                              580                 585                 590
              Lys Leu Leu Ile Gly Val Ile Ala Val Val Asp Ile Leu Met Gly Val
                              595                 600                 605
              Ser Ser Ala Ile Leu Ala Val Val Asp Thr Phe Thr Phe Gly Ser Phe
                              610                 615                 620
              Ala Gln His Gly Ala Trp Trp Glu Gly Gly Ile Gly Cys Gln Ile Val
              625                 630                 635                 640
              Gly Phe Leu Ser Ile Phe Ala Ser Glu Ser Val Phe Leu Leu Thr
                              645                 650                 655
              Leu Ala Ala Leu Glu Arg Gly Phe Ser Val Lys Cys Ser Ser Lys Phe
                              660                 665                 670
              Glu Met Lys Ala Pro Leu Ser Ser Leu Lys Ala Ile Ile Leu Leu Cys
                              675                 680                 685
              Val Leu Leu Ala Leu Thr Ile Ala Thr Val Pro Leu Leu Gly Gly Ser
                              690                 695                 700
              Glu Tyr Asn Ala Ser Pro Leu Cys Leu Pro Leu Pro Phe Gly Glu Pro
              705                 710                 715                 720
              Ser Thr Thr Gly Tyr Met Val Ala Leu Val Leu Leu Asn Ser Leu Cys
                              725                 730                 735
```

```
Phe Leu Ile Met Thr Ile Ala Tyr Thr Arg Leu Tyr Cys Ser Leu Glu
                740                 745                 750

Lys Gly Glu Leu Glu Asn Leu Trp Asp Cys Ser Met Val Lys His Thr
                755                 760                 765

Ala Leu Leu Leu Phe Thr Asn Cys Ile Leu Tyr Cys Pro Val Ala Phe
                770                 775                 780

Leu Ser Phe Ser Ser Leu Leu Asn Leu Thr Phe Ile Ser Pro Glu Val
785                 790                 795                 800

Ile Lys Phe Ile Leu Leu Val Ile Val Pro Leu Pro Ala Cys Leu Asn
                805                 810                 815

Pro Leu Leu Tyr Ile Val Phe Asn Pro His Phe Lys Glu Asp Met Gly
                820                 825                 830

Ser Leu Gly Lys Gln Thr Arg Phe Trp Thr Arg Ala Lys His Pro Ser
                835                 840                 845

Leu Leu Ser Ile Asn Ser Asp Asp Val Glu Lys Arg Ser Cys Asp Ser
                850                 855                 860

Thr Gln Ala Leu Val Ser Phe Thr His Ala Ser Ile Ala Tyr Asp Leu
865                 870                 875                 880

Pro Ser Asp Ser Gly Ser Ser Pro Ala Tyr Pro Met Thr Glu Ser Cys
                885                 890                 895

His Leu Ser Ser Val Ala Phe Val Pro Cys Leu
                900                 905

<210> SEQ ID NO 57
<211> LENGTH: 907
<212> TYPE: PRT
<213> ORGANISM: Mus musculus

<400> SEQUENCE: 57

Met Asp Thr Ser Cys Val His Met Leu Leu Ser Leu Ala Leu Leu
1               5                   10                  15

Gln Leu Val Ala Ala Gly Ser Ser Pro Gly Pro Asp Ala Ile Pro Arg
                20                  25                  30

Gly Cys Pro Ser His Cys His Cys Glu Leu Asp Gly Arg Met Leu Leu
                35                  40                  45

Arg Val Asp Cys Ser Asp Leu Gly Leu Ser Glu Leu Pro Ser Asn Leu
50                  55                  60

Ser Val Phe Thr Ser Tyr Leu Asp Leu Ser Met Asn Asn Ile Ser Gln
65                  70                  75                  80

Leu Pro Ala Ser Leu Leu His Arg Leu Cys Phe Leu Glu Glu Leu Arg
                85                  90                  95

Leu Ala Gly Asn Ala Leu Thr His Ile Pro Lys Gly Ala Phe Thr Gly
                100                 105                 110

Leu His Ser Leu Lys Val Leu Met Leu Gln Asn Asn Gln Leu Arg Gln
                115                 120                 125

Val Pro Glu Glu Ala Leu Gln Asn Leu Arg Ser Leu Gln Ser Leu Arg
                130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Asp
                165                 170                 175

Val Pro Val Gln Ala Phe Arg Ser Leu Ser Ala Leu Gln Ala Met Thr
                180                 185                 190

Leu Ala Leu Asn Lys Ile His His Ile Ala Asp Tyr Ala Phe Gly Asn
```

```
            195                 200                 205
Leu Ser Ser Leu Val Val Leu His Leu His Asn Asn Arg Ile His Ser
            210                 215                 220
Leu Gly Lys Lys Cys Phe Asp Gly Leu His Ser Leu Glu Thr Leu Asp
225                 230                 235                 240
Leu Asn Tyr Asn Asn Leu Asp Glu Phe Pro Thr Ala Ile Lys Thr Leu
            245                 250                 255
Ser Asn Leu Lys Glu Leu Gly Phe His Ser Asn Asn Ile Arg Ser Ile
            260                 265                 270
Pro Glu Arg Ala Phe Val Gly Asn Pro Ser Leu Ile Thr Ile His Phe
            275                 280                 285
Tyr Asp Asn Pro Ile Gln Phe Val Gly Val Ser Ala Phe Gln His Leu
            290                 295                 300
Pro Glu Leu Arg Thr Leu Thr Leu Asn Gly Ala Ser His Ile Thr Glu
305                 310                 315                 320
Phe Pro His Leu Thr Gly Thr Ala Thr Leu Glu Ser Leu Thr Leu Thr
            325                 330                 335
Gly Ala Lys Ile Ser Ser Leu Pro Gln Ala Val Cys Asp Gln Leu Pro
            340                 345                 350
Asn Leu Gln Val Leu Asp Leu Ser Tyr Asn Leu Leu Glu Asp Leu Pro
            355                 360                 365
Ser Leu Ser Gly Cys Gln Lys Leu Gln Lys Ile Asp Leu Arg His Asn
            370                 375                 380
Glu Ile Tyr Glu Ile Lys Gly Ser Thr Phe Gln Gln Leu Phe Asn Leu
385                 390                 395                 400
Arg Ser Leu Asn Leu Ala Trp Asn Lys Ile Ala Ile His Pro Asn
            405                 410                 415
Ala Phe Ser Thr Leu Pro Ser Leu Ile Lys Leu Asp Leu Ser Ser Asn
            420                 425                 430
Leu Leu Ser Ser Phe Pro Val Thr Gly Leu His Gly Leu Thr His Leu
            435                 440                 445
Lys Leu Thr Gly Asn Arg Ala Leu Gln Ser Leu Ile Pro Ser Ala Asn
            450                 455                 460
Phe Pro Glu Leu Lys Ile Ile Glu Met Pro Ser Ala Tyr Gln Cys Cys
465                 470                 475                 480
Ala Phe Gly Gly Cys Glu Asn Val Tyr Lys Ile Ser Asn Gln Trp Asn
            485                 490                 495
Lys Asp Asp Gly Asn Ser Val Asp Leu His Lys Lys Asp Ala Gly
                500                 505                 510
Leu Phe Gln Val Gln Asp Glu Arg Asp Leu Glu Asp Phe Leu Leu Asp
            515                 520                 525
Phe Glu Glu Asp Leu Lys Ala Leu His Ser Val Gln Cys Ser Pro Ser
            530                 535                 540
Pro Gly Pro Phe Lys Pro Cys Glu His Leu Phe Gly Ser Trp Leu Ile
545                 550                 555                 560
Arg Ile Gly Val Trp Thr Thr Ala Val Leu Ala Leu Ser Cys Asn Ala
                565                 570                 575
Leu Val Ala Leu Thr Val Phe Arg Thr Pro Leu Tyr Ile Ser Ser Ile
            580                 585                 590
Lys Leu Leu Ile Gly Val Ile Ala Val Asp Ile Leu Met Gly Val
            595                 600                 605
Ser Ser Ala Val Leu Ala Ala Val Asp Ala Phe Thr Phe Gly Arg Phe
            610                 615                 620
```

Ala Gln His Gly Ala Trp Trp Glu Asp Gly Ile Gly Cys Gln Ile Val
625                 630                 635                 640

Gly Phe Leu Ser Ile Phe Ala Ser Glu Ser Ile Phe Leu Leu Thr
        645                 650                 655

Leu Ala Ala Leu Glu Arg Gly Phe Ser Val Lys Cys Ser Ser Lys Phe
            660                 665                 670

Glu Val Lys Ala Pro Leu Phe Ser Leu Arg Ala Ile Val Leu Leu Cys
            675                 680                 685

Val Leu Leu Ala Leu Thr Ile Ala Thr Ile Pro Leu Leu Gly Gly Ser
690                 695                 700

Lys Tyr Asn Ala Ser Pro Leu Cys Leu Pro Leu Pro Phe Gly Glu Pro
705                 710                 715                 720

Ser Thr Thr Gly Tyr Met Val Ala Leu Val Leu Leu Asn Ser Leu Cys
                725                 730                 735

Phe Leu Ile Met Thr Ile Ala Tyr Thr Lys Leu Tyr Cys Ser Leu Glu
                740                 745                 750

Lys Gly Glu Leu Glu Asn Leu Trp Asp Cys Ser Met Val Lys His Ile
        755                 760                 765

Ala Leu Leu Leu Phe Ala Asn Cys Ile Leu Tyr Cys Pro Val Ala Phe
770                 775                 780

Leu Ser Phe Ser Ser Leu Leu Asn Leu Thr Phe Ile Ser Pro Asp Val
785                 790                 795                 800

Ile Lys Phe Ile Leu Leu Val Ile Val Pro Leu Pro Ser Cys Leu Asn
                805                 810                 815

Pro Leu Leu Tyr Ile Val Phe Asn Pro His Phe Lys Glu Asp Met Gly
                820                 825                 830

Ser Leu Gly Lys His Thr Arg Phe Trp Met Arg Ser Lys His Ala Ser
        835                 840                 845

Leu Leu Ser Ile Asn Ser Asp Asp Val Glu Lys Arg Ser Cys Glu Ser
850                 855                 860

Thr Gln Ala Leu Val Ser Phe Thr His Ala Ser Ile Ala Tyr Asp Leu
865                 870                 875                 880

Pro Ser Thr Ser Gly Ala Ser Pro Ala Tyr Pro Met Thr Glu Ser Cys
                885                 890                 895

His Leu Ser Ser Val Ala Phe Val Pro Cys Leu
            900                 905

<210> SEQ ID NO 58
<211> LENGTH: 967
<212> TYPE: PRT
<213> ORGANISM: Homo sapiens

<400> SEQUENCE: 58

Met Pro Ser Pro Pro Gly Leu Arg Ala Leu Trp Leu Cys Ala Ala Leu
1               5                   10                  15

Cys Ala Ser Arg Arg Ala Gly Gly Ala Pro Gln Pro Gly Pro Gly Pro
            20                  25                  30

Thr Ala Cys Pro Ala Pro Cys His Cys Gln Glu Asp Gly Ile Met Leu
        35                  40                  45

Ser Ala Asp Cys Ser Glu Leu Gly Leu Ser Ala Val Pro Gly Asp Leu
    50                  55                  60

Asp Pro Leu Thr Ala Tyr Leu Asp Leu Ser Met Asn Asn Leu Thr Glu
65                  70                  75                  80

Leu Gln Pro Gly Leu Phe His His Leu Arg Phe Leu Glu Glu Leu Arg

```
                        85                  90                  95
Leu Ser Gly Asn His Leu Ser His Ile Pro Gly Gln Ala Phe Ser Gly
                100                 105                 110
Leu Tyr Ser Leu Lys Ile Leu Met Leu Gln Asn Asn Gln Leu Gly Gly
                115                 120                 125
Ile Pro Ala Glu Ala Leu Trp Glu Leu Pro Ser Leu Gln Ser Leu Arg
            130                 135                 140
Leu Asp Ala Asn Leu Ile Ser Leu Val Pro Glu Arg Ser Phe Glu Gly
145                 150                 155                 160
Leu Ser Ser Leu Arg His Leu Trp Leu Asp Asp Asn Ala Leu Thr Glu
                165                 170                 175
Ile Pro Val Arg Ala Leu Asn Asn Leu Pro Ala Leu Gln Ala Met Thr
            180                 185                 190
Leu Ala Leu Asn Arg Ile Ser His Ile Pro Asp Tyr Ala Phe Gln Asn
            195                 200                 205
Leu Thr Ser Leu Val Val Leu His Leu His Asn Asn Arg Ile Gln His
        210                 215                 220
Leu Gly Thr His Ser Phe Glu Gly Leu His Asn Leu Glu Thr Leu Asp
225                 230                 235                 240
Leu Asn Tyr Asn Lys Leu Gln Glu Phe Pro Val Ala Ile Arg Thr Leu
                245                 250                 255
Gly Arg Leu Gln Glu Leu Gly Phe His Asn Asn Asn Ile Lys Ala Ile
            260                 265                 270
Pro Glu Lys Ala Phe Met Gly Asn Pro Leu Leu Gln Thr Ile His Phe
        275                 280                 285
Tyr Asp Asn Pro Ile Gln Phe Val Gly Arg Ser Ala Phe Gln Tyr Leu
            290                 295                 300
Pro Lys Leu His Thr Leu Ser Leu Asn Gly Ala Met Asp Ile Gln Glu
305                 310                 315                 320
Phe Pro Asp Leu Lys Gly Thr Thr Ser Leu Glu Ile Leu Thr Leu Thr
                325                 330                 335
Arg Ala Gly Ile Arg Leu Leu Pro Ser Gly Met Cys Gln Gln Leu Pro
            340                 345                 350
Arg Leu Arg Val Leu Glu Leu Ser His Asn Gln Ile Glu Glu Leu Pro
        355                 360                 365
Ser Leu His Arg Cys Gln Lys Leu Glu Glu Ile Gly Leu Gln His Asn
        370                 375                 380
Arg Ile Trp Glu Ile Gly Ala Asp Thr Phe Ser Gln Leu Ser Ser Leu
385                 390                 395                 400
Gln Ala Leu Asp Leu Ser Trp Asn Ala Ile Arg Ser Ile His Pro Glu
            405                 410                 415
Ala Phe Ser Thr Leu His Ser Leu Val Lys Leu Asp Leu Thr Asp Asn
            420                 425                 430
Gln Leu Thr Thr Leu Pro Leu Ala Gly Leu Gly Gly Leu Met His Leu
        435                 440                 445
Lys Leu Lys Gly Asn Leu Ala Leu Ser Gln Ala Phe Ser Lys Asp Ser
    450                 455                 460
Phe Pro Lys Leu Arg Ile Leu Glu Val Pro Tyr Ala Tyr Gln Cys Cys
465                 470                 475                 480
Pro Tyr Gly Met Cys Ala Ser Phe Phe Lys Ala Ser Gly Gln Trp Glu
            485                 490                 495
Ala Glu Asp Leu His Leu Asp Asp Glu Glu Ser Ser Lys Arg Pro Leu
            500                 505                 510
```

```
Gly Leu Leu Ala Arg Gln Ala Glu Asn His Tyr Asp Gln Asp Leu Asp
            515                 520                 525

Glu Leu Gln Leu Glu Met Glu Asp Ser Lys Pro His Pro Ser Val Gln
            530                 535                 540

Cys Ser Pro Thr Pro Gly Pro Phe Lys Pro Cys Glu Tyr Leu Phe Glu
545                 550                 555                 560

Ser Trp Gly Ile Arg Leu Ala Val Trp Ala Ile Val Leu Leu Ser Val
            565                 570                 575

Leu Cys Asn Gly Leu Val Leu Leu Thr Val Phe Ala Gly Gly Pro Val
            580                 585                 590

Pro Leu Pro Pro Val Lys Phe Val Val Gly Ala Ile Ala Gly Ala Asn
            595                 600                 605

Thr Leu Thr Gly Ile Ser Cys Gly Leu Leu Ala Ser Val Asp Ala Leu
            610                 615                 620

Thr Phe Gly Gln Phe Ser Glu Tyr Gly Ala Arg Trp Glu Thr Gly Leu
625                 630                 635                 640

Gly Cys Arg Ala Thr Gly Phe Leu Ala Val Leu Gly Ser Glu Ala Ser
            645                 650                 655

Val Leu Leu Leu Thr Leu Ala Ala Val Gln Cys Ser Val Ser Val Ser
            660                 665                 670

Cys Val Arg Ala Tyr Gly Lys Ser Pro Ser Leu Gly Ser Val Arg Ala
            675                 680                 685

Gly Val Leu Gly Cys Leu Ala Leu Ala Gly Leu Ala Ala Ala Leu Pro
            690                 695                 700

Leu Ala Ser Val Gly Glu Tyr Gly Ala Ser Pro Leu Cys Leu Pro Tyr
705                 710                 715                 720

Ala Pro Pro Glu Gly Gln Pro Ala Ala Leu Gly Phe Thr Val Ala Leu
            725                 730                 735

Val Met Met Asn Ser Phe Cys Phe Leu Val Val Ala Gly Ala Tyr Ile
            740                 745                 750

Lys Leu Tyr Cys Asp Leu Pro Arg Gly Asp Phe Glu Ala Val Trp Asp
            755                 760                 765

Cys Ala Met Val Arg His Val Ala Trp Leu Ile Phe Ala Asp Gly Leu
            770                 775                 780

Leu Tyr Cys Pro Val Ala Phe Leu Ser Phe Ala Ser Met Leu Gly Leu
785                 790                 795                 800

Phe Pro Val Thr Pro Glu Ala Val Lys Ser Val Leu Val Val Leu
            805                 810                 815

Pro Leu Pro Ala Cys Leu Asn Pro Leu Leu Tyr Leu Leu Phe Asn Pro
            820                 825                 830

His Phe Arg Asp Asp Leu Arg Arg Leu Arg Pro Arg Ala Gly Asp Ser
            835                 840                 845

Gly Pro Leu Ala Tyr Ala Ala Ala Gly Glu Leu Glu Lys Ser Ser Cys
            850                 855                 860

Asp Ser Thr Gln Ala Leu Val Ala Phe Ser Asp Val Asp Leu Ile Leu
865                 870                 875                 880

Glu Ala Ser Glu Ala Gly Arg Pro Pro Gly Leu Glu Thr Tyr Gly Phe
            885                 890                 895

Pro Ser Val Thr Leu Ile Ser Cys Gln Gln Pro Gly Ala Pro Arg Leu
            900                 905                 910

Glu Gly Ser His Cys Val Glu Pro Glu Gly Asn His Phe Gly Asn Pro
            915                 920                 925
```

```
Gln Pro Ser Met Asp Gly Glu Leu Leu Arg Ala Glu Gly Ser Thr
    930                 935                 940

Pro Ala Gly Gly Gly Leu Ser Gly Gly Gly Phe Gln Pro Ser Gly
945                 950                 955                 960

Leu Ala Phe Ala Ser His Val
                    965

<210> SEQ ID NO 59
<211> LENGTH: 965
<212> TYPE: PRT
<213> ORGANISM: Rattus norvegicus

<400> SEQUENCE: 59

Met His Ser Ser Pro Leu Leu Ala Leu Cys Leu Cys Val Val Leu
1               5                   10                  15

Cys Ala Leu Ala Arg Ala Gly Ser Asp Pro Gln Pro Gly Pro Gly Arg
            20                  25                  30

Pro Ala Cys Pro Ala Pro Cys His Cys Gln Glu Asp Gly Ile Met Leu
            35                  40                  45

Ser Ala Asp Cys Ser Glu Leu Gly Leu Ser Glu Val Pro Ala Asp Leu
50                  55                  60

Asp Pro Leu Thr Ala Tyr Leu Asp Leu Ser Met Asn Asn Leu Thr Glu
65                  70                  75                  80

Leu Gln Pro Gly Leu Phe His His Leu Arg Phe Leu Glu Glu Leu Arg
            85                  90                  95

Leu Ser Gly Asn His Leu Ser His Ile Pro Arg Gln Ala Phe Ser Gly
            100                 105                 110

Leu His Ser Leu Lys Ile Leu Met Leu Gln Ser Asn Gln Leu Arg Gly
            115                 120                 125

Ile Pro Ala Glu Ala Leu Trp Glu Leu Pro Ser Leu Gln Ser Leu Arg
            130                 135                 140

Leu Asp Ala Asn Leu Ile Ser Leu Val Pro Glu Arg Ser Phe Glu Gly
145                 150                 155                 160

Leu Ser Ser Leu Arg His Leu Trp Leu Asp Asp Asn Ala Leu Thr Glu
            165                 170                 175

Ile Pro Val Arg Ala Leu Asn Asn Leu Pro Ala Leu Gln Ala Met Thr
            180                 185                 190

Leu Ala Leu Asn Arg Ile Arg His Ile Pro Asp Tyr Ala Phe Gln Asn
            195                 200                 205

Leu Thr Ser Leu Val Val Leu His Leu His Asn Asn Arg Ile Gln His
210                 215                 220

Val Gly Thr His Ser Phe Glu Gly Leu His Asn Leu Glu Thr Leu Asp
225                 230                 235                 240

Leu Asn Tyr Asn Glu Leu Gln Glu Phe Pro Val Ala Ile Arg Thr Leu
            245                 250                 255

Gly Arg Leu Gln Glu Leu Gly Phe His Asn Asn Asn Ile Lys Ala Ile
            260                 265                 270

Pro Glu Lys Ala Phe Met Gly Asn Pro Leu Leu Gln Thr Ile His Phe
            275                 280                 285

Tyr Asp Asn Pro Ile Gln Phe Val Gly Arg Ser Ala Phe Gln Tyr Leu
            290                 295                 300

Ser Lys Leu His Thr Leu Ser Leu Asn Gly Ala Thr Asp Ile Gln Glu
305                 310                 315                 320

Phe Pro Asp Leu Lys Gly Thr Thr Ser Leu Glu Ile Leu Thr Leu Thr
            325                 330                 335
```

-continued

```
Arg Ala Gly Ile Arg Leu Leu Pro Ala Gly Met Cys Gln Gln Leu Pro
            340                 345                 350

Arg Leu Arg Ile Leu Glu Leu Ser His Asn Gln Ile Glu Glu Leu Pro
            355                 360                 365

Ser Leu His Arg Cys Gln Lys Leu Glu Glu Ile Gly Leu Gln His Asn
        370                 375                 380

Arg Ile Trp Glu Ile Gly Ala Asp Thr Phe Ser Gln Leu Ser Ser Leu
385                 390                 395                 400

Gln Ala Leu Asp Leu Ser Trp Asn Ala Ile Arg Ala Ile His Pro Glu
                405                 410                 415

Ala Phe Ser Thr Leu Arg Ser Leu Val Lys Leu Asp Leu Thr Asp Asn
            420                 425                 430

Gln Leu Thr Thr Leu Pro Leu Ala Gly Leu Gly Gly Leu Met His Leu
            435                 440                 445

Lys Leu Lys Gly Asn Leu Ala Leu Ser Gln Ala Phe Ser Lys Asp Ser
        450                 455                 460

Phe Pro Lys Leu Arg Ile Leu Glu Val Pro Tyr Ala Tyr Gln Cys Cys
465                 470                 475                 480

Ala Tyr Gly Leu Cys Ala Asn Phe Phe Lys Thr Ser Gly Gln Trp Gln
                485                 490                 495

Ala Glu Asp Phe His Ala Glu Glu Glu Ala Pro Lys Arg Pro Leu
            500                 505                 510

Gly Leu Leu Ala Gly Gln Ala Glu Asn His Tyr Asp Leu Asp Leu Asp
            515                 520                 525

Glu Leu Gln Met Glu Thr Glu Asp Ser Lys Pro His Pro Ser Val Gln
        530                 535                 540

Cys Ser Pro Val Pro Gly Pro Phe Lys Pro Cys Glu His Leu Phe Glu
545                 550                 555                 560

Ser Trp Gly Ile Arg Leu Ala Val Trp Ala Ile Val Leu Leu Ser Val
                565                 570                 575

Leu Cys Asn Gly Leu Val Leu Leu Thr Val Phe Ala Gly Gly Pro Ser
            580                 585                 590

Pro Leu Ser Pro Val Lys Leu Val Val Gly Ala Ile Ala Gly Ala Asn
            595                 600                 605

Ala Leu Thr Gly Ile Ser Cys Gly Leu Leu Ala Ser Val Asp Ala Leu
            610                 615                 620

Thr Phe Gly Gln Phe Ala Glu Tyr Gly Ala Arg Trp Glu Thr Gly Leu
625                 630                 635                 640

Gly Cys Gln Ala Thr Gly Phe Leu Ala Val Leu Gly Ser Glu Ala Ser
                645                 650                 655

Val Leu Leu Leu Thr Leu Ala Ala Val Gln Cys Ser Val Ser Val Thr
            660                 665                 670

Cys Val Arg Ala Tyr Gly Lys Ala Pro Ser Pro Gly Ser Val Arg Ala
            675                 680                 685

Gly Ala Leu Gly Cys Leu Ala Leu Ala Gly Leu Ala Ala Ala Leu Pro
        690                 695                 700

Leu Ala Ser Val Gly Glu Tyr Gly Ala Ser Pro Leu Cys Leu Pro Tyr
705                 710                 715                 720

Ala Pro Pro Glu Gly Arg Pro Ala Ala Leu Gly Phe Ala Val Ala Leu
                725                 730                 735

Val Met Met Asn Ser Leu Cys Phe Leu Val Val Ala Gly Ala Tyr Ile
            740                 745                 750
```

```
Lys Leu Tyr Cys Asp Leu Pro Arg Gly Asp Phe Glu Ala Val Trp Asp
            755                 760                 765

Cys Ala Met Val Arg His Val Ala Trp Leu Ile Phe Ala Asp Gly Leu
770                 775                 780

Leu Tyr Cys Pro Val Ala Phe Leu Ser Phe Ala Ser Met Leu Gly Leu
785                 790                 795                 800

Phe Pro Val Thr Pro Glu Ala Val Lys Ser Val Leu Leu Val Val Leu
                805                 810                 815

Pro Leu Pro Ala Cys Leu Asn Pro Leu Tyr Leu Leu Phe Asn Pro
            820                 825                 830

His Phe Arg Glu Asp Leu Arg Arg Leu Trp Pro Ser Pro Arg Ser Pro
            835                 840                 845

Gly Pro Leu Ala Tyr Thr Ala Ala Gly Glu Leu Glu Lys Ser Ser Cys
850                 855                 860

Asp Ser Thr Gln Ala Leu Val Ala Phe Ser Asp Val Asp Leu Ile Leu
865                 870                 875                 880

Glu Ala Ser Glu Ala Gly Gln Pro Pro Gly Leu Glu Thr Tyr Gly Phe
                885                 890                 895

Pro Ser Val Thr Leu Ile Ser Arg His Gln Pro Gly Ala Thr Arg Leu
                900                 905                 910

Glu Gly Asn His Phe Val Glu Pro Asp Gly Thr Lys Leu Gly Asn Pro
            915                 920                 925

Gln Pro Pro Met Asn Glu Glu Leu Leu Leu Arg Ala Glu Gly Ala Thr
            930                 935                 940

Leu Ala Asp Cys Ser Ala Gly Gly Ala Leu Trp Pro Ser Gly Pro Leu
945                 950                 955                 960

Phe Ala Ser His Leu
                965

<210> SEQ ID NO 60
<211> LENGTH: 967
<212> TYPE: PRT
<213> ORGANISM: Mus musculus

<400> SEQUENCE: 60

Met His Ser Pro Pro Gly Leu Leu Ala Leu Trp Leu Cys Ala Val Leu
1               5                   10                  15

Cys Ala Ser Ala Arg Ala Gly Ser Asp Pro Gln Pro Gly Pro Gly Arg
                20                  25                  30

Pro Ala Cys Pro Ala Pro Cys His Cys Gln Glu Asp Gly Ile Met Leu
            35                  40                  45

Ser Ala Asp Cys Ser Glu Leu Gly Leu Ser Val Val Pro Ala Asp Leu
50                  55                  60

Asp Pro Leu Thr Ala Tyr Leu Asp Leu Ser Met Asn Asn Leu Thr Glu
65                  70                  75                  80

Leu Gln Pro Gly Leu Phe His His Leu Arg Phe Leu Glu Glu Leu Arg
                85                  90                  95

Leu Ser Gly Asn His Leu Ser His Ile Pro Gly Gln Ala Phe Ser Gly
            100                 105                 110

Leu His Ser Leu Lys Ile Leu Met Leu Gln Ser Asn Gln Leu Arg Gly
            115                 120                 125

Ile Pro Ala Glu Ala Leu Trp Glu Leu Pro Ser Leu Gln Ser Leu Arg
130                 135                 140

Leu Asp Ala Asn Leu Ile Ser Leu Val Pro Glu Arg Ser Phe Glu Gly
145                 150                 155                 160
```

```
Leu Ser Ser Leu Arg His Leu Trp Leu Asp Asp Asn Ala Leu Thr Glu
            165                 170                 175

Ile Pro Val Arg Ala Leu Asn Asn Leu Pro Ala Leu Gln Ala Met Thr
            180                 185                 190

Leu Ala Leu Asn His Ile Arg His Ile Pro Asp Tyr Ala Phe Gln Asn
            195                 200                 205

Leu Thr Ser Leu Val Val Leu His Leu His Asn Asn Arg Ile Gln His
            210                 215                 220

Val Gly Thr His Ser Phe Glu Gly Leu His Asn Leu Glu Thr Leu Asp
225                 230                 235                 240

Leu Asn Tyr Asn Glu Leu Gln Glu Phe Pro Leu Ala Ile Arg Thr Leu
            245                 250                 255

Gly Arg Leu Gln Glu Leu Gly Phe His Asn Asn Asn Ile Lys Ala Ile
            260                 265                 270

Pro Glu Lys Ala Phe Met Gly Ser Pro Leu Leu Gln Thr Ile His Phe
            275                 280                 285

Tyr Asp Asn Pro Ile Gln Phe Val Gly Arg Ser Ala Phe Gln Tyr Leu
            290                 295                 300

Ser Lys Leu His Thr Leu Ser Leu Asn Gly Ala Thr Asp Ile Gln Glu
305                 310                 315                 320

Phe Pro Asp Leu Lys Gly Thr Thr Ser Leu Glu Ile Leu Thr Leu Thr
            325                 330                 335

Arg Ala Gly Ile Arg Leu Leu Pro Pro Gly Val Cys Gln Gln Leu Pro
            340                 345                 350

Arg Leu Arg Ile Leu Glu Leu Ser His Asn Gln Ile Glu Glu Leu Pro
            355                 360                 365

Ser Leu His Arg Cys Gln Lys Leu Glu Glu Ile Gly Leu Arg His Asn
            370                 375                 380

Arg Ile Lys Glu Ile Gly Ala Asp Thr Phe Ser Gln Leu Gly Ser Leu
385                 390                 395                 400

Gln Ala Leu Asp Leu Ser Trp Asn Ala Ile Arg Ala Ile His Pro Glu
            405                 410                 415

Ala Phe Ser Thr Leu Arg Ser Leu Val Lys Leu Asp Leu Thr Asp Asn
            420                 425                 430

Gln Leu Thr Thr Leu Pro Leu Ala Gly Leu Gly Gly Leu Met His Leu
            435                 440                 445

Lys Leu Lys Gly Asn Leu Ala Leu Ser Gln Ala Phe Ser Lys Asp Ser
            450                 455                 460

Phe Pro Lys Leu Arg Ile Leu Glu Val Pro Tyr Ala Tyr Gln Cys Cys
465                 470                 475                 480

Ala Tyr Gly Ile Cys Ala Ser Phe Phe Lys Thr Ser Gly Gln Trp Gln
            485                 490                 495

Ala Glu Asp Phe His Pro Glu Glu Glu Ala Pro Lys Arg Pro Leu
            500                 505                 510

Gly Leu Leu Ala Gly Gln Ala Glu Asn His Tyr Asp Leu Asp Leu Asp
            515                 520                 525

Glu Leu Gln Met Gly Thr Glu Asp Ser Lys Pro His Pro Ser Val Gln
530                 535                 540

Cys Ser Pro Val Pro Gly Pro Phe Lys Pro Cys Glu His Leu Phe Glu
545                 550                 555                 560

Ser Trp Gly Ile Arg Leu Ala Val Trp Ala Ile Val Leu Leu Ser Val
            565                 570                 575
```

Leu Cys Asn Gly Leu Val Leu Leu Thr Val Phe Ala Ser Gly Pro Ser
            580                 585                 590

Pro Leu Ser Pro Val Lys Leu Val Val Gly Ala Met Ala Gly Ala Asn
            595                 600                 605

Ala Leu Ser Gly Ile Ser Cys Gly Leu Leu Ala Ser Val Asp Ala Leu
            610                 615                 620

Thr Tyr Gly Gln Phe Ala Glu Tyr Gly Ala Arg Trp Glu Ser Gly Leu
625                 630                 635                 640

Gly Cys Gln Ala Thr Gly Phe Leu Ala Val Leu Gly Ser Glu Ala Ser
            645                 650                 655

Val Leu Leu Leu Thr Leu Ala Ala Val Gln Cys Ser Ile Ser Val Thr
            660                 665                 670

Cys Val Arg Ala Tyr Gly Lys Ala Pro Ser Pro Gly Ser Val Arg Ala
            675                 680                 685

Gly Ala Leu Gly Cys Leu Ala Leu Ala Gly Leu Ala Ala Ala Leu Pro
            690                 695                 700

Leu Ala Ser Val Gly Glu Tyr Gly Ala Ser Pro Leu Cys Leu Pro Tyr
705                 710                 715                 720

Ala Pro Pro Glu Gly Arg Pro Ala Ala Leu Gly Phe Ala Val Ala Leu
            725                 730                 735

Val Met Met Asn Ser Leu Cys Phe Leu Val Val Ala Gly Ala Tyr Ile
            740                 745                 750

Lys Leu Tyr Cys Asp Leu Pro Arg Gly Asp Phe Glu Ala Val Trp Asp
            755                 760                 765

Cys Ala Met Val Arg His Val Ala Trp Leu Ile Phe Ala Asp Gly Leu
            770                 775                 780

Leu Tyr Cys Pro Val Ala Phe Leu Ser Phe Ala Ser Met Leu Gly Leu
785                 790                 795                 800

Phe Pro Val Thr Pro Glu Ala Val Lys Ser Val Leu Val Val Leu
            805                 810                 815

Pro Leu Pro Ala Cys Leu Asn Pro Leu Leu Tyr Leu Leu Phe Asn Pro
            820                 825                 830

His Phe Arg Asp Asp Leu Arg Arg Leu Trp Pro Ser Pro Arg Ser Pro
            835                 840                 845

Gly Pro Leu Ala Tyr Ala Ala Gly Glu Leu Glu Lys Ser Ser Cys
850                 855                 860

Asp Ser Thr Gln Ala Leu Val Ala Phe Ser Asp Val Asp Leu Ile Leu
865                 870                 875                 880

Glu Ala Ser Glu Ala Gly Gln Pro Pro Gly Leu Glu Thr Tyr Gly Phe
            885                 890                 895

Pro Ser Val Thr Leu Ile Ser Arg His Gln Pro Gly Ala Thr Arg Leu
            900                 905                 910

Glu Gly Asn His Phe Val Glu Ser Asp Gly Thr Lys Phe Gly Asn Pro
            915                 920                 925

Gln Pro Pro Met Lys Gly Glu Leu Leu Leu Lys Ala Glu Gly Ala Thr
            930                 935                 940

Leu Ala Gly Cys Gly Ser Ser Val Gly Gly Ala Leu Trp Pro Ser Gly
945                 950                 955                 960

Ser Leu Phe Ala Ser His Leu
            965

<210> SEQ ID NO 61
<211> LENGTH: 420
<212> TYPE: DNA

<213> ORGANISM: Artificial Sequence
<220> FEATURE:
<223> OTHER INFORMATION: Description of Artificial Sequence: Synthetic
    NR 2F10 LC polynucleotide

<400> SEQUENCE: 61

```
gacattcaga tgacgcagtc tccttcacta ctgtctgcat ctgtgggaga cagagtcact    60
ctcaactgca aagcaggtca gaatatcaac aattatttag cctggtatca gcaaaagctt   120
ggggcagctc ccaaagtcct gatatttat gcaaacagtt tgcaaacggg catcccatca    180
aggttcagtg gcagtggatc tggtacagat tacacactca ccatcagcag cctgcagcct   240
gaagatgttg ccacatattt ctgccagcag tattacattt ggaccacgtt tggagctggg   300
accaaggtgg aactgaaacg ggctgatgct gcaccaactg tatctatctt cccaccatcc   360
acggaacagt tagcaactgg aggtgcctca gtcgtgtgcc tcatgaacaa cttctatccc   420
```

<210> SEQ ID NO 62
<211> LENGTH: 368
<212> TYPE: DNA
<213> ORGANISM: Artificial Sequence
<220> FEATURE:
<223> OTHER INFORMATION: Description of Artificial Sequence: Synthetic
    OL 6d8 HC polynucleotide

<400> SEQUENCE: 62

```
gatgtgcaac tggtggagtc tgggggaggc ctagtgcagc ctggaaggtc tctgaaacta    60
tcctgtgtag cctctggatt cacattcaat aactactgga tgacctggat ccgccaggct   120
ccagggaagg ggctggagtg ggttgcatcc attactaata ctggtggaaa cacttactat   180
ccagactctg tgaagggccg attcactatc tccagagata tgcaataag taccctgtac    240 ctgcaaatga acagcctgac gtctgaggac acggccacgt attactgtac aagcgaggga   300
gggagtgggc ttgattattg gggccaagga gtcatggtca ctgtctctgc agccaaaacg   360
acaccccc                                                            368
```

<210> SEQ ID NO 63
<211> LENGTH: 365
<212> TYPE: DNA
<213> ORGANISM: Artificial Sequence
<220> FEATURE:
<223> OTHER INFORMATION: Description of Artificial Sequence: Synthetic
    OL 2F4 HC polynucleotide

<400> SEQUENCE: 63

```
gaggtgcagc ttcaggagtc tggacctggc cttgtgaaac cctcacagtc actctccctc    60
acctgttctg tcactggtta ctccatcact aagaattact ggggctggat ccggaagttc   120
ccaggaaata aaatggagtg gatgggatac ataagccaca gtggtagtat taagtacaat   180
acatctctca aaagtcgaat ctccattact agagacactt cgaagaatca gttcttcctg   240
cagttgaact ctctaactac tgaggacaca gccacatatt actgtgcaag tcaaactacc   300
cgaggttttg cttactgggg ccagggcact ctggtcactg tctctgcagc caaaacgaca   360
ccccc                                                               365
```

<210> SEQ ID NO 64
<211> LENGTH: 37
<212> TYPE: DNA
<213> ORGANISM: Artificial Sequence
<220> FEATURE:
<223> OTHER INFORMATION: Description of Artificial Sequence: Synthetic
    primer -continued

```
<400> SEQUENCE: 64
gggggtgtcg ttttggctga ggagacggtg accgtgg                              37

<210> SEQ ID NO 65
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gggggtgtcg ttttggctga ggagacggtg acagtgg                              37

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gggggtgtcg ttttggctga ggagacggtg accagag                              37

<210> SEQ ID NO 67
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gggggtgtcg ttttggctga ggagacggtg accgagg                              37
```